United States Patent
Sensfuss et al.

(10) Patent No.: US 7,541,430 B2
(45) Date of Patent: Jun. 2, 2009

(54) PEPTIDES FOR USE IN TREATING OBESITY

(75) Inventors: Ulrich Sensfuss, Valby (DK); Kilian Waldemar Conde Frieboes, Måløv (DK); Leif Christensen, Charlottenlund (DK); Ingrid Vivika Petterson, Frederiksberg (DK); Thomas Kruse Hansen, Herlev (DK); Michael Ankersen, Frederiksberg (DK); Kjeld Madsen, Værløse (DK)

(73) Assignee: Novo Nordisk A/S, Bagsvaerd (DK)

( * ) Notice: Subject to any disclaimer, the term of this patent is extended or adjusted under 35 U.S.C. 154(b) by 201 days.

(21) Appl. No.: 11/268,268

(22) Filed: Nov. 7, 2005

(65) Prior Publication Data

US 2007/0244054 A1  Oct. 18, 2007

Related U.S. Application Data

(63) Continuation of application No. PCT/DK2004/000308, filed on May 5, 2004.

(60) Provisional application No. 60/543,962, filed on Feb. 12, 2004, provisional application No. 60/470,639, filed on May 15, 2003.

(30) Foreign Application Priority Data

May 9, 2003  (DK) ................ 2003 00706
Feb. 5, 2004  (DK) ................ 2004 00172

(51) Int. Cl.
*A61K 38/10*  (2006.01)
(52) U.S. Cl. ............. 530/327; 530/328; 530/329; 530/306; 530/312; 530/317; 514/14; 514/15; 514/16

(58) Field of Classification Search ............. 514/14–16; 530/327–329, 306, 312, 317
See application file for complete search history.

(56) References Cited

U.S. PATENT DOCUMENTS 5,049,547 A * 9/1991 Hruby et al. ............... 514/14
5,731,408 A   3/1998 Hadley et al.
6,663,869 B1 * 12/2003 Rose et al. ............... 424/193.1
7,034,004 B2 * 4/2006 Haskell-Luevano et al. ... 514/18

FOREIGN PATENT DOCUMENTS

| WO | WO 98/27113  | 12/1996 |
| WO | WO 02/18437  | 8/2000  |
| WO | WO 02/81443  | 4/2001  |
| WO | WO 03/006604 | 7/2001  |
| WO | WO 03/006620 | 7/2001  |
| WO | WO 03/007949 | 7/2001  |
| WO | WO 03/009850 | 7/2001  |

OTHER PUBLICATIONS

Holder, JR et al., J Med Chem, vol. 45, pp. 2801-2810 (2002).
Holder JR et al., Eur J Pharmacol., vol. 462, pp. 41-52 (2003).
Bednarek, MA et al., Peptides, vol. 20, pp. 409-9 (1999).
Kavarana, MJ et al., J Med Chem, vol. 45, pp. 2644-2650 (2002).
Vergoni, AV et al., Eur J Pharmacol, vol. 179, pp. 347-355 (1990).
Huszar, D et al., Cell, vol. 88, pp. 131-141 (1997).
Klebig, ML et al., Proc Natl Acad Sci USA, vol. 92, pp. 4728-4732 (1995).
Yeo et al., Nat Genet, vol. 20, pp. 111-112 (1998).
Vaisse et al., Nat Genet, vol. 20, pp. 113-114 (1998).
Hadley, M et al., Pigment Cell Res, vol. 4, pp. 180-185 (1991).

* cited by examiner

*Primary Examiner*—David Lukton
(74) *Attorney, Agent, or Firm*—Shelby J. Walker

(57) ABSTRACT

Novel cyclic and linear peptides of the formula $R^1-X-X^1-X^2-X^3-X^4-X^5-X^6-X^7-X^8-X^9-X^{10}-X^{11}-R^2$ are useful in the treatment of obesity are provided.

72 Claims, No Drawings

PEPTIDES FOR USE IN TREATING OBESITY

CROSS-REFERENCE TO RELATED PATENT APPLICATIONS

This patent application is a continuation of copending International Patent Application PCT/DK2004/000308 (published as WO 2004/099246), which designates the United States, filed May 5, 2004, and claims the benefit of U.S. provisional patent applications 60/470,639 and 60/543,962, filed May 15, 2003 and Feb. 12, 2004, respectively, and Danish Patent Applications PA 2003 00706 and PA 2004 00172, filed May 9, 2003 and Feb. 5, 2004, respectively, the entirety of each of which being hereby incorporated by reference.

FIELD OF THE INVENTION

The present invention relates to novel peptides which are specific to one or more melanocortin receptor and which exert a prolonged activity, to the use of said peptides in therapy, to methods of treatment comprising administration of said peptides to patients, and to the use of said peptides in the manufacture of medicaments.

BACKGROUND OF THE INVENTION

Obesity is a well known risk factor for the development of many very common diseases such as atherosclerosis, hypertension, type 2 diabetes (non-insulin dependent diabetes mellitus (NIDDM)), dyslipidaemia, coronary heart disease, and osteoarthritis and various malignancies. It also causes considerable problems through reduced motility and decreased quality of life. The incidence of obesity and thereby also these diseases is increasing throughout the entire industrialised world. Only a few pharmacological treatments are available to date, namely Sibutramine (acting via serotonergic and noradrenaline mechanisms, Abbott) and Orlistat (reducing fat uptake from the gut, Roche Pharm). However, due to the important effect of obesity as a risk factor in serious and even mortal and common diseases there is still a need for pharmaceutical compounds useful in the treatment of obesity.

The term obesity implies an excess of adipose tissue. In this context obesity is best viewed as any degree of excess adiposity that imparts a health risk. The distinction between normal and obese individuals can only be approximated, but the health risk imparted by obesity is probably a continuum with increasing adiposity. However, in the context of the present invention, individuals with a body mass index (BMI=body weight in kilograms divided by the square of the height in meters) above 25 are to be regarded as obese.

Even mild obesity increases the risk for premature death, diabetes, hypertension, atherosclerosis, gallbladder disease and certain types of cancer. In the industrialized western world the prevalence of obesity has increased significantly in the past few decades. Because of the high prevalence of obesity and its health consequences, its treatment should be a high public health priority.

When energy intake exceeds energy expenditure, the excess calories are stored in adipose tissue, and if this net positive balance is prolonged, obesity results, i.e. there are two components to weight balance, and an abnormality on either side (intake or expenditure) can lead to obesity.

Pro-opiomelanocortin (POMC) is the precursor for β-endorphin and melanocortin peptides, including melanocyte stimulating hormone (α-MSH) and adrenocorticotropin (ACTH). POMC is expressed in several peripheral and central tissues including melanocytes, pituitary and neurones of the hypothalamus. The POMC precursor is processed differently in different tissues resulting in the expression of different melanocortin peptides depending on the site of expression. In the anterior lobe of the pituitary, mainly ACTH is produced whereas in the intermediate lobe and the hypothalamic neurones the major peptides are α-MSH, β-MSH, desacetyl-α-MSH and β-endorphin. Several of the melanocortin peptides, including ACTH and α-MSH, have been demonstrated to have appetite suppressing activity when injected intracerebroventricular in rats (Vergoni et al, European Journal of Pharmacology 179, 347-355 (1990)). An appetite suppressing effect is also obtained with the artificial cyclic α-MSH analogue, MT-II.

A family of five melanocortin receptor subtypes has been identified (melanocortin receptor 1-5, also called MC1, MC2, MC3, MC4 and MC5). The MC1, MC2 and MC5 are mainly expressed in peripheral tissues whereas MC3 and MC4 are mainly centrally expressed, however MC3 are also expressed in several peripheral tissues. MC3 receptors have besides being involved in energy homeostasis also been suggested to be involved in several inflammatory diseases. An MC3 agonist could have a positive effect on these diseases, e.g. gouty arthritis. MC5 are mainly peripheral expressed and has been suggested to be involved in exocrine secretion and in inflamation. MC4 is shown to be involved in the regulation of body weight and feeding behaviour as MC4 knock out mice develop obesity (Huzar et al, Cell 88, 131-141 (1997)). Furthermore studies of either ectopic centrally expression of agouti (MC1, MC3 and MC4 antagonist) or over-expression of an endogenously occurring MC3 and MC4 antagonist (agouti gene related peptide, AGRP) in the brain demonstrated that the over-expression of these two antagonists lead to the development of obesity (Kleibig et al, PNAS 92, 4728-4732 (1995)). Furthermore, icv injection of a C-terminal fragment of AGRP increases feeding and antagonises the inhibitory effect of α-MSH on food intake.

In humans several cases of families with obesity presumably due to frame shift mutations in MC4 have been described (e.g. Yeo et al, Nature Genetics 20, 111-112 (1998), Vaisse et al, Nature Genetics 20, 113-114).

In conclusion, a MC4 agonist could serve as an anorectic drug, and be useful in the treatment of obesity or obesity related diseases as well as in the treatment of other diseases, disorders or conditions, which are improved by activation of MC4.

MC4 antagonists may be useful for treatment of cachaxia, anorexia, and for treatment of waisting in frail elderly patients. Furthermore, MC4 antagonists may be used for treatment of chronic pain, neuropathy and neurogenic inflammation.

A large number of patent applications disclose small molecules as melanocortin receptor modulators, examples of which are WO 03/009850, WO 03/007949 and WO 02/081443.

The use of peptides as melanocortin receptor modulators is also disclosed in a number of patents, e.g. WO 03/006620, U.S. Pat. No. 5731,408 and WO 98/27113. Hadley in *Pigment Cell Res.*, 4, 180-185, 1991 obtains a prolonged effect of specific melanotropic peptides conjugated to fatty acids, said prolongation being effected by a transformation of the modulators from being reversibly to being irreversibly acting caused by the conjugated fatty acids.

Sequence Listing

The sequences of the polynucleotides and polypeptides of the invention are listed in the Sequence Listing and are submitted on a compact disc containing the file labeled 6648-WO sequence listing.txt (68 Kb) which was created on an IBM PC, Windows 2000 operating system on Nov. 7, 2005 at 10 AM. The Sequence Listing is herein incorporated by reference in its entirety. A computer readable format ("CRF") and two duplicate copies ("Copy 1/2" and "Copy 2/2") of the Sequence Listing are submitted herein. Applicants hereby state that the content of the CRF and Copies 1/2, and 2/2 of the Sequence Listing, submitted in accordance with 37 CFR .sctn.1.821 (c) and (e), respectively, are the same.

SUMMARY OF THE INVENTION

The present inventors have surprisingly found that specific peptide conjugates have a high modulating effect on one or more melanocortin receptors, i.e. the MC1, MC2, MC3, MC4 or MC5 receptors. Accordingly, the invention relates to a peptide according to formula I

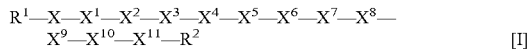

wherein $R^1$, which is bonded to an N-terminal $NH_2$-group, is either absent or represents $C_{1-4}$alkanoyl or $R^4$, which is a protracting group, optionally attached to X via a linker, S;

X represents a bond or an amino acid, a di- or tri-peptide residue, wherein the amino acid(s) may be natural or synthetic;

$X^1$ represents a bond or an amino acid residue with a functional group in the side chain to which a protracting group, $R^4$, may be attached, optionally via a linker, S;

$X^2$ represents a bond or an amino acid, di-, tri- or tetra-peptide residue, wherein the amino acid(s) may be natural or synthetic;

$X^3$ represents a bond or an amino acid residue optionally capable of making a bridge to $X^{10}$;

$X^4$ represents a bond or an amino acid or di-peptide residue, wherein the amino acid(s) may be natural or synthetic;

$X^5$ represents an amino acid residue selected from His, Ala, Nle, Met, Met(O), Met($O_2$), Gln, Gln($\epsilon$-alkyl), Gln($\epsilon$-aryl), Asn, Asn($\epsilon$-alkyl), Asn($\epsilon$-aryl), Ser, Thr, Cys, F-Pro, Pro, Hyp, (S)-1,2,3,4-tetrahydroisoquinoline-3-carboxylic acid, Trp, 1-naphthylalanine, 2-naphthylalanine, 2-pyridylalanine, 3-pyridylalanine, 4-pyridylalanine, 2-thienylalanine, 3-thienylalanine, 4-thiazolylalanine, 2-furylalanine, 3-furylalanine, Phe, wherein the phenyl moiety of said Phe is optionally substituted by halogen, hydroxyl, alkoxy, nitro, benzoyl, methyl, trifluoromethyl or cyano;

$X^6$ represents (D)-Phe, wherein the phenyl moiety of said (D)-Phe is optionally substituted with halogen, hydroxy, alkoxy, nitro, methyl, trifluoromethyl or cyano;

$X^7$ represents Arg;

$X^8$ represents Trp or 2-naphthylalanine;

$X^9$ represents a bond or an amino acid, or di-peptide residue, wherein the amino acid(s) may be natural or synthetic;

$X^{10}$ represents a bond or an amino acid residue optionally capable of making a bridge to $X^3$;

$X^{11}$ represents a bond, an amino acid or a di-peptide, wherein the amino acid(s) may be natural or synthetic;

$R^2$ represents —OH or —NRR', wherein R and R' independently represent hydrogen, $C_{1-8}$alkyl, $C_{2-8}$alkenyl or $C_{2-8}$alkynyl;

wherein the peptide of formula I is optionally cyclized from $X^3$ to $X^{10}$ via a lactame or a disulfide bridge;

with the provision that the compound according to formula I comprises one protracting group; and with the further proviso that compounds of formula I comprises at least 7 amino acid residues;

and any pharmaceutically acceptable salt, solvate or hydrate thereof.

The invention also relates to the use of compounds of formula I in therapy, and in particular to pharmaceutical compositions comprising compounds of formula I.

The invention also relates to methods of treatment comprising administering to a subject in need thereof an effective amount of a compound of formula I.

The invention also relates to the use of compounds of formula I in the manufacture of medicaments.

Definitions

The use of prefixes of the structure: $C_{x-y}$-alkyl, $C_{x-y}$-alkenyl, $C_{x-y}$-alkynyl or $C_{x-y}$-cycloalkyl designates radical of the designated type having from x to y carbon atoms.

The term "alkyl" as used herein without prefixes refers to a straight or branched chain saturated monovalent hydrocarbon radical having for instance from one to ten carbon atoms, for example $C_{1-8}$-alkyl. Typical $C_{1-8}$-alkyl groups include, e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-pentyl, n-hexyl, 1,2-dimethylpropyl, 2,2-dimethylpropyl, 1,2,2-trimethylpropyl and the like. The term "$C_{1-8}$-alkyl" as used herein also includes secondary $C_{3-8}$-alkyl and tertiary $C_{4-8}$-alkyl. More generally, the term "alkyl" is intended to indicate both primary, secondary and tertiary alkyl.

The term "alkenyl" as used herein without prefixes, refers to a straight or branched chain monovalent non-aromatic hydrocarbon radical having for instance from two to ten carbon atoms and at least one carbon-carbon double bond, for example $C_{2-8}$-alkenyl. Typical $C_{2-8}$-alkenyl groups include vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl and 2,4-hexadienyl, 5-hexenyl.

In the present context, the term alkynyl used without prefixes is intended to indicate a straight or branched chain non-aromatic monovalent hydrocarbon having at least one carbon-carbon tripel bond and optionally one or more carbon-carbon double bonds having fro instance from 2 to 10 carbon atoms. Examples of alkynyl include 2-propynyl, 2-butynyl and 1,3-hexadiene-5-ynyl.

In the present context, the term "alkanoyl" is intended to indicate a radical of the formula —C(O)—R', wherein R' is alkyl as indicated above.

In the present context, the term "alkenoyl" is intended to indicate a radical of the formula —C(O)—R", wherein R" is alkenyl as indicated above.

In the present context, the term "alkynoyl" is intended to indicate a radical of the formula —C(O)—R'", wherein R'" is alkynyl as indicated above.

The term "halogen" is intended to indicate fluoro, chloro, bromo and iodo.

The term "alkoxy" is intended to indicate a radical of the formula —O—R', wherein R' is alkyl as indicated above.

In the present context, the term "aryl" is intended to indicate a carbocyclic aromatic ring radical or a fused aromatic ring system radical wherein at least one of the rings are aromatic. Typical aryl groups include phenyl, biphenylyl, naphtyl, and the like.

In the present context, AA(X), wherein AA indicates an amino acid, is intended to indicate that X is attached to the functional group in the side chain of the amino acid.

When two amino acids are said to be bridged it is intended to indicate that functional groups the side chains of the two amino acids have reacted to form a covalent bond.

In the present context, the term "agonist" is intended to indicate a substance that activates the receptors.

In the present context, the term "antagonist" is intended to indicate a substance that neutralizes or counteracts the effect of an agonist.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

A "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal, in particular a human being, but it may also include animals, such as dogs, cats, cows, sheep and pigs.

As used herein, the term "solvate" is a complex of defined stoichiometry formed by a solute (in casu, a compound according to the present invention) and a solvent. Solvents may be, by way of example, water, ethanol, or acetic acid.

In addition the following abbreviations have the meanings given

| | |
|---|---|
| Ac | acetyl |
| 4-Abu | 4-aminobutyric acid |
| Ala | alanine |
| Arg | arginine |
| Arg(Pmc) | 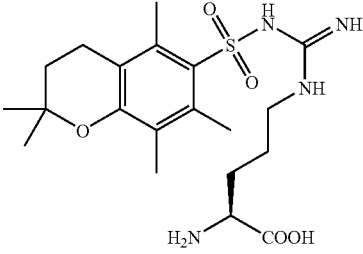 |
| Asn | asparagine |
| Asn(alkyl) | 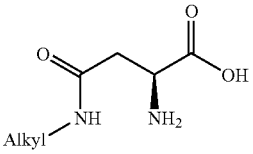 |
| Asn(aryl) | 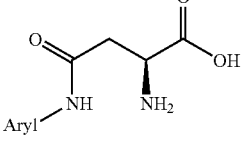 |
| Asp | aspartic acid |
| Boc | tert-butyloxycarbonyl |
| Cys | cysteine |
| D-Phe | D form of phenylalanine |
| Fmoc | 9-fluorenylmethoxycarbonyl |
| F-Pro | 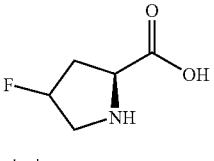 |
| Gly | glycine |
| Gln | glutamine |
| Gln(alkyl) | 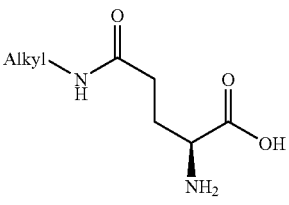 |
| Gln(aryl) | 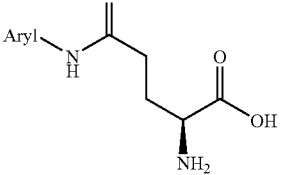 |

-continued

| | |
|---|---|
| Glu | glutamic acid |
| His | histidine |
| homoArg | 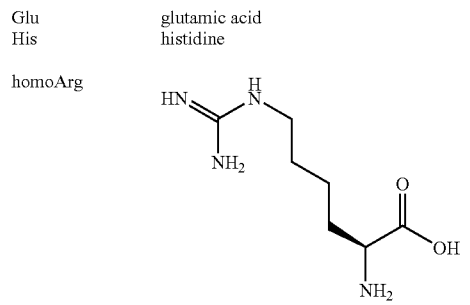 |
| homoCys | 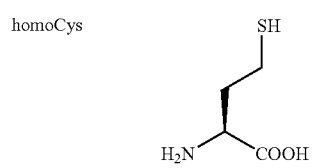 |
| Hyp | 4-hydroxyproline |
| Ile | isoleucine |
| Leu | leucine |
| Lys | lysine |
| Met | methionine |
| Met(O) | 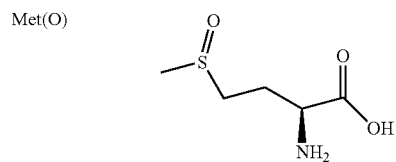 |
| Met(O$_2$) | 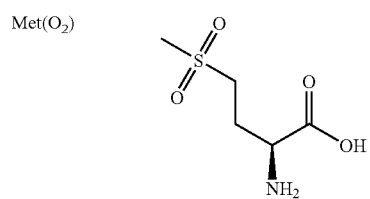 |
| mPEG2000 | methoxypolyethylenglycol (average molecular weight of 2000 Dalton) |
| Mtt | 4-methyltrityl |
| 2Nal | 2-Naphthyl alanine |
| Nle | norleucine |
| Orn | ornithine |
| Phe | phenylalanine |
| Pro | proline |
| 2-PyAla | 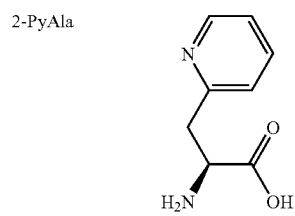 |
| 3-PyAla | 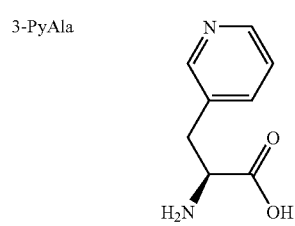 |

-continued

| | |
|---|---|
| 4-PyAla | 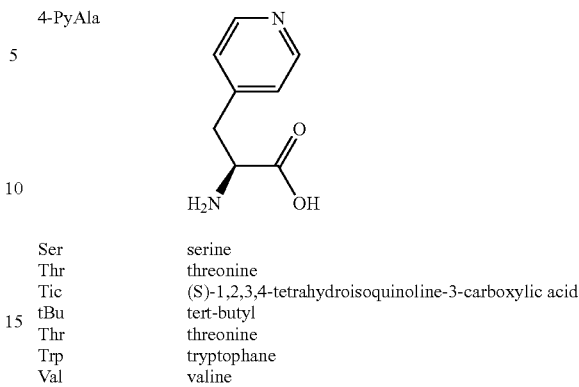 |
| Ser | serine |
| Thr | threonine |
| Tic | (S)-1,2,3,4-tetrahydroisoquinoline-3-carboxylic acid |
| tBu | tert-butyl |
| Thr | threonine |
| Trp | tryptophane |
| Val | valine |

DESCRIPTION OF THE INVENTION

In one embodiment, in which the peptide according to formula I may be either cyclic or non-cyclic, $R^4$ represents a straight, branched and/or cyclic $C_{8-22}$alkanoyl, $C_{8-22}$alkenoyl or $C_{8-22}$alkynoyl, all of which may optionally be substituted with one or more substituents selected from hydroxyl, halogen, carboxyl and aryl, wherein said aryl may optionally be further substitututed by one or more substituents selected from hydroxyl, halogen, and carboxyl;

or wherein $R^4$ represents $C_{7-17}$alkyl-C(O)—NH—S(O)$_2$—C(O)—, wherein said alkyl may be substituted with one or more halogens, such as e.g. fluoro;

or wherein $R^4$ represents $R^5$—C(O)—NH—S(O)$_2$—(CH$_2$)$_3$—C(O)—, wherein $R^5$ represents 1-(4-benzoylphenyl);

or wherein $R^4$ represents a steroid represented by formula II or IIa

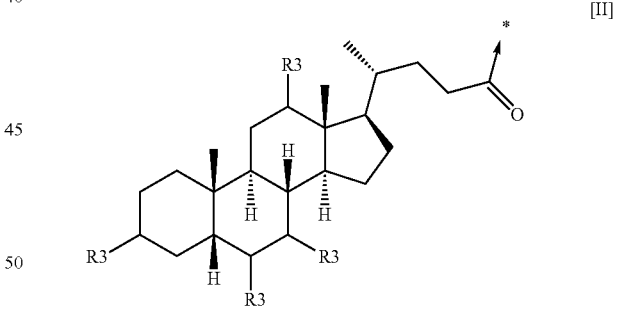

[II]

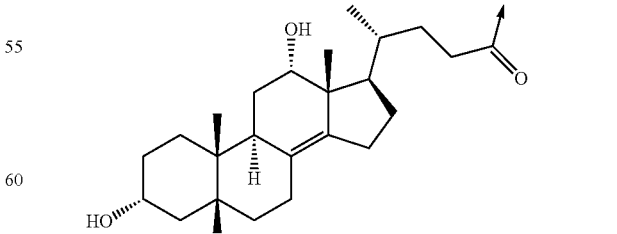

[IIa]

wherein each $R^3$ independently represents hydrogen, hydroxyl or $R^3$ together with the bond which binds it to the ring carbon constitute =O;

or wherein $R^4$ represents a structure according to formula III, IIIa, IIIb, IV or IVa

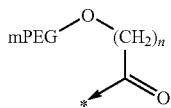
[III]

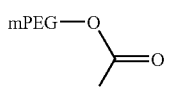
[IIIa]

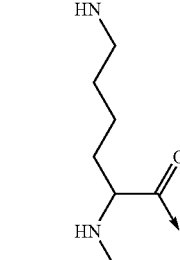
[IIIb]

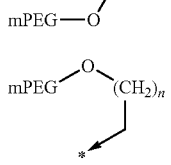
IV

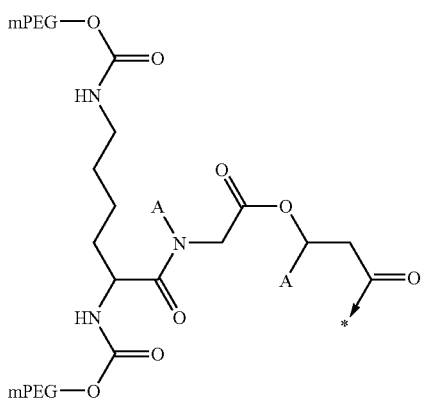
[IVa]

wherein n is 1, 2, or 3;

each mPEG independently represents methoxy polyethylene glycol with a molecular weight between about 2 kDa and about 50 kDa;
each A independently represents hydrogen or $C_{1-4}$alkyl;
and wherein $X^3$ represents Lys, Orn, 2,4-diamino butyric acid, 2,3-diamino propionic acid, Cys, homoCys, Glu, Asp, Gln or Asn;
and wherein $X^{10}$ represents Lys, Orn, 2,4-diamino butyric acid, 2,3-diamino propionic acid, Cys, homoCys, Glu, Asp, Gln or Asp;
and wherein the linker S if present represents β-alanine, Glu, Gly-Gln, Gly-Glu, Gly-His or

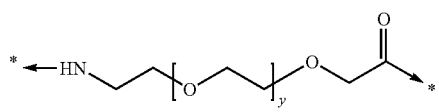

y being 1,2,3,4 or 5.

Cyclic Compounds of Fomula I

In this embodiment, there is a bond between $X^3$ and $X^{10}$ to make the compound of formula I cyclic by a disulfide bridge ($X^3$, $X^{10}$ are independently Cys or homoCys) or by a lactam bond between an acid in the side chain of $X^3$ or $X^{10}$ and an amine in the side chain of $X^{10}$ or $X^3$.

In one embodiment, X is a bond.
In one embodiment, $X^1$ represents a bond.
In one embodiment, $X^2$ represents Nle.
In one embodiment, $X^3$ represents Glu or Asp and $X^{10}$ represents Lys, Orn, 2,4-diamino butyric acid or 2,3-diamino propionic acid. In particular, $X^3$ represents Glu or Asp, and $X^{10}$ represents Lys.
In one embodiment, $X^4$ represents a bond.
In one embodiment, $X^5$ represents Ala, Nle, Met, Met(O), Met($O_2$), Gln, Gln(ϵ-alkyl), Gln(ϵ-aryl), Asn, Asn (ϵ-alkyl), Asn(ϵ-aryl), Ser, Thr, Cys, F-Pro, Pro, Hyp, (S)-1,2,3,4-tetrahydroisoquinoline-3-carboxylic acid, Trp, 1-naphthylalanine, 2-naphthylalanine, 2-PyAla, 3-PyAla, 4-PyAla, 2-thienylalanine, 3-thienylalanine, 4-thiazolylalanine, 2-furylalanine, 3-furylalanine, Phe, wherein the phenyl moiety of said Phe is optionally substituted by halogen, hydroxyl, alkoxy, nitro, benzoyl, methyl, trifluoromethyl or cyano.
In one embodiment, $X^5$ represents His.
In one embodiment, $X^5$ represents 3-PyAla, Hyp, Gln or Asn.
In one embodiment, $X^9$ represents a bond.
In one embodiment, $X^{11}$ represents a bond.
In one embodiment, $R^2$ represents —$NH_2$.
In one embodiment, $X^6$—$X^7$—$X^8$—$X^9$—$X^{10}$ represents D-Phe-Arg-Trp-Lys.
In one embodiment, the compound according to formula I is selected from amongst

```
R⁴-Nle-c[Asp-3-PyAla-D-Phe-Arg-Trp-Lys]-R²;    (SEQ ID NO: 1)

R⁴-Nle-c[Glu-Hyp-D-Phe-Arg-Trp-Lys]-R²;        (SEQ ID NO: 2)

R⁴-Nle-c[Glu-Hyp-D-Phe-Arg-Trp-Lys]-R²;        (SEQ ID NO: 3)

R⁴-Nle-c[Glu-Gln-D-Phe-Arg-Trp-Lys]-R²;        (SEQ ID NO: 4)

R⁴-Nle-c[Asp-Gln-D-Phe-Arg-Trp-Lys]-R²;        (SEQ ID NO: 5)
```

```
R⁴-Nle-c[Glu-Asn-D-Phe-Arg-Trp-Lys]-R²;         (SEQ ID NO: 6)

R⁴-Nle-c[Asp-Asn-D-Phe-Arg-Trp-Lys]-R²;         (SEQ ID NO: 7)

R⁴-Nle-c[Glu-3-PyAla-D-Phe-Arg-2Nal-Lys]-R²;    (SEQ ID NO: 8)

R⁴-Nle-c[Asp-3-PyAla-D-Phe-Arg-2Nal-Lys]-R²;    (SEQ ID NO: 9)

R⁴-Nle-c[Glu-Hyp-D-Phe-Arg-2Nal-Lys]-R²;        (SEQ ID NO: 10)

R⁴-Nle-c[Asp-Hyp-D-Phe-Arg-2Nal-Lys]-R²;        (SEQ ID NO: 11)

R⁴-Nle-c[Glu-Gln-D-Phe-Arg-2Nal-Lys]-R²;        (SEQ ID NO: 12)

R⁴-Nle-c[Asp-Gln-D-Phe-Arg-2Nal-Lys]-R²;        (SEQ ID NO: 13)

R⁴-Nle-c[Glu-Asn-D-Phe-Arg-2Nal-Lys]-R²;        (SEQ ID NO: 14)
and

R⁴-Nle-c[Asp-Asn-D-Phe-Arg-2Nal-Lys]-R².        (SEQ ID NO: 15)
```

In one embodiment, $X—X^1—X^2—X^3—X^4—X^5—X^6—X^7—X^8—X^9—X^{10}-R^2$ represents Nle-c[Glu-3-PyAla-D-Phe-Arg-Trp-Lys]-NH$_2$ (SEQ ID NO: 16) or Nle-c[Glu-Hyp-D-Phe-Arg-Trp-Lys]-NH$_2$ (SEQ ID NO: 2).

In one embodiment, $X—X^1—X^2—X^3—X^4—X^5—X^6—X^7—X^8—X^9—X^{10}-R^2$ represents Nle-c[Glu-His-D-Phe-Arg-Trp-Lys]-NH$_2$ (SEQ ID NO: 17).

In one embodiment, $X—X^1—X^2$ is represented by a moiety of the formula $Z^1-Z^2-Z^3-Z^4-Z^5-Z^6$, wherein $Z^1$ represents Gly; $Z^2$ represents Ser, (D)-Ser or Thr; $Z^3$ represents Gln, Asn, (D)-Gln or (D)-Asn; $Z^4$ represents His, homoArg, Arg, Lys or Orn; $Z^5$ represents Ser, (D)-Ser or Thr; and $Z^6$ represents Nle. In particular, $X^3$ represents Glu, and $X^{10}$ represents Lys, and in particular $X^4$, $X^9$ and $X^{11}$ represent a bond. In this embodiment, $X^5$ may represent Ala, Nle, Met, Met(O), Met(O2), Gln, Gln(ε-alkyl), Gln(ε-aryl), Asn, Asn (ε-alkyl), Asn(ε-aryl), Ser, Thr, Cys, Pro, F-Pro, Hyp, (S)-1,2,3,4-tetrahydroisoquinoline-3-carboxylic acid, Trp, 1-naphthylalanine, 2-naphthylalanine, 2-PyAla, 3-PyAla, 4-PyAla, 2-thienylalanine, 3-thienylalanine, 4-thiazolylalanine, 2-furylalanine, 3-furylalanine, Phe, wherein the phenyl moiety of said Phe is optionally substituted by halogen, hydroxyl, alkoxy, nitro, benzoyl, methyl, trifluoromethyl or cyano. In particular, $X^5$ may represent F-Pro, Hyp or Gln. In particular $R^2$ represents —NH$_2$, and particular mentioning is made of $X^6—X^7—X^8—X^9—X^{10}$ representing (D)-Phe-Arg-Trp-Lys.

In one embodiment, the moiety of the formula $Z^1-Z^2-Z^3-Z^4-Z^5-Z^6$ is selected from amongst

```
Gly-Ser-Asn-Asn-Thr-Nle;         (SEQ ID NO: 18)

Gly-Ser-Asn-homoArg-Thr-Nle;     (SEQ ID NO: 19)

Gly-Ser-DAsn-His-Thr-Nle;        (SEQ ID NO: 20)

Gly-Ser-DAsn-homoArg-Thr-Nle;    (SEQ ID NO: 21)

Gly-Ser-Gln-Arg-Ser-Nle;         (SEQ ID NO: 22)

Gly-Ser-Gln-His-Ser-Nle;         (SEQ ID NO: 23)

Gly-Ser-Gln-homoArg-Ser-Nle;     (SEQ ID NO: 24)

Gly-Ser-Gln-homoArg-Thr-Nle;     (SEQ ID NO: 25)

Gly-Ser-Gln-Lys-Ser-Nle;         (SEQ ID NO: 26)

Gly-Ser-Gln-Orn-Ser-Nle;         (SEQ ID NO: 27)

Gly-Ser-Ser-His-Thr-Nle          (SEQ ID NO: 28)
and

Gly-Ser-Ser-Tyr-Thr-Nle.         (SEQ ID NO: 29)
```

In one embodiment, $X^3—X^4—X^5—X^6—X^7—X^8—X^9—X^{10}—X^{11}-R^2$ is selected from

```
cyclo[Glu-3-PyAla-(D)-Phe-Arg-Trp-Lys]-NH₂;    (SEQ ID NO: 30)

cyclo[Glu-F-Pro-(D)-Phe-Arg-Trp-Lys]-NH₂;      (SEQ ID NO: 31)

cyclo[Glu-Gln-(D)-Phe-Arg-Trp-Lys]-NH₂;        (SEQ ID NO: 32)

cyclo[Glu-Hyp-(D)-Phe-Arg-Trp-Lys]-NH₂;        (SEQ ID NO: 33)
and cyclo[Glu-Met(O2)-(D)-Phe-Arg-Trp-Lys]-NH₂.    (SEQ ID NO: 34)
```

Non-cyclic Peptides

In one embodiment, the compound of formula I is non-cyclic.

In one embodiment, X represents a bond.

In one embodiment, X represents an amino acid residue, such as e.g. Ser.

In one embodiment, $X^1$ represents Lys(N$^ε$β-Ala-R$^4$).

In one embodiment, $X^1$ represents a bond.

In one embodiment, $X^2$ represents Tyr-Ser-Nle.

In one embodiment, $X^2$ represents Ser-Nle.

In one embodiment, $X^2$ represents Ser-Tyr-Ser-Nle.

In one embodiment, $X^3$ represents Glu.

In one embodiment, $X^4$ represents a bond.

In one embodiment, $X^5$ represents Ala, Nle, Met, Met(O), Met($O_2$), Gln, Gln($\epsilon$-alkyl), Gln($\epsilon$-aryl), Asn, Asn($\epsilon$-alkyl), Asn($\epsilon$-aryl), Ser, Thr, Cys, F-Pro, Pro, Hyp, (S)-1,2,3,4-tetrahydroisoquinoline-3-carboxylic acid, Trp, 1-naphthylalanine, 2-naphthylalanine, 2-PyAla, 3-PyAla, 4-PyAla, 2-thienylalanine, 3-thienylalanine, 4-thiazolylalanine, 2-furylalanine, 3-furylalanine, Phe, wherein the phenyl moiety of said Phe is optionally substituted by halogen, hydroxyl, alkoxy, nitro, benzoyl, methyl, trifluoromethyl or cyano.

In one embodiment, $X^5$ represents His.

In one embodiment, $X^5$ represents Gln, Hyp, 3-PyAla, Ala or Ser.

In one embodiment, $X^9$ represents Gly.

In one embodiment, $X^{10}$ represents Lys or Arg.

In one embodiment, $X^{11}$ represents Pro-Val.

In one embodiment, $R^2$ represents —$NH_2$.

In one embodiment, $R^1$—X—$X^1$—$X^2$—$X^3$—$X^4$—$X^5$—$X^6$—$X^7$—$X^8$—$X^9$—$X^{10}$—$R^2$ represents a compound selected from amongst

```
CH3C(O)-Lys(Nεβ-Ala-R4)-Tyr-Ser-Nle-Glu-Hyp-D-Phe-Arg-Trp-Gly-Lys-Pro-Val-NH2        (SEQ ID NO: 35)

CH3C(O)-Lys(Nεβ-Ala-R4)-Tyr-Ser-Nle-Glu-3-PyAla-D-Phe-Arg-Trp-Gly-Lys-Pro-Val-NH2,   (SEQ ID NO: 36)

CH3C(O)-Lys(Nεβ-Ala-R4)-Tyr-Ser-Nle-Glu-Ser-D-Phe-Arg-Trp-Gly-Arg-Pro-Val-NH2,       (SEQ ID NO: 37)

CH3C(O)-Lys(Nεβ-Ala-R4)-Tyr-Ser-Nle-Glu-Ala-D-Phe-Arg-Trp-Gly-Arg-Pro-Val-NH2,       (SEQ ID NO: 38)

CH3C(O)-Lys(Nεβ-Ala-R4)-Tyr-Ser-Nle-Glu-Gln-D-Phe-Arg-Trp-Gly-Arg-Pro-Val-NH2,       (SEQ ID NO: 39)
and CH3C(O)-Lys(Nεβ-Ala-R4)-Tyr-Ser-Nle-Glu-Hyp-D-Phe-Arg-Trp-Gly-Arg-Pro-Val-NH2        (SEQ ID NO: 40)
```

In one embodiment, $R^1$—X—$X^1$—$X^2$—$X^3$—$X^4$—$X^5$—$X^6$—$X^7$—$X^8$—$X^9$—$X^{10}$—$X^{11}$—$R^2$ represents a compound selected from amongst

```
CH3C(O)-Ser-Lys(Nεβ-Ala-R4)-Ser-Nle-Glu-Hyp-D-Phe-Arg-Trp-Gly-Lys-Pro-Val-NH2,       (SEQ ID NO: 41)

CH3C(O)-Ser-Lys(Nεβ-Ala-R4)-Ser-Nle-Glu-3-PyAla-D-Phe-Arg-Trp-Gly-Lys-Pro-Val-NH2,   (SEQ ID NO: 42)

CH3C(O)-Ser-Lys(Nεβ-Ala-R4)-Ser-Nle-Glu-Ser-D-Phe-Arg-Trp-Gly-Arg-Pro-Val-NH2,       (SEQ ID NO: 43)

CH3C(O)-Ser-Lys(Nεβ-Ala-R4)-Ser-Nle-Glu-Ala-D-Phe-Arg-Trp-Gly-Arg-Pro-Val-NH2,       (SEQ ID NO: 44)

CH3C(O)-Ser-Lys(Nεβ-Ala-R4)-Ser-Nle-Glu-Gln-D-Phe-Arg-Trp-Gly-Arg-Pro-Val-NH2,       (SEQ ID NO: 45)

CH3C(O)-Ser-Lys(Nεβ-Ala-R4)-Ser-Nle-Glu-Hyp-D-Phe-Arg-Trp-Gly-Arg-Pro-Val-NH2,       (SEQ ID NO: 46)
and CH3C(O)-Ser-Lys(Nεβ-Ala-R4)-Ser-Nle-Glu-3-PyAla-D-Phe-Arg-Trp-Gly-Arg-Pro-Val-NH2.  (SEQ ID NO: 47)
```

In one embodiment, $R^1$—X—$X^1$—$X^2$—$X^3$—$X^4$—$X^5$—$X^6$—$X^7$—$X^8$—$X^9$—$X^{10}$—$X^{11}$—$R^2$ represents a compound selected from amongst

```
R4-Ser-Tyr-Ser-Nle-Glu-Gln-D-Phe-Arg-Trp-Gly-Lys-Pro-Val-NH2,     (SEQ ID NO: 48)

R4-Ser-Tyr-Ser-Nle-Glu-Hyp-D-Phe-Arg-Trp-Gly-Lys-Pro-Val-NH2,     (SEQ ID NO: 49)

R4-Ser-Tyr-Ser-Nle-Glu-3-PyAla-D-Phe-Arg-Trp-Gly-Lys-Pro-Val-NH2, (SEQ ID NO: 50)

R4-Ser-Tyr-Ser-Nle-Glu-Ser-D-Phe-Arg-Trp-Gly-Arg-Pro-Val-NH2,     (SEQ ID NO: 51)

R4-Ser-Tyr-Ser-Nle-Glu-Ala-D-Phe-Arg-Trp-Gly-Arg-Pro-Val-NH2,     (SEQ ID NO: 52)

R4-Ser-Tyr-Ser-Nle-Glu-Gln-D-Phe-Arg-Trp-Gly-Arg-Pro-Val-NH2,     (SEQ ID NO: 53)

R4-Ser-Tyr-Ser-Nle-Glu-Hyp-D-Phe-Arg-Trp-Gly-Arg-Pro-Val-NH2,     (SEQ ID NO: 54)
and R4-Ser-Tyr-Ser-Nle-Glu-3-PyAla-D-Phe-Arg-Trp-Gly-Arg-Pro-Val-NH2. (SEQ ID NO: 55)
```

Protracting Group

One function of the $R^4$ substituent is to protract the effect of the compounds, i.e. to prolong the period of time in which they exert a biological activity. A protracting effect may be evaluated in a slightly modified Assay I in a comparison between compounds wherein $R^1$ and $R^4$ is absent and compounds wherein $R^4$ represents the protracting substituent to be tested. The experiment is allowed to continue for a period of time, T, until the rats eat as much as they did prior to the experiment. T values for $R^4$ believed to be a protracting group and $R^1$ and $R^4$ being absent are measured, and the difference $\Delta T$ is calculated. Groups giving rise to $\Delta T$ above 3 hours, such as above 7 hours, such as above 12 hours, such as above 12 hours, such as above 24 hours, such as above 48 hours, such as above 72 hours are deemed to be protracting groups. In the context of the present invention, the $C_{1-4}$alkanoyl group which $R^1$ may represent is not regarded as a protracting group.

In addition to protracting the effect of a compound, $R^4$ may also enhance the potency by which the compound of the present invention modulates the melanocortin receptor compared to a compound wherein $R^1$ and $R^4$ is absent. Such enhanced potency may be measured by testing the compound in melanocortin assay described in assay VI herein.

In one embodiment, $R^4$ represents a straight, branched and/or cyclic $C_{8-20}$alkanoyl, $C_{8-20}$alkenoyl or $C_{8-20}$alkynoyl, all of which may optionally be substituted with one or more substituents selected from hydroxyl, halogen, carboxyl and aryl, wherein said aryl may optionally be further substiututed by one or more substituents selected from hydroxyl, halogen, and carboxyl.

In one embodiment, $R^4$ represents a straight, branched and/or cyclic $C_{14-16}$alkanoyl, $C_{14-16}$alkenoyl or $C_{14-16}$alkynoyl, all of which may optionally be substituted with one or more substituents selected from hydroxyl, halogen, carboxyl and aryl, wherein said aryl may optionally be further substiututed by one or more substituents selected from hydroxyl, halogen, and carboxyl.

In one embodiment, $R^4$ represents a straight $C_{10-20}$alkanoyl, $C_{14-16}$alkanoyl or $C_{8-17}$alkanoyl.

In one embodiment, $R^4$ represents octanoyl, decanoyl, dodecnoyl, tetradecanoyl, hexadecanoyl, octadecanoyl, 9-carboxy-nonanoyl, 11-carboxy-undecanoyl, 13-carboxy-tridecanoyl, 15-carboxy-pentadecanoyl, 17-carboxy-heptadecanoyl, adamantan-1-yl-acetyl, 4-(hexadecanoyl sulfamoyl)butanoyl, choloyl, lithocholyl or mPEG2000.

In one embodiment, $R^4$ represents a moiety that binds to plasma proteins, such as e.g. albumin. The ability of a compound to bind to albumin may be determined as described in *J. Med. Chem*, 43, 2000, 1986-1992, which is incorporated herein by reference. In the present context, a compound is defined as binding to albumin if Ru/Da is above 0.05, such as above 0.10, such as above 0.12 or even above 0.15.

Particular Compounds of the Present Invention

Particular examples of compounds of formula I include

```
Octanoyl-Nle-c[Glu-His-D-Phe-Arg-Trp-Lys]-NH2,                                          (SEQ ID NO: 56)

Decanoyl-Nle-c[Glu-His-D-Phe-Arg-Trp-Lys]-NH2,                                          (SEQ ID NO: 57)

Tetradecanoyl-Nle-c[Glu-His-D-Phe-Arg-Trp-Lys]-NH2,                                     (SEQ ID NO: 58)

(Adamantan-1-yl)acetyl-Nle-c[Glu-His-D-Phe-Arg-Trp-Lys]-NH2,                            (SEQ ID NO: 59)

Tetradecanoyl-Nle-c[Glu-3-PyAla-D-Phe-Arg-Trp-Lys]-NH2,                                 (SEQ ID NO: 60)

Decanoyl-Nle-c[Glu-3-PyAla-D-Phe-Arg-Trp-Lys]NH2,                                       (SEQ ID NO: 61)

(Adamantan-1yl)acetyl-Nle-c[Glu-3-PyAla-D-Phe-Arg-Trp-Lys]-NH2,                         (SEQ ID NO: 62)

Acetyl-Ser-Lys(3-(dodecanoylamino)propionyl)Ser-Nle-Glu-Ser-D-Phe-Arg-Trp-Gly-Lys-Pro-  (SEQ ID NO: 63)
Val-NH2, Acetyl-Lys(3-(dodecanoylamino)propionyl)-Tyr-Ser-Nle-Glu-Ser-D-Phe-Arg-Trp-Gly-Lys-     (SEQ ID NO: 64)
Pro-Val-NH2, Hexadecanoyl-Ser-Tyr-Ser-Nle-Glu-Ser-D-Phe-Arg-Trp-Gly-Lys-Pro-Val-NH2,                 (SEQ ID NO: 65)

Hexadecanoyl-Ser-Tyr-Ser-Nle-Glu-3-PyAla-D-Phe-Arg-Trp-Gly-Lys-Pro-Val-NH2,             (SEQ ID NO: 66)

2-[2-(Hexadecanoylamino)ethoxy]ethoxyacetyl-Ser-Tyr-Ser-Nle-Glu-3-PyAla-D-Phe-Arg-Trp-  (SEQ ID NO: 67)
Gly-Lys-Pro-Val-NH2, Hexadecanoyl-βAla-Tyr-Ser-Nle-c[Glu-Hyp-D-Phe-Arg-Trp-Lys]-NH2,                         (SEQ ID NO: 68)

Hexadecanoyl-βAla-Ala-Tyr-Ser-Nle-c[Glu-Hyp-D-Phe-Arg-Trp-Lys]-NH2,                     (SEQ ID NO: 69)

Acetyl-Ser-Lys(3-(dodecanoylamino)propionyl)-Ser-Nle-Glu-Hyp-D-Phe-Arg-Trp-Gly-Lys-     (SEQ ID NO: 70)
Pro-Val-NH2, mPEG(2000)acetyl-Nle-c[Glu-Hyp-D-Phe-Arg-Trp-Lys]-NH2,                                  (SEQ ID NO: 71)

2-[2-(Lithocholoylamino)ethoxy]ethoxyacetyl-βAla-Tyr-Ser-Nle-c[Glu-Hyp-D-Phe-Arg-Trp-   (SEQ ID NO: 72)
Lys]-NH2, 2-[2-(15-Carboxypentadecanoylamino)ethoxy]ethoxyacetyl-βAla-Ala-Tyr-Ser-Nle-c[Glu-Hyp-  (SEQ ID NO: 73)
D-Phe-Arg-Trp-Lys]-NH2, Acetyl-Ser-Lys(3-(dodecanoylamino)propionyl)-Ser-Phe-Glu-Hyp-D-Phe-Arg-Trp-Gly-Lys-     (SEQ ID NO: 74)
Pro-Val-NH2,
```

-continued

| | |
|---|---|
| 2-[2-(15-Carboxypentadecanoylamino)ethoxy]ethoxyacetyl-Ser-Gln-Ser-Nle-c[Glu-Hyp-D-Phe-Arg-Trp-Lys]-NH2, | (SEQ ID NO: 75) |
| Hexadecanoyl-Gly-Ser-Gln-His-Ser-Nle-c[Glu-Hyp-D-Phe-Arg-Trp-Lys]-NH2, | (SEQ ID NO: 76) |
| 15-Carboxypentadecanoyl-Gly-Ser-Gln-His-Ser-Nle-c[Glu-Hyp-D-Phe-Arg-Trp-Lys]-NH2, | (SEQ ID NO: 77) |
| 4-(Hexadecanoylsulfamoyl)butanoyl-Gly-Ser-Gln-His-Ser-Nle-c[Glu-Hyp-D-Phe-Arg-Trp-Lys]-NH2, | (SEQ ID NO: 78) |
| 4-[2-(4-Benzoylphenyl)propionylsulfamoyl]butanoyl-Gly-Ser-Gln-His-Ser-Nle-c[Glu-Hyp-D-Phe-Arg-Trp-Lys]-NH2, | (SEQ ID NO: 79) |
| 2-[2-(Octadecanoylamino)ethoxy]ethoxyacetyl-Gly-Ser-Gln-His-Ser-Nle-c[Glu-Hyp-D-Phe-Arg-Trp-Lys]-NH2, | (SEQ ID NO: 80) |
| 2-[2-(Octadecanoylamino)ethoxy]ethoxyacetyl-Nle-c[Glu-Hyp-D-Phe-Arg-Trp-Lys]-NH2, | (SEQ ID NO: 81) |
| Hexadecanoyl-Gly-Ser-Gln-homoArg-Ser-Nle-c[Glu-Hyp-D-Phe-Arg-Trp-Lys]-NH2, | (SEQ ID NO: 82) |
| 2-[2-(15-Carboxypentadecanoylamino)ethoxy]ethoxyacetyl-Nle-c[Glu-Hyp-D-Phe-Arg-Trp-Lys]-NH2, | (SEQ ID NO: 83) |
| Hexadecanoyl-Gly-Ser-Gln-His-Ser-Nle-c[Glu-Met(O2)-D-Phe-Arg-Trp-Lys]-NH2, | (SEQ ID NO: 84) |
| 4-(Hexadecanoylsulfamoyl)butanoyl-Gly-Ser-Gln-Arg-Ser-Nle-c[Glu-Met(O2)-D-Phe-Arg-Trp-Lys]-NH2, | (SEQ ID NO: 85) |
| Hexadecanoyl-Gly-Ser-Gln-homoArg-Ser-Nle-c[Glu-3-pyAla-D-Phe-Arg-Trp-Lys]-NH2, | (SEQ ID NO: 86) |
| Hexadecanoyl-Gly-Ser-Gln-Arg-Ser-Nle-c[Glu-Met(O2)-D-Phe-Arg-Trp-Lys]-NH2, | (SEQ ID NO: 87) |
| 4-(Hexadecanoylsulfamoyl)butanoyl-Gly-Ser-Gln-Arg-Ser-Nle-c[Glu-Gln-D-Phe-Arg-Trp-Lys]-NH2, | (SEQ ID NO: 88) |
| 3-(2-{2-[2-(2-(Hexadecanoylamino)ethoxy)ethoxy]ethoxy}ethoxy)propionyl-Nle-c[Glu-Hyp-D-Phe-Arg-Trp-Lys]-NH2, | (SEQ ID NO: 89) |
| 2-[2-(Hexadecanoylamino)ethoxy]ethoxyacetyl-Gly-Ser-Gln-His-Ser-Nle-c[Glu-Hyp-D-Phe-Arg-Trp-Lys]-NH2, | (SEQ ID NO: 90) |
| 2-[2-(Tetradecanoylamino)ethoxy]ethoxyacetyl-Gly-Ser-Gln-His-Ser-Nle-c[Glu-Hyp-D-Phe-Arg-Trp-Lys]-NH2, | (SEQ ID NO: 91) |
| Hexadecanoyl-Gly-Thr-Gln-His-Ser-Nle-c[Glu-Hyp-D-Phe-Arg-Trp-Lys]-NH2, | (SEQ ID NO: 92) |
| Hexadecanoyl-Gly-Gln-Gln-His-Ser-Nle-c[Glu-Hyp-D-Phe-Arg-Trp-Lys]-NH2, | (SEQ ID NO: 93) |
| Hexadecanoyl-Gly-Thr-Gln-His-Ser-Nle-c[Glu-Asn-D-Phe-Arg-Trp-Lys]-NH2, | (SEQ ID NO: 94) |
| Hexadecanoyl-Gly-Glu-Thr-Gln-His-Ser-Nle-c[Glu-Hyp-D-Phe-Arg-Trp-Lys]-NH2, | (SEQ ID NO: 95) |
| Hexadecanoyl-Glu-Gly-Thr-Gln-His-Ser-Nle-c[Glu-Hyp-D-Phe-Arg-Trp-Lys]-NH2, | (SEQ ID NO: 96) |
| Hexadecanoyl-Glu-4-Abu-Thr-Gln-His-Ser-Nle-c[Glu-Hyp-D-Phe-Arg-Trp-Lys]-NH2, | (SEQ ID NO: 97) |
| 2-[2-(Hexadecanoylamino)ethoxy]ethoxyacetyl-His-Ser-Nle-c[Glu-Hyp-D-Phe-Arg-Trp-Lys]-NH2, | (SEQ ID NO: 98) |
| 2-[2-(Hexadecanoylamino)ethoxy]ethoxyacetyl-Arg-Ser-Nle-c[Glu-Hyp-D-Phe-Arg-Trp-Lys]-NH2, | (SEQ ID NO: 99) |
| 2-[2-(Hexadecanoylamino)ethoxy]ethoxyacetyl-Gln-Ser-Nle-c[Glu-Hyp-D-Phe-Arg-Trp-Lys]-NH2, | (SEQ ID NO: 100) |
| 2-[2-(Hexadecanoylamino)ethoxy]ethoxyacetyl-Glu-Ser-Nle-c[Glu-Hyp-D-Phe-Arg-Trp-Lys]-NH2, | (SEQ ID NO: 101) |
| 2-[2-(2-{2-[2-(Dodecanoylamino)ethoxy]ethoxy}acetylamino)ethoxy]ethoxyacetyl-Nle-c[Glu-Hyp-D-Phe-Arg-Trp-Lys]-NH2, | (SEQ ID NO: 102) |
| 2-{2-[4-Carbamoyl-2-(2-(hexadecanoylamino)acetylamino)butyrylamino]ethoxy}ethoxyacetyl-Nle-c[Glu-Hyp-D-Phe-Arg-Trp-Lys]-NH2, | (SEQ ID NO: 103) |
| 2-{2-[4-Carboxy-2-(2-hexadecanoylamino)acetylamino)butyrylamino]ethoxy}ethoxyacetyl-Nle-c[Glu-Hyp-D-Phe-Arg-Trp-Lys]-NH2, | (SEQ ID NO: 104) |
| 2-{2-[2-(2-(Hexadecanoylamino)acetylamino)-3-(imidazol-4-yl)propionylamino]ethoxy}ethoxyacteyl-Nle-c[Glu-Hyp-D-Phe-Arg-Trp-Lys]-NH2, | (SEQ ID NO: 105) |

-continued

| | |
|---|---|
| Dodecanoyl-Nle-c[Glu-Hyp-D-Phe-Arg-Trp-Lys]-NH2, | (SEQ ID NO: 106) |
| Hexadecanoyl-Gly-Thr-Asn-Asn-Thr-Nle-c[Glu-Hyp-D-Phe-Arg-Trp-Lys]-NH2, | (SEQ ID NO: 107) |
| Octanoyl-Gly-Ser-D-Gln-His-Thr-Nle-c[Glu-Hyp-D-Phe-Arg-Trp-Lys]-NH2, | (SEQ ID NO: 108) |
| Decanoyl-Gly-Ser-D-Gln-His-Thr-Nle-c[Glu-Hyp-D-Phe-Arg-Trp-Lys]-NH2, | (SEQ ID NO: 109) |
| Dodecanoyl-Gly-Ser-D-Gln-His-Thr-Nle-c[Glu-Hyp-D-Phe-Arg-Trp-Lys]-NH2, | (SEQ ID NO: 110) |
| Tetradecanoyl-Gly-Ser-D-Gln-His-Thr-Nle-c[Glu-Hyp-D-Phe-Arg-Trp-Lys]-NH2, | (SEQ ID NO: 111) |
| Hexadecanoyl-Gly-Ser-D-Gln-His-Thr-Nle-c[Glu-Hyp-D-Phe-Arg-Trp-Lys]-NH2, | (SEQ ID NO: 112) |
| Octadecanoyl-Gly-Ser-D-Gln-His-Nle-c[Glu-Hyp-D-Phe-Arg-Trp-Lys]-NH2, | (SEQ ID NO: 113) |
| Hexadecanoyl-Gly-Ser-Gln-His-Ser-Nle-c[Glu-F-Pro-D-Phe-Arg-Trp-Lys]-NH2, | (SEQ ID NO: 114) |
| Hexadecanoyl-Gly-Ser-Gln-homoArg-Ser-Nle-c[Glu-F-Pro-D-Phe-Arg-Trp-Lys]-NH2, | (SEQ ID NO: 115) |
| Hexadecanoyl-Gly-Ser-Gln-homoArg-Thr-Nle-c[Glu-F-Pro-D-Phe-Arg-Trp-Lys]-NH2, | (SEQ ID NO: 116) |
| Hexadecanoyl-Gly-Ser-Asn-homoArg-Thr-Ser-Nle-c[Glu-F-Pro-D-Phe-Arg-Trp-Lys]-NH2, | (SEQ ID NO: 117) |
| 3-{2-[2-(2-{2-[4-(4,4,5,5,6,6,7,7,8,8,9,9,9-Tridecafluorononanoylsulfamoyl)butyrylamino]-ethoxy}ethoxy)ethoxy]ethoxy}propionyl-Gly-Ser-Gln-homoArg-Nle-c[Glu-Hyp-D-Phe-Arg-Trp-Lys]-NH2, | (SEQ ID NO: 118) |
| Hexadecanoyl-Gly-Ser-Ser-Tyr-Thr-Nle-c[Glu-Hyp-D-Phe-Arg-Trp-Lys]-NH2, | (SEQ ID NO: 119) |
| Hexadecanoyl-Gly-Ser-Asn-Asn-Thr-Nle-c[Glu-Hyp-D-Phe-Arg-Trp-Lys]-NH2, | (SEQ ID NO: 120) |
| Hexadecanoyl-Gly-Ser-Ser-homoArg-Thr-Nle-c[Glu-Hyp-D-Phe-Arg-Trp-Lys]-NH2, | (SEQ ID NO: 121) |
| Hexadecanoyl-Gly-Ser-Ser-His-Thr-Nle-c[Glu-Hyp-D-Phe-Arg-Trp-Lys]-NH2, | (SEQ ID NO: 122) |
| Hexadecanoyl-Gly-Ser-D-Asn-His-Thr-Nle-c[Glu-Hyp-D-Phe-Arg-Trp-Lys]-NH2, | (SEQ ID NO: 123) |
| Hexadecanoyl-Gly-Ser-Asn-homoArg-Thr-Nle-c[Glu-Hyp-D-Phe-Arg-Trp-Lys]-NH2, | (SEQ ID NO: 124) |
| Hexadecanoyl-Ser-homoArg-Ser-Nle-c[Glu-Met(O2)-D-Phe-Arg-Trp-Lys]-NH2, | (SEQ ID NO: 125) |
| Hexadecanoyl-Gln-homoArg-Thr-Nle-c[Glu-Met(O2)-D-Phe-Arg-Trp-Lys]-NH2, | (SEQ ID NO: 126) |
| Hexadecanoyl-Ser-homoArg-Thr-Nle-c[Glu-Met(O2)-D-Phe-Arg-Trp-Lys]-NH2, | (SEQ ID NO: 127) |
| Hexadecanoyl-Ser-His-Thr-Nle-c[Glu-Met(O2)-D-Phe-Arg-Trp-Lys]-NH2, and | (SEQ ID NO: 128) |
| Hexadecanoyl-Ser-homoArg-Thr-Nle-c[Glu-Met(O2)-D-Phe-Arg-Trp-Lys]-NH2. | (SEQ ID NO: 129) |

Other embodiments of the invention are clear from the claims.

In one embodiment of the present invention, the compound is an agonist of a melanocortin receptor.

In one embodiment of the present invention, the compound is an agonist of MC-4.

In one embodiment of the present invention, the compound is a selective agonist of MC-4. In this context, selectivity is to be understood in relation to the activity of the compound with respect to MC1, MC3 and/or MC5. If a compound is a significantly more potent MC4 agonist than it is a potent MC1, MC3 and/or MC5 agonist, it is deemed to be a selective MC4 agonist. The potencies of a compound with respect to MC1 and MC4 are determined in receptor binding assays as described in assay IV (MC 1) and assay V (MC4). If a compound is more than 10 times, such as more than 50 times, such as more than 100 times more potent with respect to MC4 than with respect to MC1, it is deemed to be a selective MC4 agonist with respect to MC1. The potencies of a compound with respect to MC3, MC4 and MC5 are determined in functional assays as described in assay II (MC 3 and MC5) and assay III (MC4). If a compound is more than 10 times, such as more than 50 times, such as more than 100 times more potent with respect to MC4 than with respect to MC3, it is deemed to be a selective MC4 agonist with respect to MC3. If a compound is more than 10 times, such as more than 50 times, such as more than 100 times more potent with respect to MC4 than with respect to MC5, it is deemed to be a selective MC4 agonist with respect to MC5. In a particular embodiment, the compound of the present invention is a selective MC4 agonist with respect to MC1, with respect to MC3, with respect to MC5, with respect to MC1 and MC3, with respect to MC1 and MC5, with respect to MC3 and MC5 or with respect to MC1, MC3 and MC5.

In one embodiment, the compound of the present invention is a selective MC4 agonists and a MC3 antagonist. in this context, a compound is deemed to be a selective MC4 agonist and a MC3 antagonist if it is a selective MC4 agonist with respect to MC1 and MC5 as discussed above, and it antagonizes MC 3 measured as described in assay II. A compound with an $IC_{50}$ value less than 100 nM, such as less than 10 nM, such as less than 5 nM, such as less than 1 nM is deem to be a MC3 antagonist.

In one embodiment, the compound of the present invention is both a selective MC3 agonist and a selective MC4 agonist. In this context, a compound is deemed to be a selective MC3 and MC4 agonist if it is significantly more potent MC3 and MC4 agonist than it is a potent MC1 and MC5 agonist. The selectivity of a compound with respect to MC1 and MC3 are determined by comparing the potency determined for MC1 as described in assay IV with the potency for MC3 determined as described in assay II. If a compound is more than 10 times, such as more than 50 times, such as more than 100 times more potent with respect to MC3 than with respect to MC1 it is deemed to be a selective MC3 agonist with respect to MC1. The selectivity of compound with respect to MC3 and MC5 are determined by comparing the potency determined as described in assay II. If a compound is more than 10 times, such as more the 50 times, such as more than 100 times more potent with respect to MC3 than with respect to MC5 it is deemed to a selective MC3 agonist with respect to MC5 receptor. The MC4 selectivity of a compound with respect to MC3 and MC5 is determined as discussed above.

Compounds of the present invention modulate melanocortine receptors, and they are therefore believed to be particular suited for the treatment of diseases or states which benefit from a modulation of the melanocortine receptor activity. In particular, compounds of the present invention are believed to be suited for the treatment of diseases or states which benefit from an activation of the MC-4 receptor.

In one embodiment, the present invention provides a method of delaying the progression from impaired glucose tolerance (IGT) to type 2 diabetes, the method comprising administering to a patient in need thereof an effective amount of a compound of the present invention.

In one embodiment, the present invention provides a method of delaying the progression from type 2 diabetes to insulin requiring diabetes, the method comprising administering to a patient in need thereof an effective amount of a compound of the present invention.

In one embodiment, the invention relates to a method of treating obesity or preventing overweight, the method comprising administering to a patient in need thereof an effective amount of a compound of the present invention.

In one embodiment, the present invention provides a method of regulating the appetite, the method comprising administering to a patient in need thereof an effective amount of a compound of the present invention.

In one embodiment, the present invention relates to a method of inducing satiety, the method comprising administering to a patient in need thereof an effective amount of a compound of the present invention.

In one embodiment, the invention relates to a method of preventing weight regain after successfully having lost weight.

In one embodiment, the invention relates to a method of increasing energy expenditure.

In one embodiment, the present invention provides a method of treating a disease or state related to overweight or obesity, the method comprising administering to a patient in need thereof an effective amount of a compound of the present invention.

In one embodiment, the invention relates to a method of treating bulimia, the method comprising administering to a patient in need thereof an effective amount of a compound of the present invention.

In one embodiment, the invention relates to a method of treating a disease or state selected from atherosclerosis, hypertension, diabetes, type 2 diabetes, impaired glucose tolerance (IGT), dyspilidemia, coronary heart disease, gallbladder disease, gall stone, osteoarthritis, cancer, sexual dysfunction and the risk of premature death, the method comprising administering to a patient in need thereof an effective amount of a compound of the present invention.

In particular, compounds of the present invention may be suited for the treatment of diseases in obese or overweight patients. Accordingly, the present invention also provides a method of treating in obese patients diseases or states selected from amongst type 2 diabetes, impaired glucose tolerance (IGT), dyspilidemia, coronary heart disease, gallbladder disease, gall stone, osteoarthritis, cancer, sexual dysfunction and the risk of premature death in obese patients, the method comprising administering to a patient in need thereof an effective amount of a compound of the present invention.

In addition, MC4 receptor agonist could have a positive effect on insulin sensitivity, drug abuse by modulating the reward system and haemorhegic shock. Furthermore, MC3 and MC4 receptor agonists have antipyretic effects and both have been suggested to be involved in peripheral nerve regeneration and the MC4 receptor is also known to reduce stress response.

In all therapeutic method disclosed above, the compound of the present invention may be administered alone. However, it may also be administered in combination with one or more additional therapeutically active compound, either sequentially or concomitantly.

In one aspect, the invention relates to a pharmaceutical composition comprising a compound of the present invention, optionally in combination with one or more additional therapeutically active compound together with one or more pharmaceutically acceptable carrier or exipient in unit dosage form comprising about 0.05 mg to about 1000 mg, such as about 0.1 mg to about 500 mg, such as from about 0.5 mg to about 200 mg of a compound of the present invention.

The present invention also relates to the use of a compound of the present invention in the manufacture of a medicament for the treatment a diseases or states selected from overweight or obesity, bulimia, atherosclerosis, hypertension, type 2 diabetes, impaired glucose tolerance (IGT), dyspilidemia, coronary heart disease, gallbladder disease, gall stone, osteoarthritis, cancer, sexual dysfunction and the risk of premature death.

The present invention also relates to the use of a compound of the present invention, alone or in combination with an additional therapeutically active compound, in the manufacture of a medicament effective in delaying the progression from IGT to type 2 diabetes, delaying the progression from type 2 diabetes to insulin requiring diabetes, regulating the appetite, inducing satiety, preventing weight gain after successfully having lost weight or increasing energy expenditure.

As described above, compounds of the present invention may be administered or applied in combination with one or more additional therapeutically active compound. Suitable additional compounds may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells e.g. potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, glucokinase activators, such as those described in WO 02/08209 to Hoffmann La Roche, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

Other examples of suitable additional therapeutically active compounds include insulin or insulin analogues, sulfonylurea e.g. tolbutamide, chlorpropamide, tolazamide, glibenclamide, glipizide, glimepiride, glicazide, glyburide, biguanide e.g. metformin, meglitinide e.g. repaglinide or senaglinide/nateglinide.

Other examples of suitable additional therapeutically active compounds include thiazolidinedione insulin sensitizers e.g. troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

Other examples of suitable additional therapeutically active compounds include insulin sensitizers e.g. such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

Other examples of suitable additional therapeutically active compounds include α-glucosidase inhibitor e.g. voglibose, emiglitate, miglitol or acarbose.

Other examples of suitable additional therapeutically active compounds include glycogen phosphorylase inhibitor e.g. the compounds described in WO 97/09040 (Novo Nordisk A/S).

Other examples of suitable additional therapeutically active compounds include a glucokinase activator.

Other examples of suitable additional therapeutically active compounds include an agent acting on the ATP-dependent potassium channel of the pancreatic β-cells e.g. tolbutamide, glibenclamide, glipizide, glicazide, BTS-67582 or repaglinide.

Other examples of suitable additional therapeutically active compounds include nateglinide.

Other examples of suitable additional therapeutically active compounds include an antihyperlipidemic agent or a antilipidemic agent e.g. cholestyramine, colestipol, clofibrate, gemfibrozil, lovastatin, pravastatin, simvastatin, probucol or dextrothyroxine.

Other examples of said additional therapeutically active compounds include antiobesity compounds or appetite regulating agents. Such compounds may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, chemical uncouplers, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists and ciliary neurotrophic factor. Further antiobesity agents are bupropion (antidepressant), topiramate (anticonvulsant), ecopipam (dopamine D1/D5 antagonist), naltrexone (opioid antagonist), and peptide $YY_{3-36}$ (Batterham et al, Nature 418, 650-654 (2002)).

In one embodiment, the antiobesity agent is leptin.

In one embodiment, the antiobesity agent is peptide $YY_{3-36}$.

In one embodiment, the antiobesity agent is a serotonin and norepinephrine reuptake inhibitor e.g. sibutramine.

In one embodiment, the antiobesity agent is a lipase inhibitor e.g. orlistat.

In one embodiment, the antiobesity agent is an adrenergic CNS stimulating agent e.g. dexamphetamine, amphetamine, phentermine, mazindol phendimetrazine, diethylpropion, fenfluramine or dexfenfluramine.

Other examples of suitable additional therapeutically active compounds include antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin.

In one embodiment of the uses and methods of the present invention, the compound of the present invnetion may be administered or applied in combination with more than one of the above-mentioned compounds e.g. in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Pharmaceutical Compositions

The compounds for use according to the present invention may be administered alone or in combination with pharmaceutically acceptable carriers or excipients, in either single or multiple doses. The pharmaceutical compositions according to the present invention may be formulated with pharmaceutically acceptable carriers or diluents as well as any other known adjuvants and excipients in accordance with conventional techniques such as those disclosed in Remington: The Science and Practice of Pharmacy, 20$^{th}$ Edition, Gennaro, Ed., Mack Publishing Co., Easton, Pa., 2000.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the parenteral and sublingual routes being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds for use according to the present invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds for use according to the present invention which are generally prepared by reacting the free base with a suitable organic or inorganic acid or by reacting the acid with a suitable organic or inorganic base. When a compound for use according to the present invention, such as a compound of Formula (I), contains a free base such salts are prepared in a conventional manner by treating a solution or suspension of the compound with a chemical equivalent of a pharmaceutically acceptable acid. When a compounds for use according to the present invention, such as a compound of Formula (I), contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds for use according to the present invention and these form a further aspect of the present invention.

For parenteral administration, solutions of the compounds for use according to the present invention in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl mono-stearate or glyceryl distearate, alone or mixed with a wax. The pharmaceutical compositions formed by combining the compounds for use according to the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsule wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds for use according to the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds for use according to the present invention may form solvates with water or common organic solvents. Such solvates are also encompassed within the scope of the present invention.

Thus, in a further embodiment, there is provided a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

EXAMPLES

All compounds of the present can be synthesized by those skilled in the art using standard coupling and deprotection steps. A description of all necessary tools and synthetic methods can be found in "The Fine Art Of Solid Phase Synthesis", 2002/3 Catalog, Novabiochem.

Typical examples which include a cyclization step are as follows:

Example A

Dodecanoyl-Nle-c[Glu-Hyp-D-Phe-Arg-Trp-Lys]-NH$_2$

The protected peptidyl resin H-Nle-Glu(2-phenylisopropyloxy)-Hyp(tBu)-D-Phe-Arg(Pmc)-Trp(Boc)-Lys(Mtt)-(Rink resin) was synthesized according to the Fmoc strategy on an Applied Biosystems 431A peptide synthesizer on a 0.25 mmol scale using the manufacturer-supplied "FastMoc UV" protocols which employ HBTU (2-(1H-Benzotriazol-1-yl-)-1,1,3,3 tetramethyluronium hexafluorophosphate) mediated couplings in NMP (N-methyl pyrrolidone) and UV monitoring of the deprotection of the Fmoc protection group. The starting resin used for the synthesis was 0.50 g (4-((2',4'-dimethoxyphenyl)-(Fmoc-amino)methyl)-phenoxypolystyrene resin (Rink resin) (Novabiochem) with a loading of 0.51 mmol/g. The protected amino acid derivatives used were Fmoc-Lys(Mtt)-OH, Fmoc-Trp(Boc)-OH, Fmoc-Arg(Pmc)-OH, Fmoc-D-Phe-OH, Fmoc-Hyp(tBu)-OH, Fmoc-Glu(2-phenylisopropyloxy)-OH and Fmoc-Nle-OH.

1.b Then the peptide resin resulting from (1.a) was acylated with a preactivated solution of dodecanoic acid (1.0 mmol), HODhbt (3,4-dihydro-3-hydroxy-4-oxo-1,2,3-benzotriazine) (1.0 mmol), DIC (diisopropyl carbodiimide) (1.0 mmol) and DIEA (N,N-diisopropylethylamine) (0.25 mmol) in NMP (5 ml). After 2 hours at room temperature, the resin was filtered and washed with NMP and dichloromethane (DCM).

1.c The resin resulting from (1.b) was treated with 5×10 ml 2% trifluoroacetic acid (TFA), 2% triethylsilane (TES) in DCM during 60 minutes with regular mixing. The resin was washed with NMP, NMP with 5% DIEA and NMP. The peptide was cyclized using HODhbt (1.0 mmol), (benzotriazol-1-yloxy)tripyrrolidinophosphonium hexafluorophosphate 1H-benzotriazol-1-yloxytripyrrolidinophosphonium hexafluorophosphate (PyBOP) (1.0 mmol) and DIEA (2.0 mmol) in NMP (5 ml) with regular mixing for 4 h. The resin was washed with NMP and DCM.

1.d The peptide was cleaved from the resin obtained from (1.c) by stirring for 60 minutes at room temperature with 10 ml of 2.5% water and 2.5% TES in TFA. The cleavage mixture was filtered and the filtrate was concentrated to approximately 1 ml by a stream of nitrogen. The crude peptide was precipitated from this oil with 50 ml diethyl ether and washed 3 times with 50 ml diethyl ether.

The crude cyclic peptide was purified by preparative RP-HPLC. For analytical data of the purified peptide, see example 51 listed below.

Example B

Protected Peptide Resin Fmoc-Nle-c[Glu-Hyp(tBu)-D-Phe-Arg(Pbf)-Trp-Lys]-NH-Rink Linker-Polystyrene Fmoc-Rink resin (4-(2',4'-dimethoxyphenyl-Fmoc-aminomethyl)-phenoxypolystyrene resin, Novabiochem 01-64-0013; 0.47 mmol/g) was filled into three 60 ml Teflon reactors with frit (per reactor: 3.55 g, 1.667 mmol; totally: 10.65 g, 5.0 mmol). The resin in each reactor was washed with 25 ml DCM.

Removal of Fmoc: The resin was shaken with a solution of 20% piperidine in NMP (25 ml) for 20 min and then washed with NMP/DCM 1:1 (5×30 ml).

Acylation with Fmoc-Lys(Mtt)-OH: In a separate glass vial, the Fmoc-amino acid (15.0 mmol) was mixed with NMP (18.8 ml), DCM (33.8 ml) and a 1 M solution (15.0 ml, 15.0 mmol) of 1-hydroxybenzotriazol (HOBt) in NMP. To the resulting clear solution, DIC (2.34 ml, 15.0 mmol) was quickly added and the solution was shaken immediately thereafter. The solution was left to stand in a closed vial for 40 min. 25 ml (5.0 mmol HOBt ester) of this solution was added to each reactor and the resin was shaken for 90 min. DIEA (0.856 ml, 5.0 mmol) was added and the mixture was shaken for 17 h. The resin was washed with NMP/DCM 1:1 (4×30 ml).

Removal of Fmoc: As described above

Acylation with Fmoc-Trp(Boc)-OH: In a separate glass vial, the Fmoc-amino acid (15.0 mmol) was mixed with NMP (18.8 ml), DCM (33.8 ml) and 1M HOBt-NMP solution (15.0 ml, 15.0 mmol). To the resulting clear solution, DIC (2.34 ml, 15.0 mmol) was quickly added and the solution was shaken immediately thereafter. The solution was left to stand in a closed vial for 50 min. 25 ml (5.0 mmol HOBt ester) of this solution was added to each reactor and the resin was shaken for 2 h. The liquids were filtered off and the resin was washed with NMP/DCM 1:1 (4×30 ml).

In a similar manner, the following amino acids were successively attached to the resin: Fmoc-Arg(Pbf)-OH, Fmoc-D-Phe-OH, Fmoc-Hyp(tBu)-OH, Fmoc-Glu(2-phenylisopropyloxy)-OH, and Fmoc-Nle-OH. The resulting Fmoc-protected resin was extensively washed with DCM.

Selective side-chain deprotection of Lys and Glu: The resin was shaken with a solution of 2% TFA and 2% triisopropylsilane in DCM (25 ml) for 10 min and the liquid was filtered off. This procedure was repeated another seven times. The resin was washed with DCM (2×20 ml), 2% DIEA in DCM (2×25 ml), 5% DIEA in DCM (25 ml) and DCM (2×25 ml).

Side-chain cyclisation of Lys with Glu: In a separate glass vial, PyBOP (7.808 g=15.0 mmol) was mixed with 1 M HOBt-NMP solution (15.0 ml=15.0 mmol), DCM (37.5 ml) and NMP (22.5 ml). 25 ml (containing 5.0 mmol PyBOP/HOBt) of this solution was added to each reactor, followed by DIEA (1.712 ml=10.0 mmol). The resin was shaken for 13 h. The liquids were filtered off and the resin was washed with NMP/DCM 1:1 (2×30 ml), DCM/MeOH 1:1 (30 ml) and DCM (5×30 ml).

The resin was stored in a vacuum desiccator for one day. This afforded 21.61 g of resin corresponding to a supposed maximum loading of 0.23 mmol/g, if complete reactions are assumed.

Example C

Hexadecanoyl-Gly-Ser-Gln-His-Ser-Nle-c[Glu-Hyp-D-Phe-Arg-Trp-Lys]-NH$_2$

A 60 ml Teflon reactor with frit was charged with resin Fmoc-Nle-cyclo[Glu-Hyp(tBu)-D-Phe-Arg(Pbf)-Trp-Lys]-NH-Rink linker-polystyrene (1.739 g, approximately 0.40 mmol, Example B). The resin was washed with DCM (12 ml).

Removal of Fmoc: The resin was shaken with a solution of 20% piperidine in NMP (9 ml) for 20 min and then washed with NMP/DCM 1:1 (5×12 ml).

Acylation with Fmoc-Ser(tBu)-OH: In a separate glass vial, the Fmoc-amino acid (1.8 mmol) was mixed with NMP (2.25 ml), DCM (4.1 ml) and 1M HOBt-NMP solution (1.8 ml, 1.8 mmol). To the resulting clear solution, DIC (0.280 ml, 1.8 mmol) was quickly added and the solution was shaken immediately thereafter. The solution was left to stand in a closed vial for 1 h and then added to the resin. The mixture was shaken for 2 h. The liquids were filtered off and the resin was washed with NMP/DCM 1:1 (4×12 ml).

In a similar manner, the following amino acids were successively attached to the resin: Fmoc-His(Trt)-OH, Fmoc-Gln(Trt)-OH, Fmoc-Ser(tBu)-OH, and Fmoc-Gly-OH. The N-terminal Fmoc group was removed as described above.

Acylation with hexadecanoic acid: In a separate glass vial, the carboxylic acid (1.8 mmol) was mixed with NMP (2.25 ml), DCM (4.1 ml) and 1M HOBt-NMP solution (1.8 ml, 1.8 mmol). To the resulting clear solution, DIC (0.280 ml, 1.8 mmol) was quickly added and the solution was shaken immediately thereafter. The solution was left to stand in a closed vial for 25 min and then added to the resin. The mixture was shaken for 40 min. DIEA (0.308 ml, 1.8 mmol) was added and the mixture was shaken for 3 h. The liquids were filtered off and the resin was washed with (each washing with 12 ml of solvent) 2×NMP/DCM 1:1, 2×DCM/MeOH 2:1, 2×THF and 2×DCM.

Cleavage from the resin: The resin was shaken with a premixed solution prepared from TFA (11.5 ml), triisopropylsilane (0.3 ml) and water (0.3 ml) for 1 h and 40 min. The filtrate was collected in a 100 ml round-bottom flask. The resin was washed with 3×8 ml DCM/TFA 2:1 and the filtrates were collected. The combined filtrate solution was concentrated under reduced pressure to give a red oil.

Precipitation with ether: The oily residue was treated with diethylether (40 ml) to give a solid precipitate. The ether phase was removed after centrifugation. The solid residue was washed again with diethylether (40 ml). After centrifugation and removal of the ether phase, the solid residue was left to stand overnight in order to remove ether remains.

Purification: The crude product precipitated from ether was dissolved in a mixture of acetonitrile (5.3 ml), acetic acid (0.5 ml) and water to give a total volume of about 21 ml. The resulting dim liquid was filtered and then injected into a Gilson preparative HPLC device. Elution was performed with water/acetonitrile containing 0.1% TFA with a gradient from 35% to 50% acetonitrile. The eluate was collected as fractions of 5 ml. Relevant fractions were checked by analytical HPLC. Fractions containing the pure target peptide were mixed and concentrated under reduced pressure to give a colourless emulsion (approx. 8 ml). This was mixed with acetonitrile (4 ml), 1M aqueous HCl (0.6 ml) and de-ionised water to give a total volume of 41 ml. The resulting clear solution was dispensed into glass vials. The vials were capped with Millipore glass fibre prefilters. Freeze-drying for three days afforded the peptide hydrochloride (99.4 mg, 14% yield) as a white solid.

HPLC (Waters Symmetry C18, 5 μm, 3.0×150 mm; water/acetonitrile containing 0.05% TFA; gradient: 5%→90% acetonitrile from 0 to 15 min): $t_R$=11.71 min (100% purity by UV 214 and 254 nm)

For LC/MS data of the purified peptide, see example 21 listed below.

In the examples listed below, Rt values are retention times and the mass values are those detected by the MS detector obtained by using one of the following LC/MS devices.

LC/MS system 1: Agilent 1100 Series, electrospray; column: Waters XTerra® $C_{18}$ 5 μm 3.0×50 mm; water/acetonitrile containing 0.05% TFA; gradient: 5%→100% acetonitrile from 0 to 6.75 min, elution until t=9.0 min; flow 1.5 ml/min LC/MS system 2: Sciex API-100 Quadrupole MS, electrospray; column: Waters XTerra® $C_{18}$ 5 μm 3.0×50 mm; water/acetonitrile containing 0.05% TFA; gradient: 5%→90% acetonitrile from 0 to 7.5 min, elution until t=10.0 min; flow 1.5 ml/min LC/MS system 3: Sciex API-150 Ex Quadrupole MS, electrospray; column: Waters XTerra® $C_{18}$ 5 μm 3.0×50 mm; water/acetonitrile containing 0.05% TFA; gradient: 5%→15% acetonitrile from 1.0 to 2.0 min, 15%→45% acetonitrile from 2.0 to 28.0 min, 45%→90% acetonitrile from 28.0 to 30.0 min, elution until t=30.0 min; flow 1.5 ml/min LC/MS system 4: as described for system 3, but with another gradient: 5%→20% acetonitrile from 1.0 to 3.0 min, 20%→50% acetonitrile from 3.0 to 16.0 min, 50%→90% acetonitrile from 16.0 to 18.0 min, elution until t=18.0 min Example 1

Octanoyl-Nle-c[Glu-His-D-Phe-Arg-Trp-Lys]-NH2

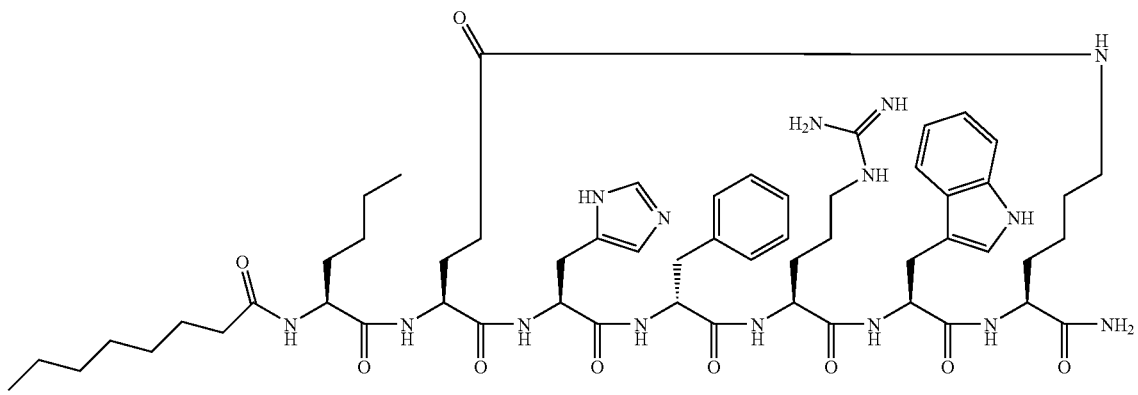

LC/MS (system 1): Rt=3.81 min; (m+1)=1123

Example 2
Decanoyl-Nle-c[Glu-His-D-Phe-Arg-Trp-Lys]-NH2
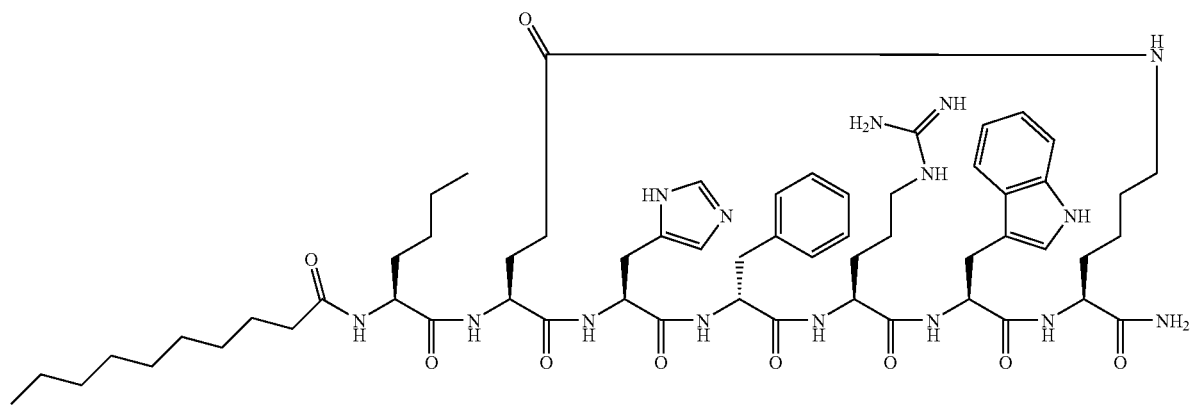
LC/MS (system 1): Rt=4.20 min; (m+1)=1151
Example 3
Tetradecanoyl-Nle-c[Glu-His-D-Phe-Arg-Trp-Lys]-NH2
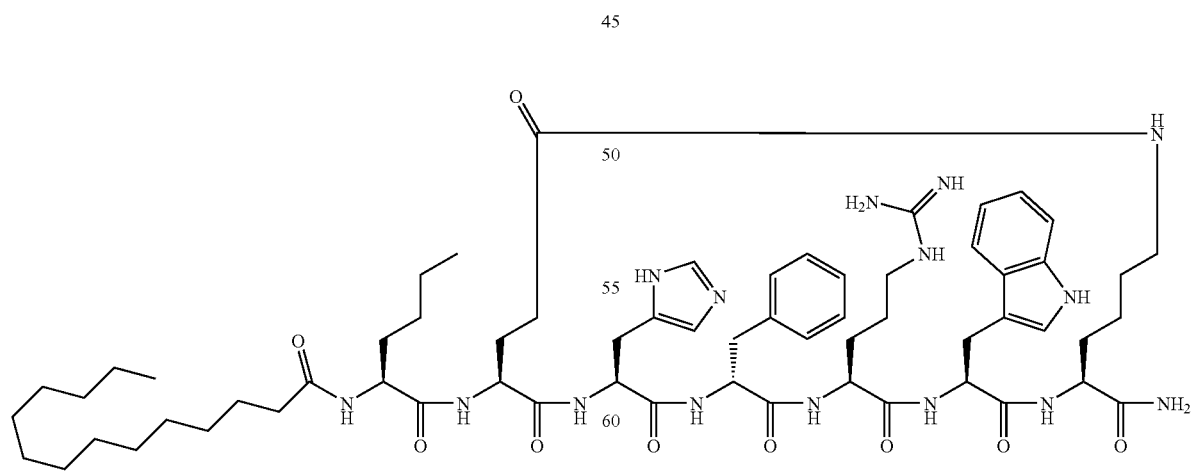

Example 4
(Adamantan-1-yl)acetyl-Nle-c[Glu-His-D-Phe-Arg-Trp-Lys]-NH2
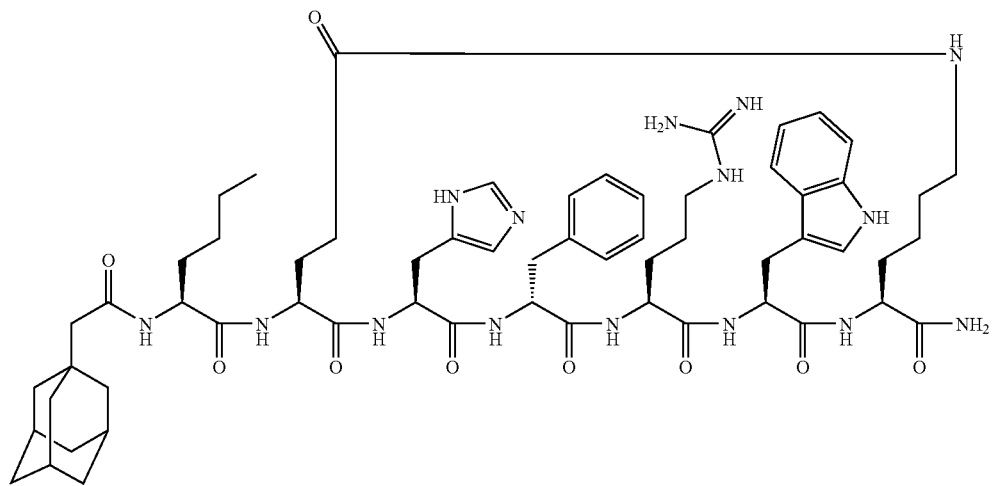
LC/MS (system 1): Rt=3.88; (m+1)=1173
Example 5
Tetradecanoyl-Nle-c[Glu-3-PyAla-D-Phe-Arg-Trp-Lys]-NH2
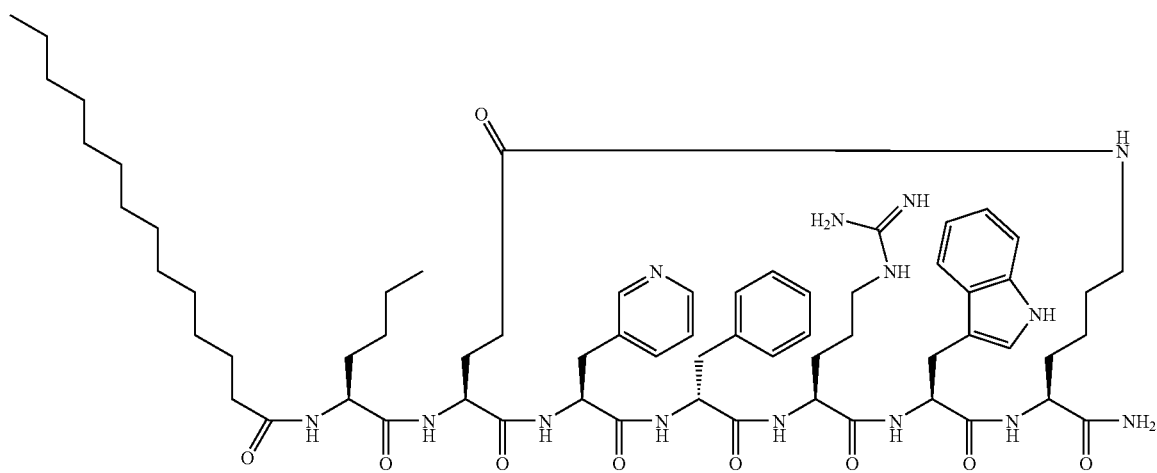
LC/MS (system 2): Rt=7.32 min; (m+1)=1218

Example 6
Decanoyl-Nle-c[Glu-3-PyAla-D-Phe-Arg-Trp-Lys]-NH2
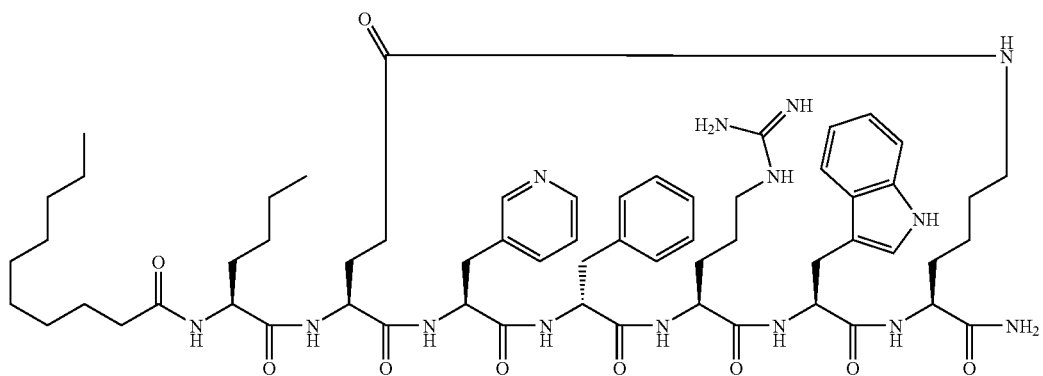
LC/MS (system 2): Rt=7.00 min; (m+1)=1162
Example 7
(Adamantan-1yl)acetyl-Nle-c[Glu-3-PyAla-D-Phe-Arg-Trp-Lys]-NH2
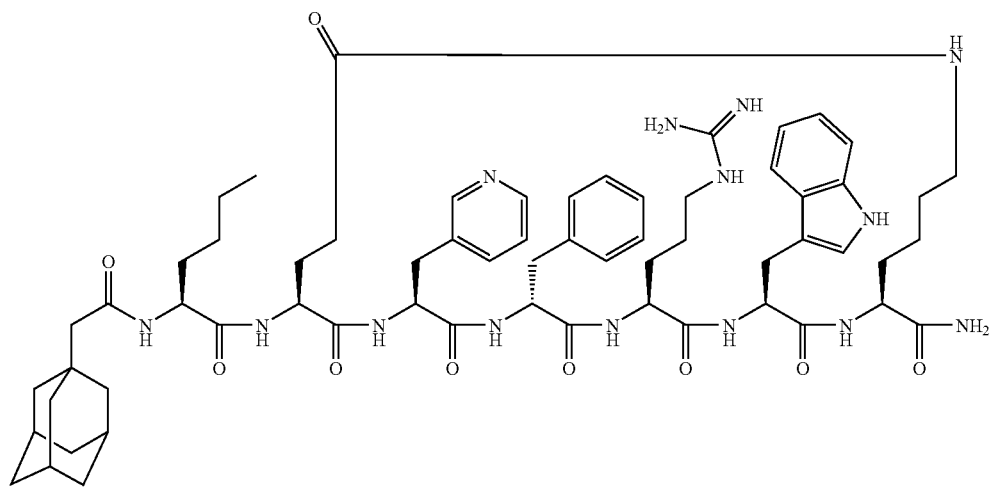
LC/MS (system 2): Rt=7.00 min; (m+1)=1184
Example 8
Acetyl-Ser-Lys(3-(dodecanoylamino)propionyl)-Ser-Nle-Glu-Ser-D-Phe-Arg-Trp-Gly-Lys-Pro-Val-NH2

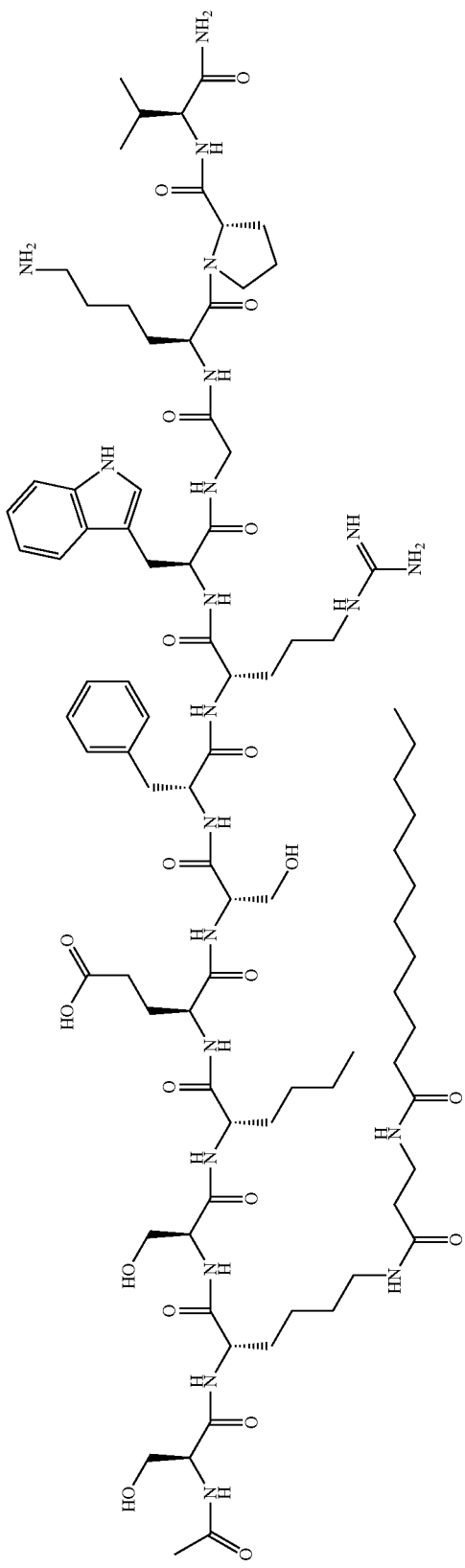

LC/MS (system 1): Rt=3.43 min; ((m+2)/2)=908
Example 9
Acetyl-Lys(3-(dodecanoylamino)propionyl)-Tyr-Ser-Nle-Glu-Ser-D-Phe-Arg-Trp-Gly-Lys-Pro-Val-NH2
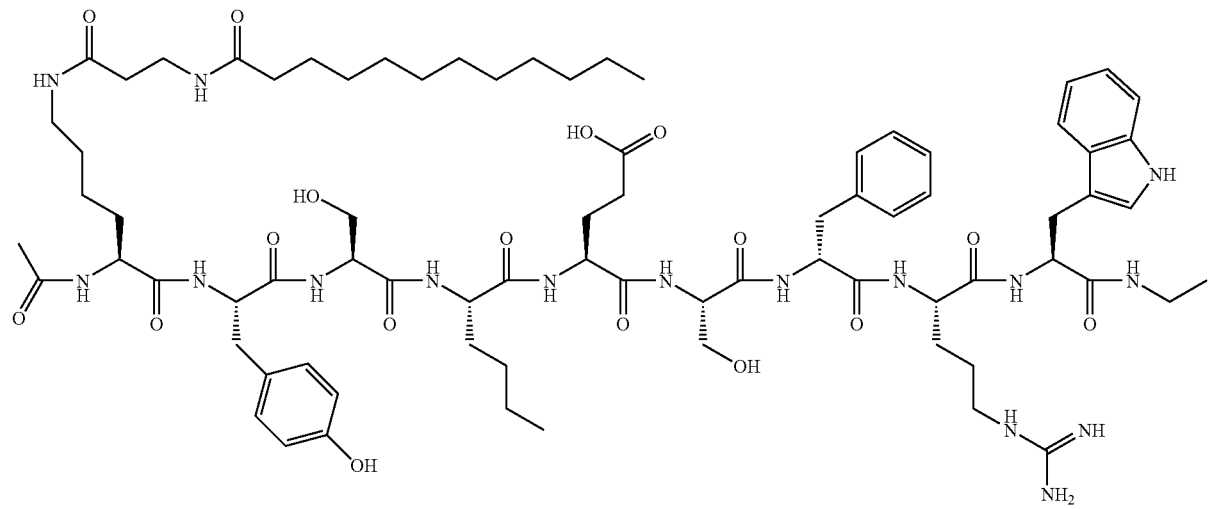
LC/MS (system 1): Rt=3.49 min; (m+1)=1891

Example 10
Hexadecanoyl-Ser-Tyr-Ser-Nle-Glu-Ser-D-Phe-Arg-Trp-Gly-Lys-Pro-Val-NH2
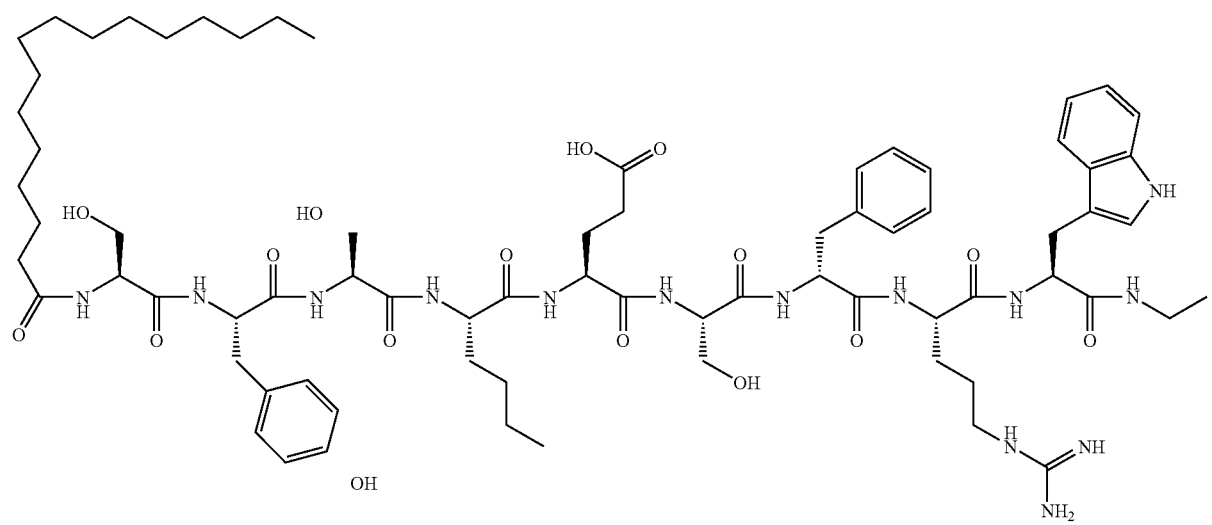
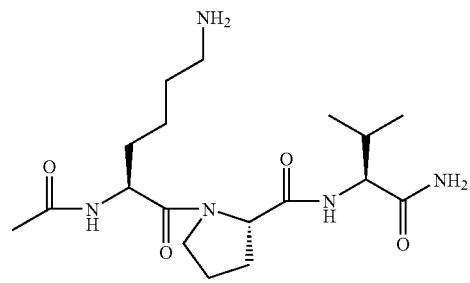
LC/MS (system 1): Rt=4.27 min; ((m+2)/2)=897

Example 11
Hexadecanoyl-Ser-Tyr-Ser-Nle-Glu-3-PyAla-D-Phe-
Arg-Trp-Gly-Lys-Pro-Val-NH2
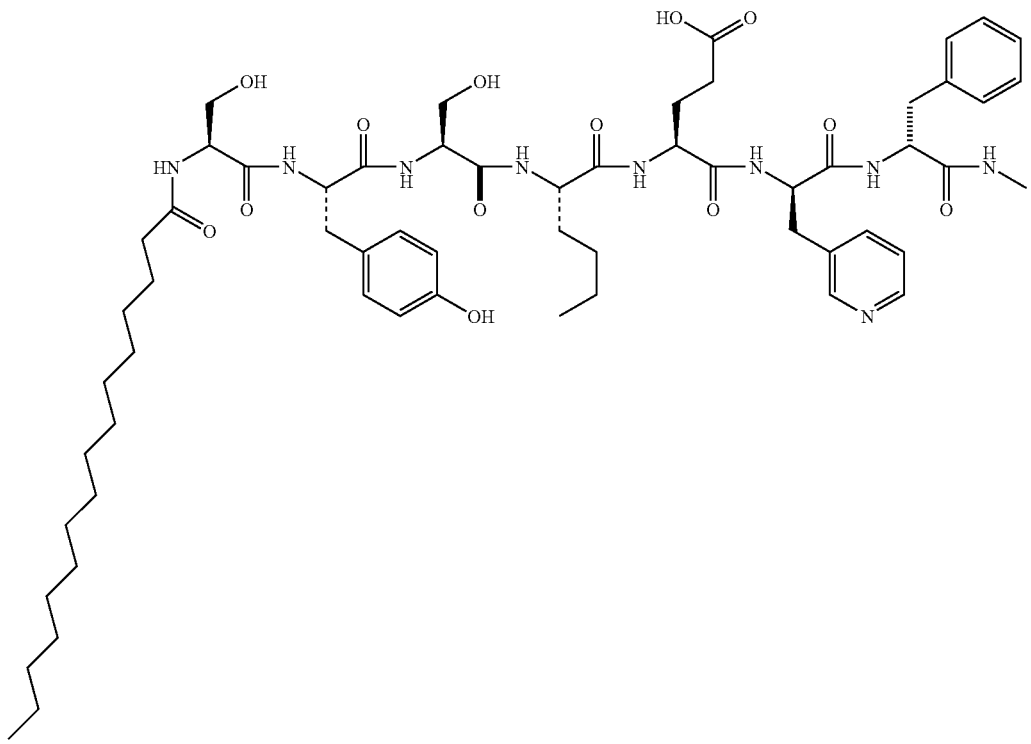
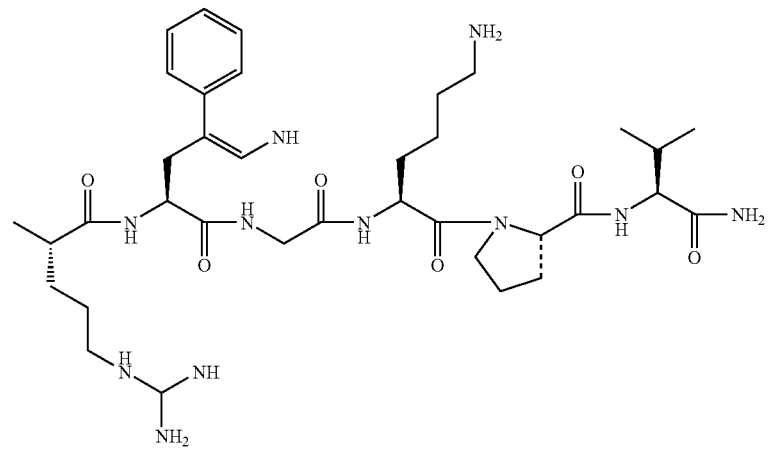
LC/MS (system 2): Rt=4.37 min; ((m+2)/2)=928

Example 12
2-[2-(Hexadecanoylamino)ethoxy]ethoxyacetyl-Ser-Tyr-Ser-Nle-Glu-3-PyAla-D-Phe-Arg-Trp-Gly-Lys-Pro-Val-NH2
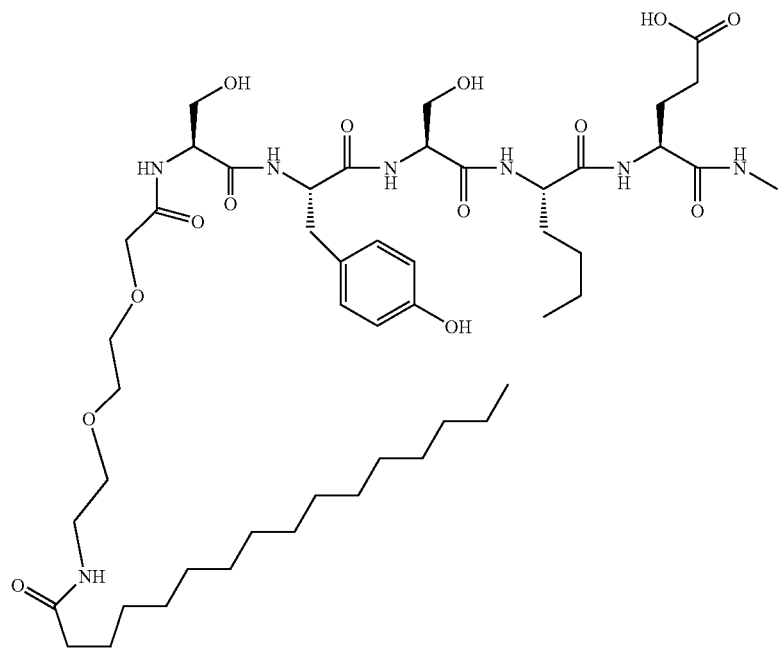
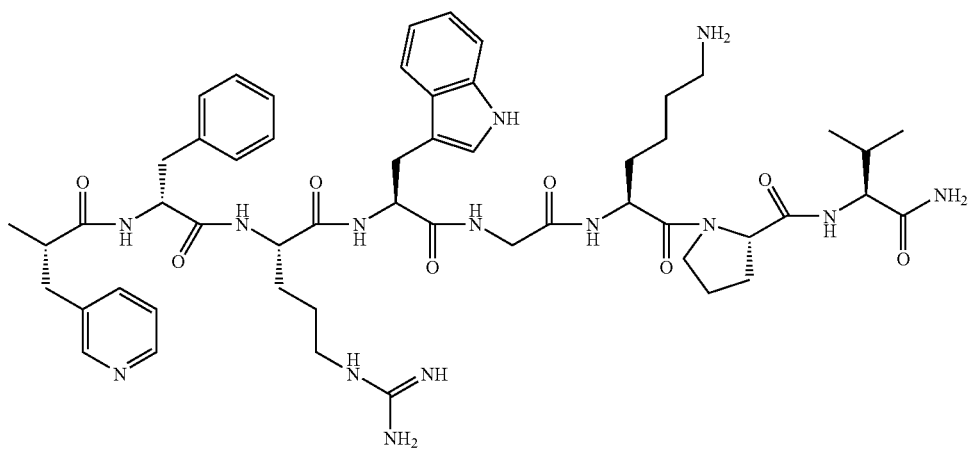
LC/MS (system 2): Rt=4.01 min; ((m+2)12)=1001

Example 13
Hexadecanoyl-βAla-Tyr-Ser-Nle-c[Glu-Hyp-D-Phe-Arg-Trp-Lys]-NH2
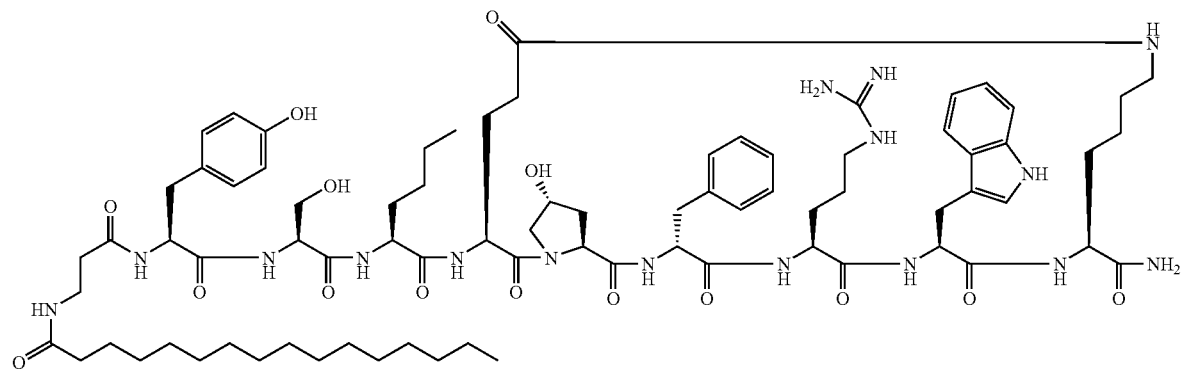
LC/MS (system 1): Rt=4.77 min; (m+1)=1533, ((m+2)/2)=767
Example 14
Hexadecanoyl-βAla-Ala-Tyr-Ser-Nle-c[Glu-Hyp-D-Phe-Arg-Trp-Lys]-NH2
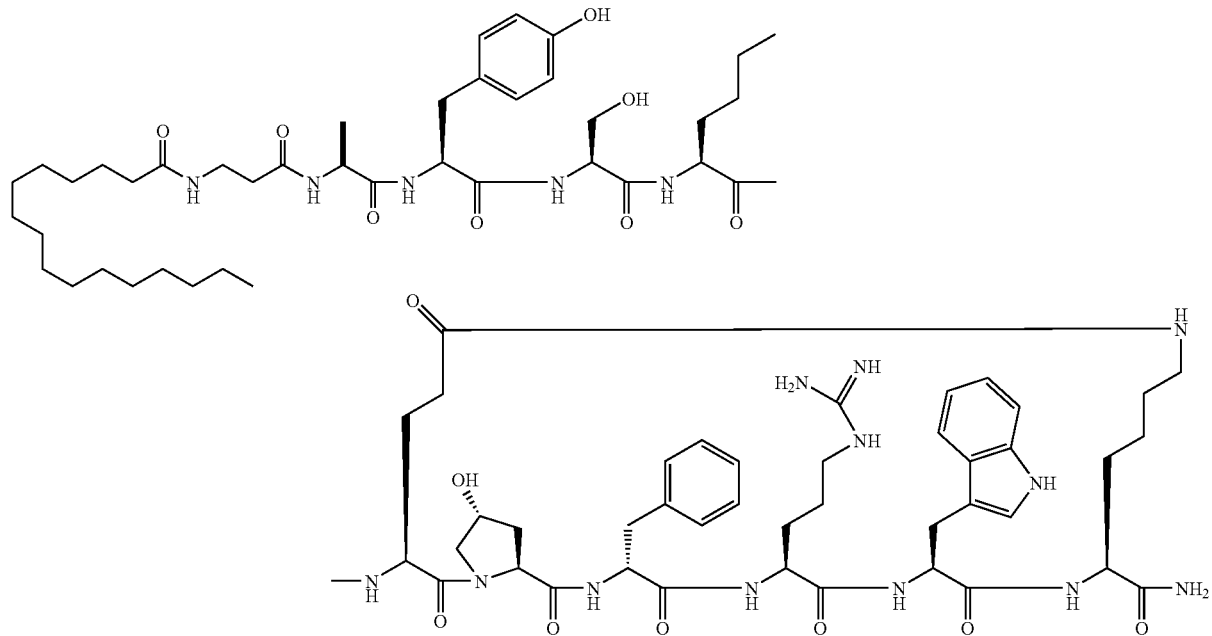
LC/MS (system 1): Rt=4.74 min ((m+2)/2)=802

Example 15
Acetyl-Ser-Lys(3-(dodecanoylamino)propionyl)-Ser-Nle-Glu-Hyp-D-Phe-Arg-Trp-Gly-Lys-Pro-Val-NH2
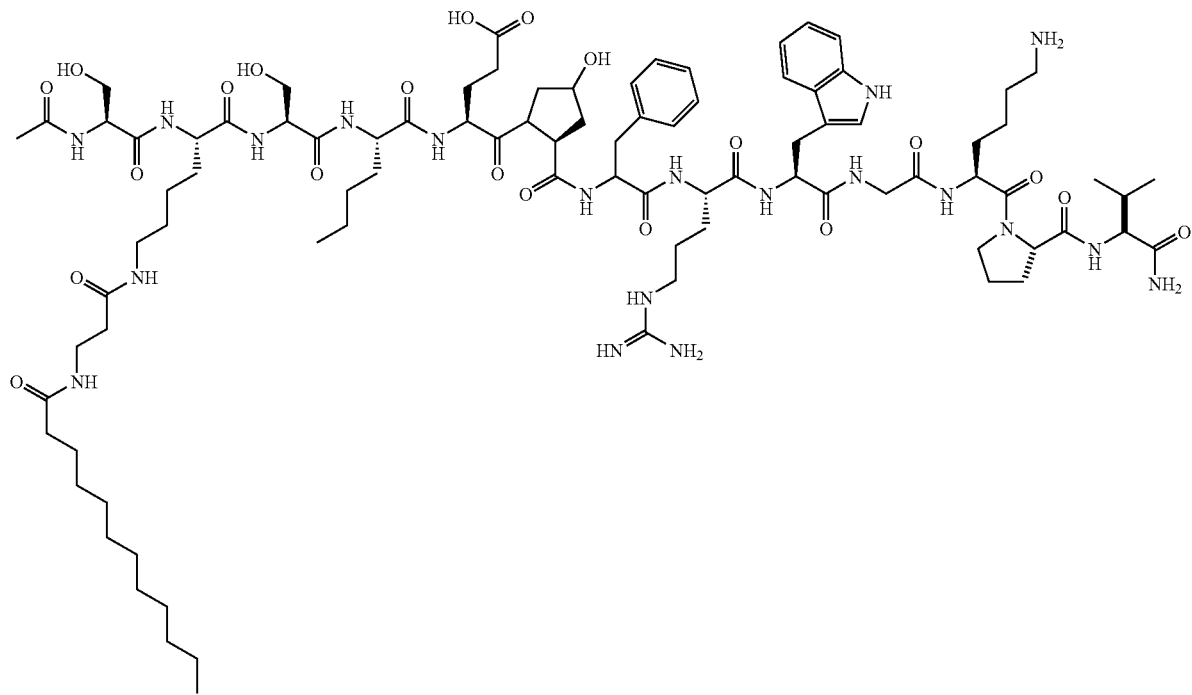
LC/MS (system 1): Rt=3.44 min; ((m+2)/2)=921
Example 16
mPEG(2000)acetyl-Nle-c[Glu-Hyp-D-Phe-Arg-Trp-Lys]-NH2
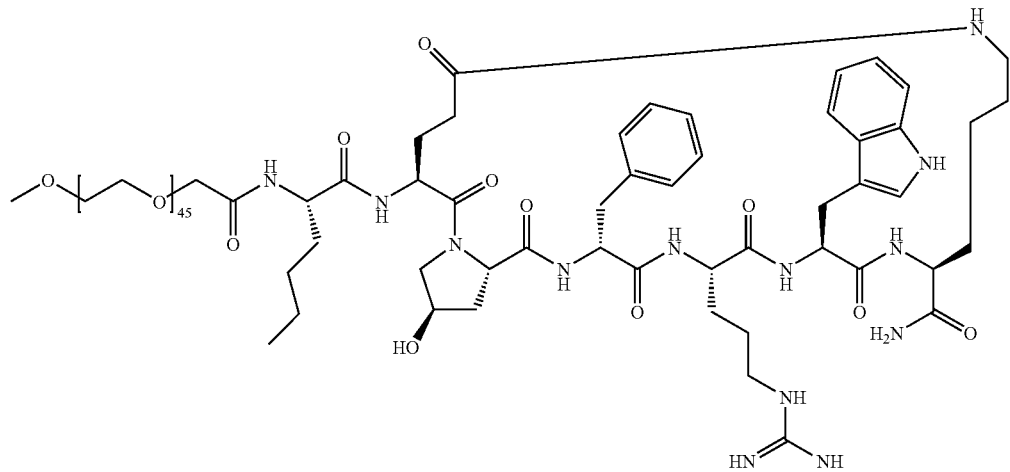
LC/MS (system 1): Rt=3.29 min

Example 17
2-[2-(Lithocholoylamino)ethoxy]ethoxyacetyl-βAla-
Tyr-Ser-Nle-c[Glu-Hyp-D-Phe-Arg-Trp-Lys]-NH2
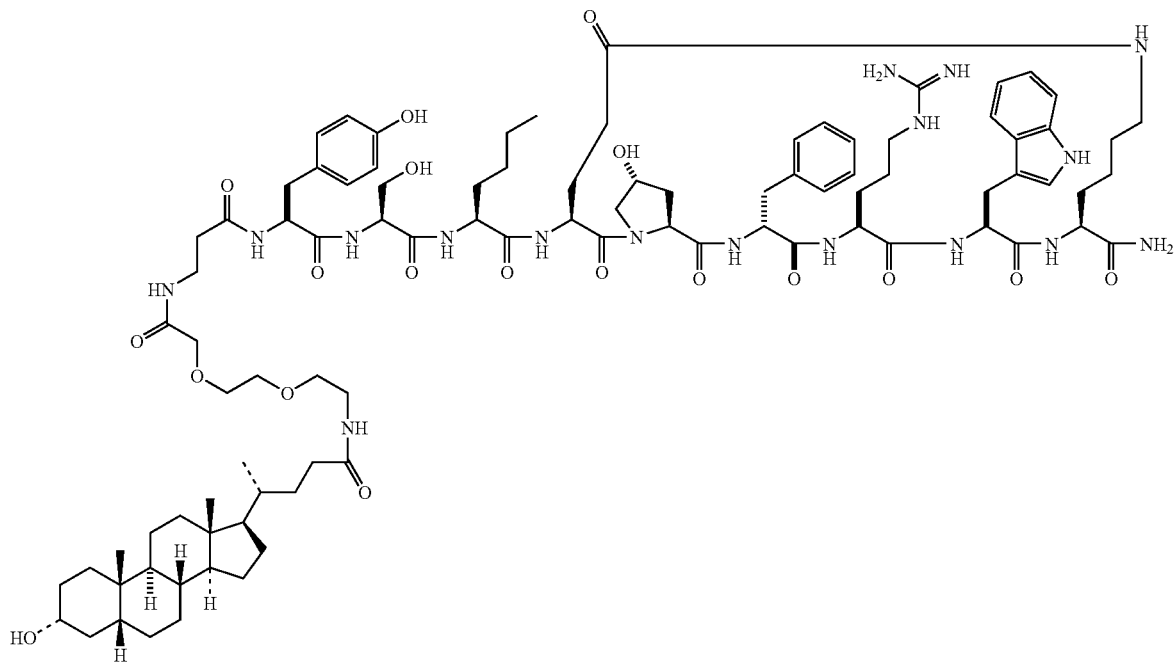
LC/MS (system 1): Rt=3.92 min; ((m+2)/2)=899
Example 18
2-[2-(15-Carboxypentadecanoylamino)ethoxy]
ethoxyacetyl-βAla-Ala-Tyr-Ser-Nle-c[Glu-Hyp-D-
Phe-Arg-Trp-Lys]-NH2
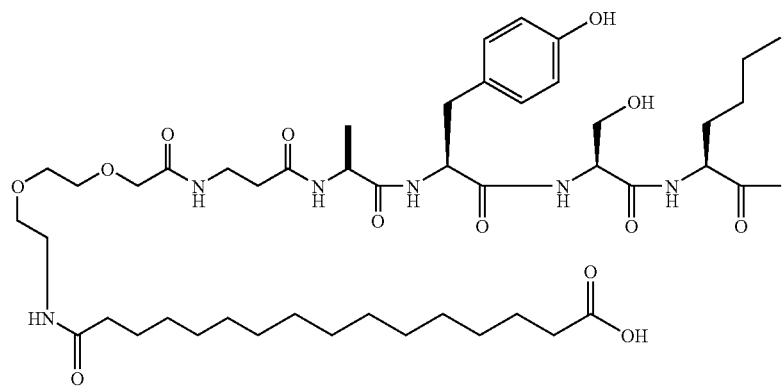

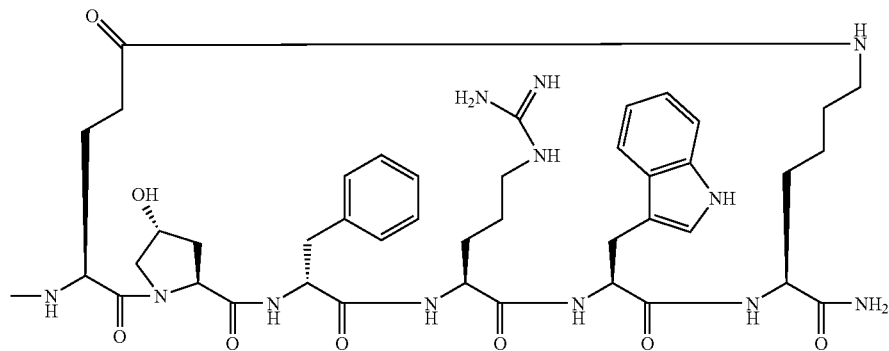
LC/MS (system 1): Rt=3.65 min; ((m+2)/2) 890
Example 19
Acetyl-Ser-Lys(3-(dodecanoylamino)propionyl)-Ser-Phe-Glu-Hyp-D-Phe-Arg-Trp-Gly-Lys-Pro-Val-NH2
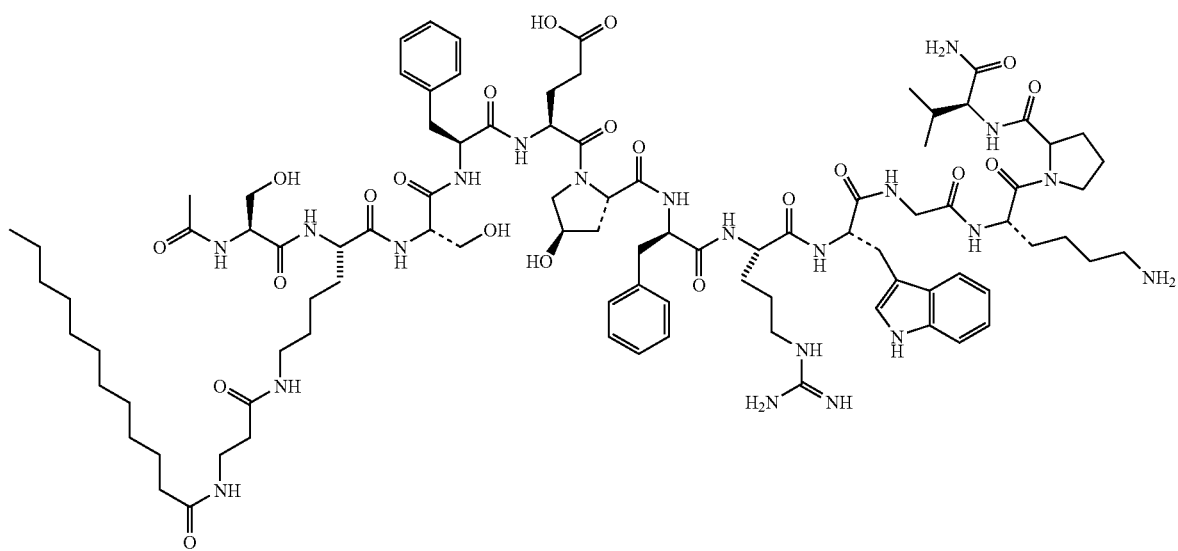
LC/MS (system 1): Rt=3.41 min; ((m+2)/2)=939

Example 20
2-[2-(15-Carboxypentadecanoylamino)ethoxy]ethoxyacetyl-Ser-Gln-Ser-Nle-c[Glu-Hyp-D-Phe-Arg-Trp-Lys]-NH2
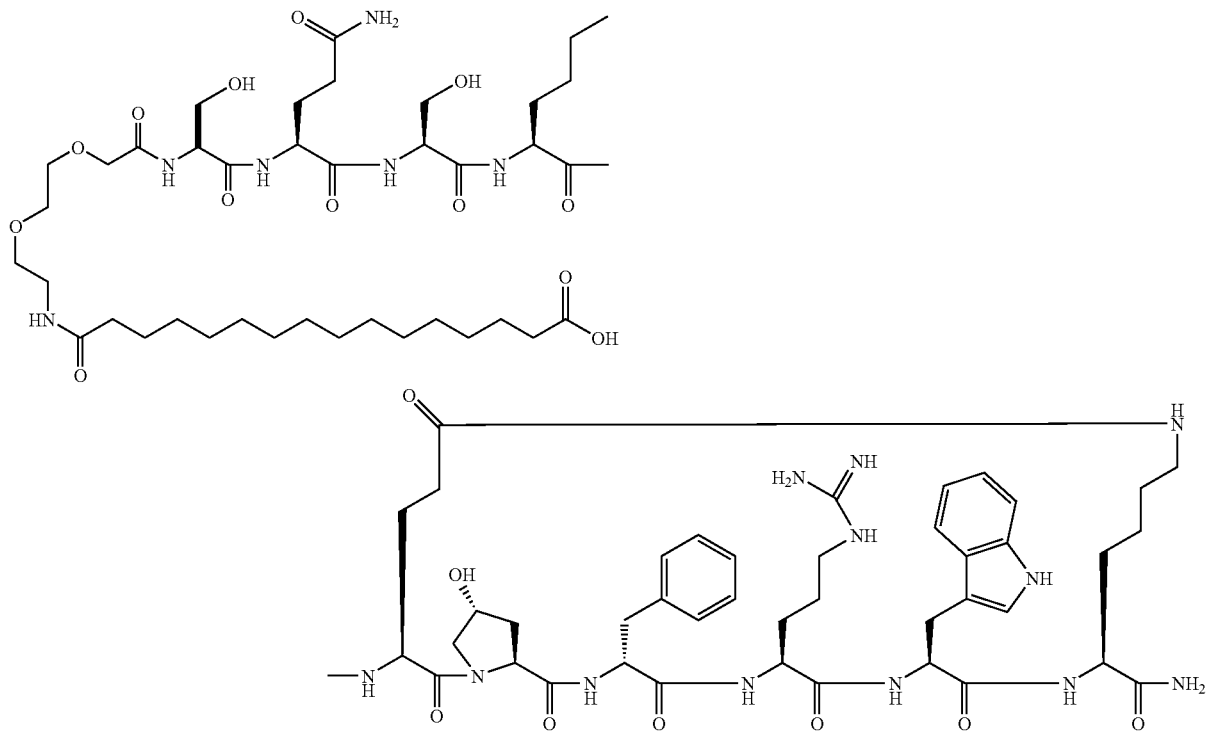
LC/MS (system 1): Rt=3.5 min; (m+1)=1688, ((m+2)/2)=844
Example 21
Hexadecanoyl-Gly-Ser-Gln-His-Ser-Nle-c[Glu-Hyp-D-Phe-Arg-Trp-Lys]-NH2
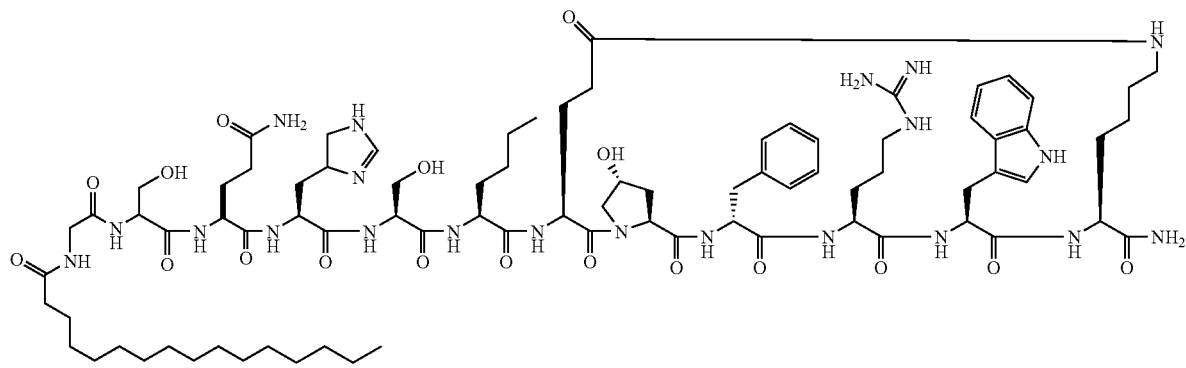
LC/MS (system 1): Rt=3.92 min; (m+1)=1708, ((m+2)/2)=854

Example 22
15-Carboxypentadecanoyl-Gly-Ser-Gln-His-Ser-Nle-c[Glu-Hyp-D-Phe-Arg-Trp-Lys]-NH2
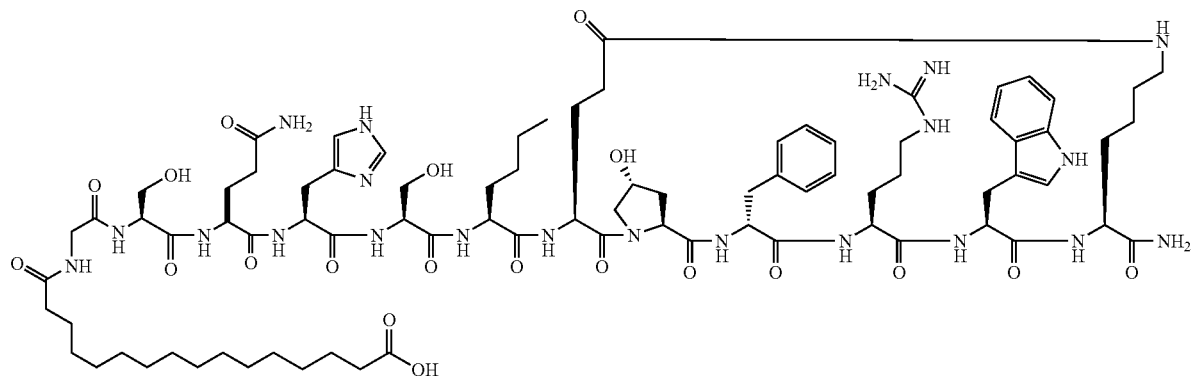
LC/MS (system 1): Rt=3.10 min; ((m+2)/2)=869
Example 23
4-(Hexadecanoylsulfamoyl)butanoyl-Gly-Ser-Gln-His-Ser-Nle-c[Glu-Hyp-D-Phe-Arg-Trp-Lys]-NH2
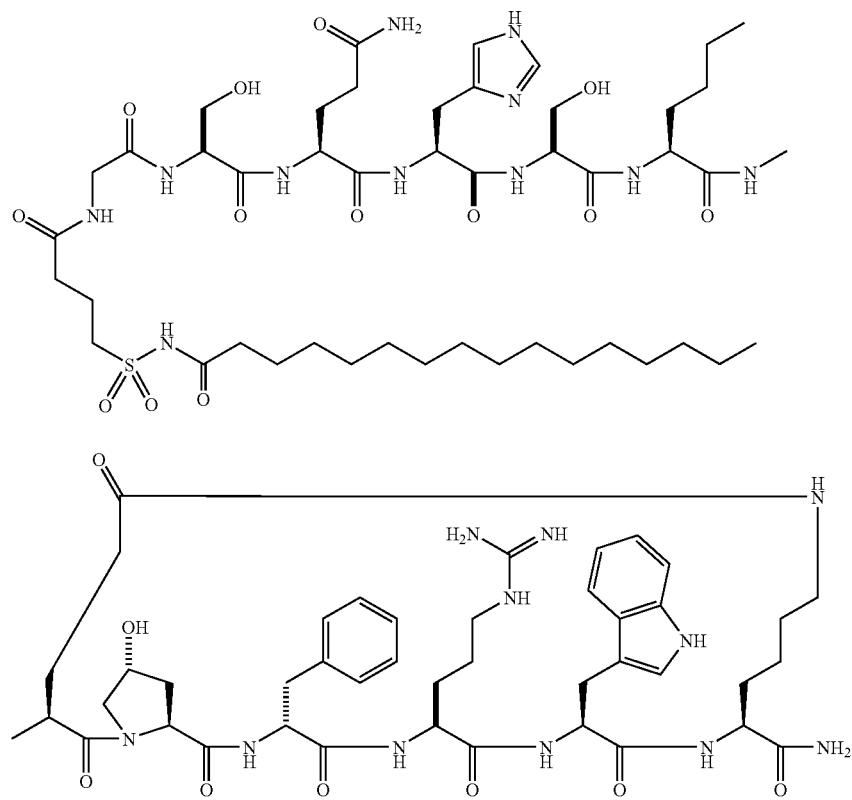
LC/MS (system 1): Rt=4.01 min; ((m+2)/2)=929

Example 24
4-[2-(4-Benzoylphenyl)propionylsulfamoyl]bu-tanoyl-Gly-Ser-Gln-His-Ser-Nle-c[Glu-Hyp-D-Phe-Arg-Trp-Lys]-NH2
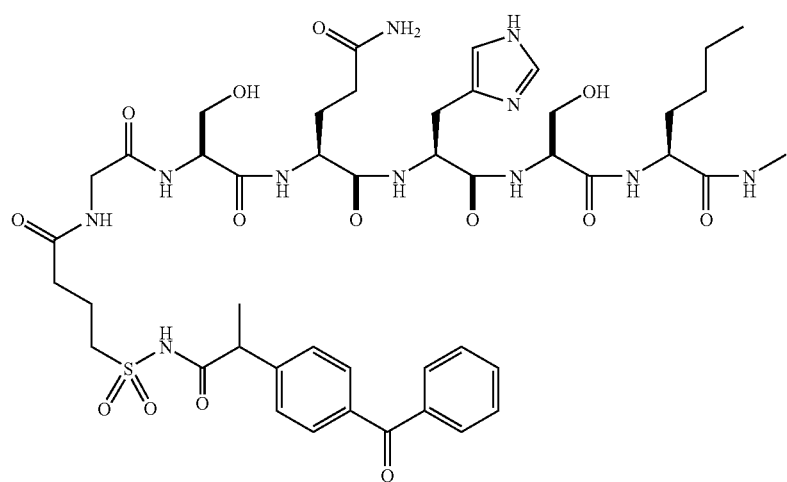
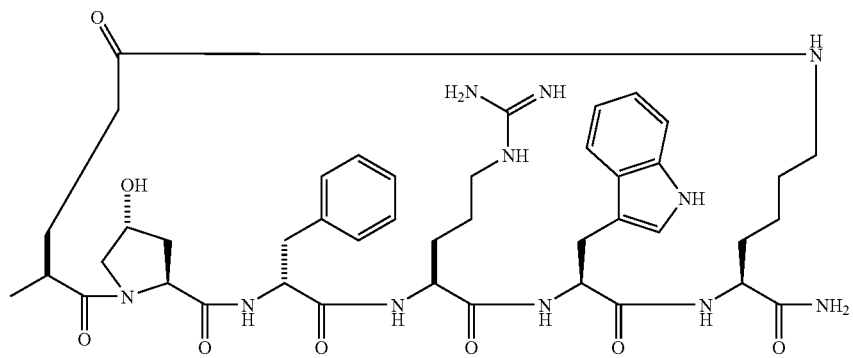
LC/MS (system 1): Rt=2.79 min; ((m+2)/2)=928

Example 25
2-[2-(Octadecanoylamino)ethoxy]ethoxyacetyl-Gly-Ser-Gln-His-Ser-Nle-c[Glu-Hyp-D-Phe-Arg-Trp-Lys]-NH2
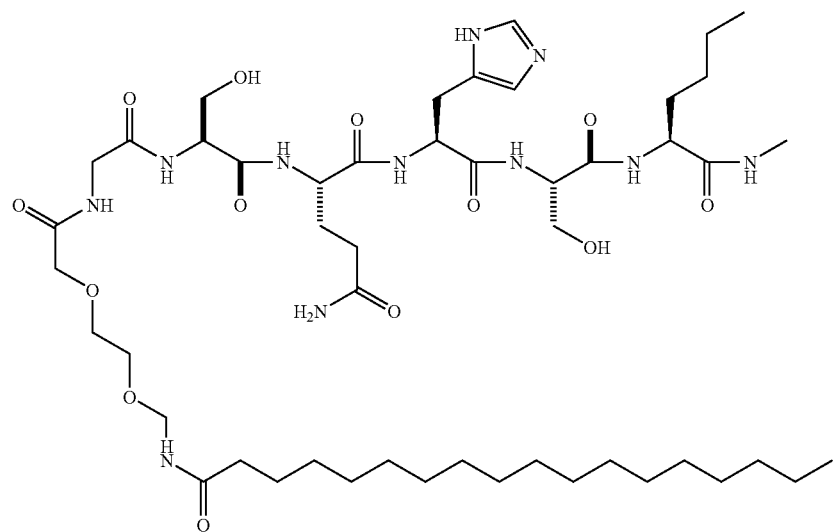
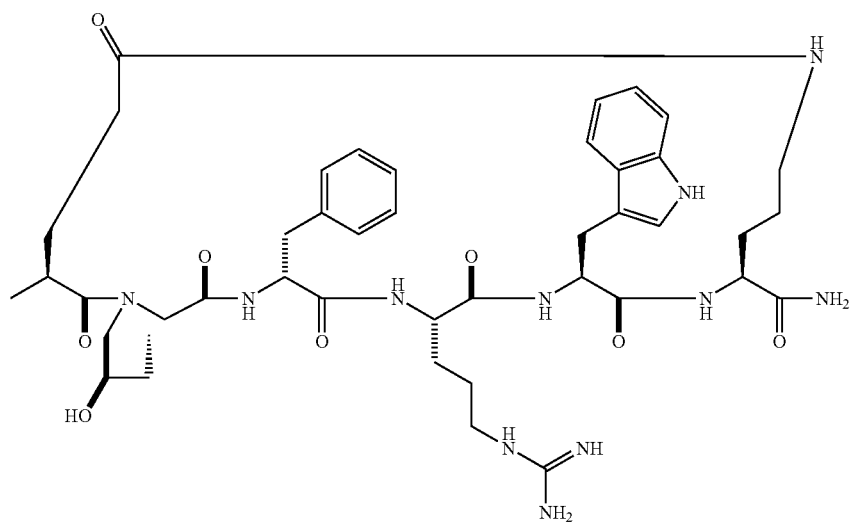
LC/MS (system 1): Rt=4.37 min; ((m+2)/2)=941

Example 26
2-[2-Octadecanoylamino)ethoxy]ethoxyacethl-Nle-c[Glu-Hyp-D-Phe-Arg-Trp-Lys]-NH2
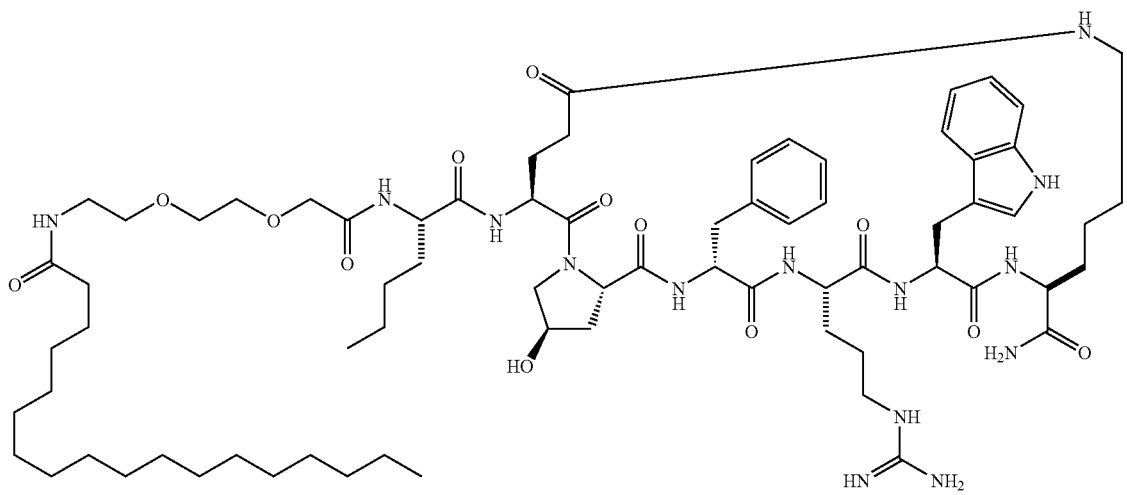
LC/MS (system 1): Rt=5.08 min; (m+1)=1384
Example 27
Hexadecanoyl-Gly-Ser-Gln-homoArg-Ser-Nle-c[Glu-Hyp-D-Phe-Arg-Trp-Lys]-NH2
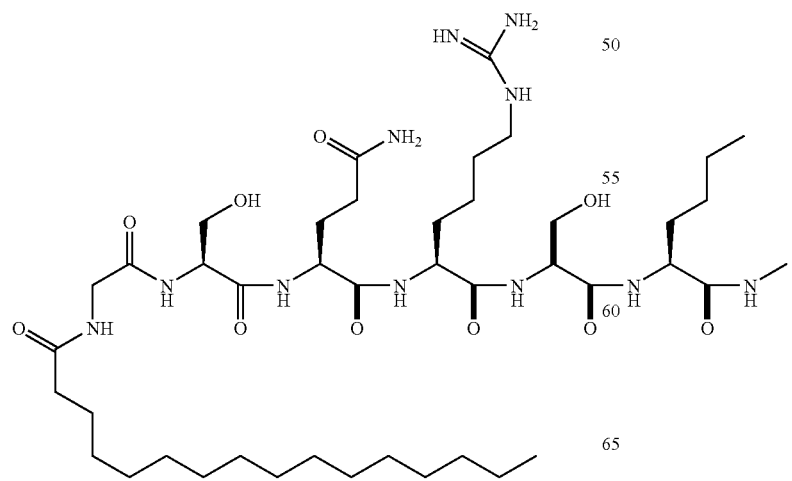

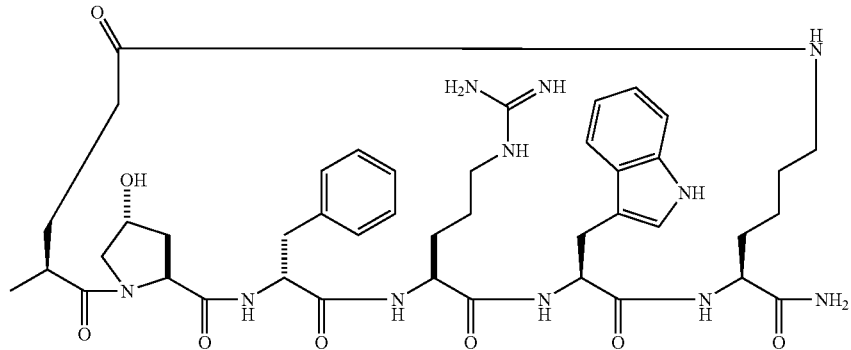
LC/MS (system 1): Rt=4.07 min; ((m+2)/2)=871
Example 28
2-[2-(15-Carboxypentadecanoylamino)ethoxy]ethoxyacetyl-Nle-c[Glu-Hyp-D-Phe-Arg-Trp-Lys]-NH2
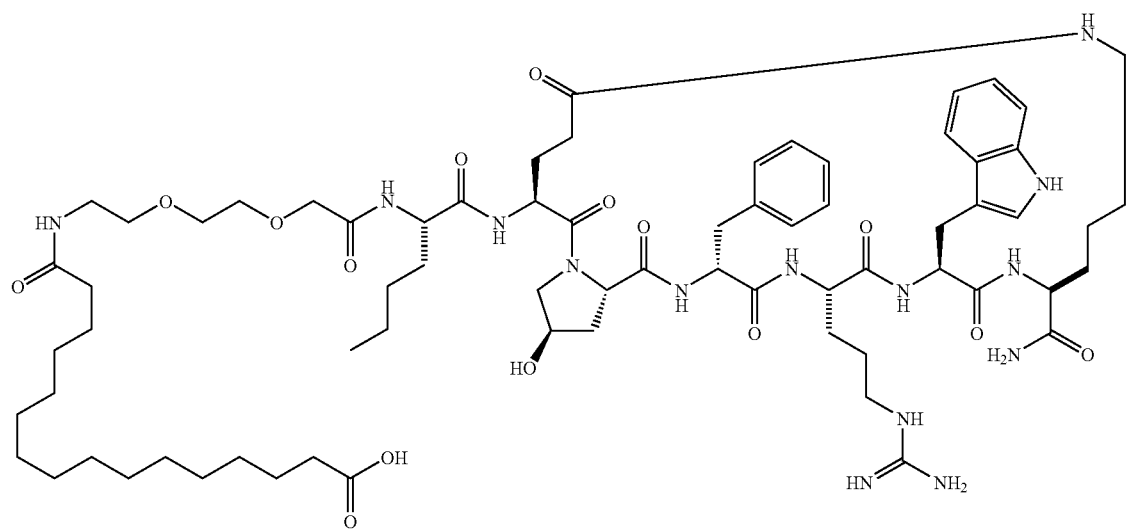
LC/MS (system 1): Rt=3.71 min; (m+1)=1386

Example 29
Hexadecanoyl-Gly-Ser-Gln-His-Ser-Nle-c[Glu-Met(O2)-D-Phe-Arg-Trp-Lys]-NH2
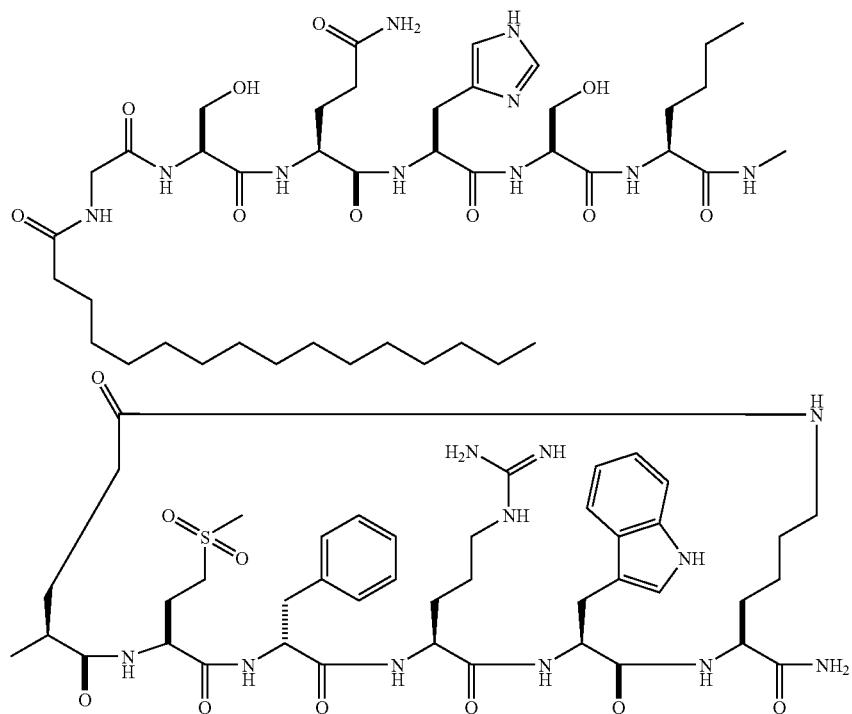
LC/MS (system 1): Rt=4.07 min; (m+1)=1757, ((m+2)/2)=879
Example 30
4-Hexadecanoylsulfamoyl)butanoyl-Gly-Ser-Gln-Arg-Ser-Nle-c[Glu-Met(O2)-D-Phe-Arg-Trp-Lys]-NH2
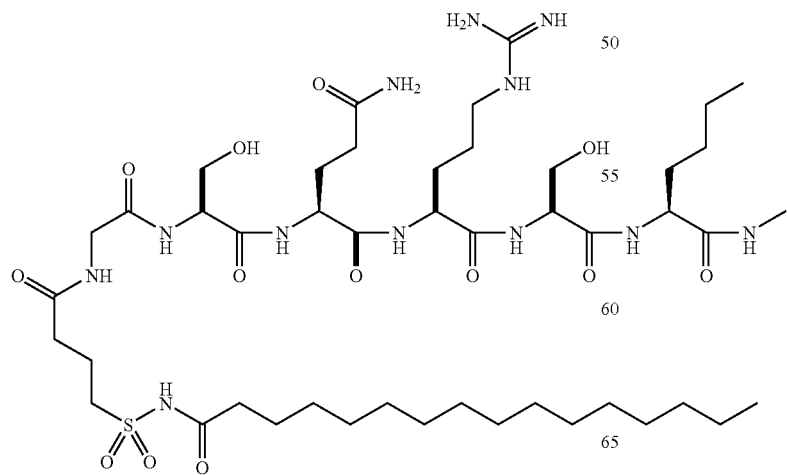

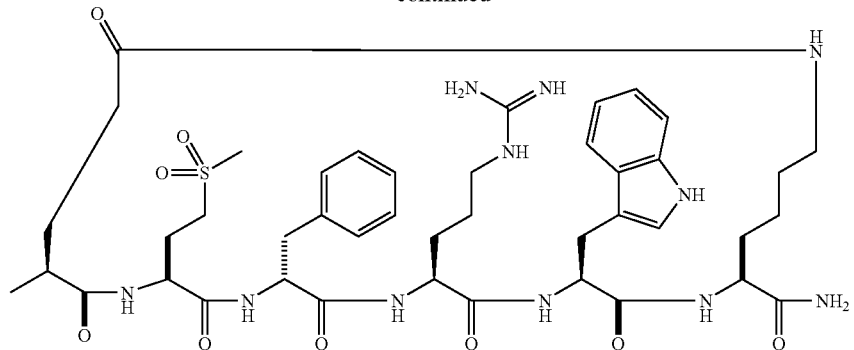
LC/MS (system 1): Rt=4.48 min; ((m+2)/2)=963
Example 31
Hexadecanoyl-Gly-Ser-Gln-homoArg-Ser-Nle-c
[Glu-3-PyAla-D-Phe-Arg-Trp-Lys]-NH2
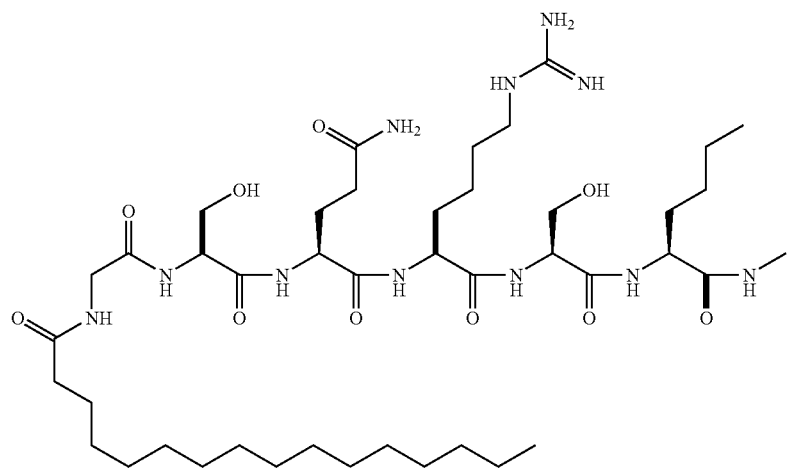
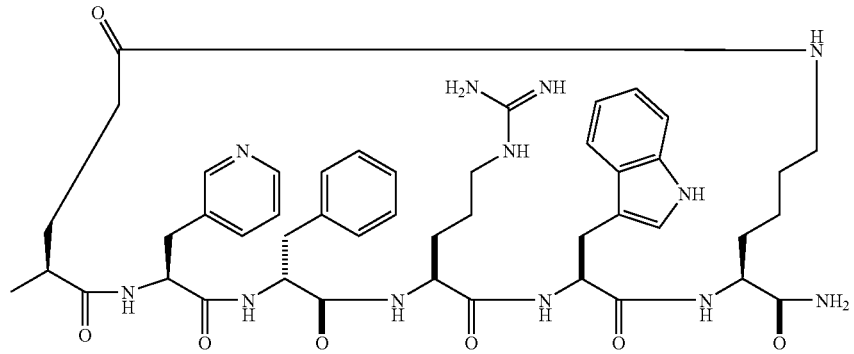
LC/MS (system 1): Rt=3.68 min; ((m+2)/2)=888

Example 32
Hexadecanoyl-Gly-Ser-Gln-Arg-Ser-Nle-c[Glu-Met
(O2)-D-Phe-Arg-Trp-Lys]-NH2
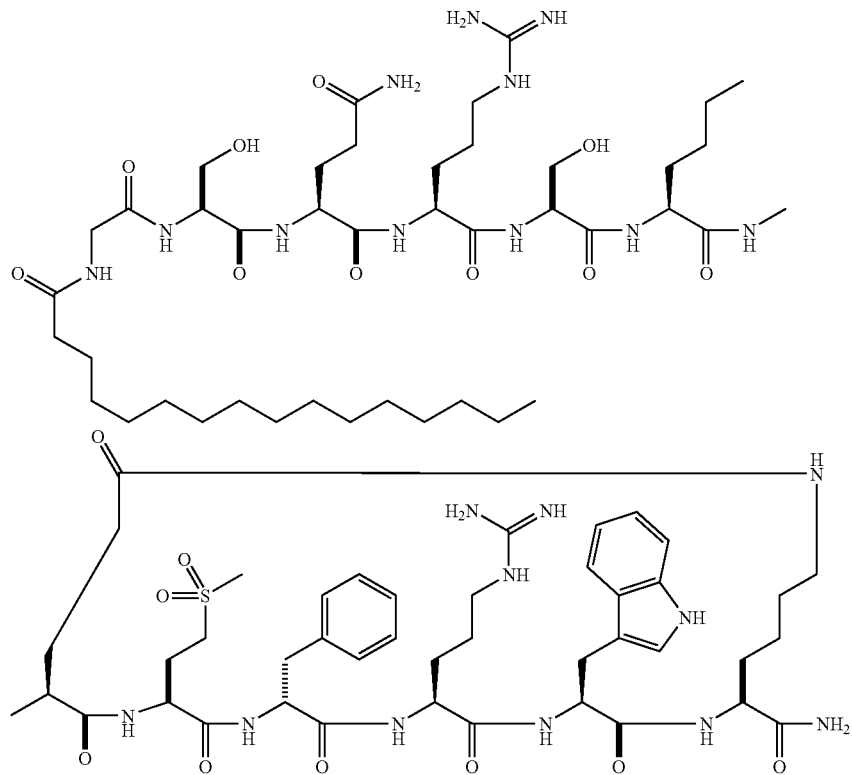
LC/MS (system 1): Rt=4.15 min; (m+1)=1778, ((m+2)/2) =889
Example 33
4-(Hexadecanoylsulfamoyl)butanoyl-Gly-Ser-Gln-
Arg-Ser-Nle-c[Glu-Gln-D-Phe-Arg-Trp-Lys]-NH2
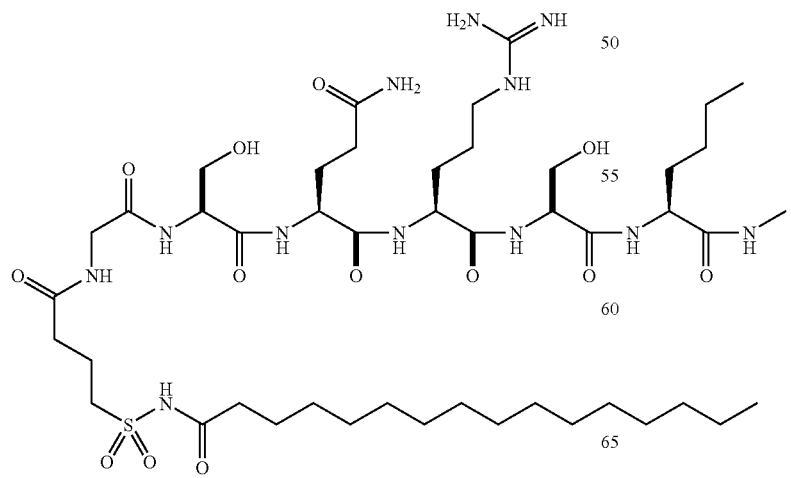

-continued
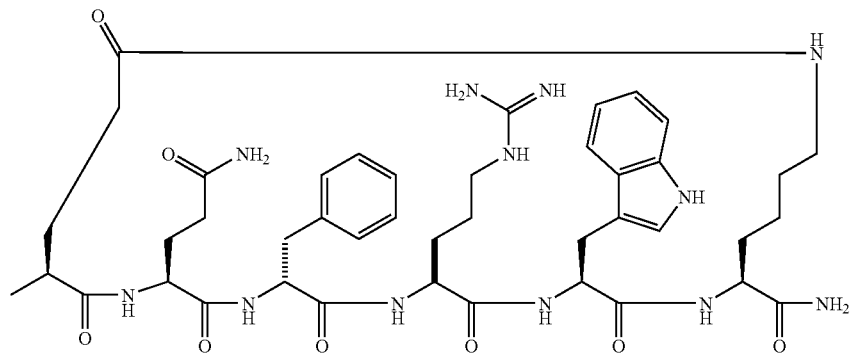
LC/MS (system 1): Rt=4.37 min; ((m+2)/2)=946
Example 34
3-(2-{2-[2-(2-(Hexadecanoylamino)ethoxy)ethoxy]ethoxy}ethoxy)propionyl-Nle-c[Glu-Hyp-D-Phe-Arg-Trp-Lys]-NH2
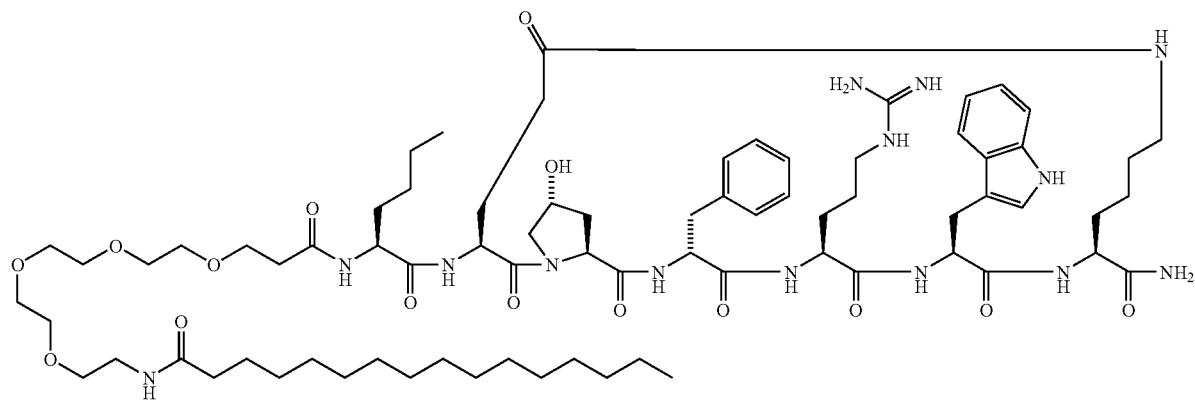
LC/MS (system 1): Rt=4.80 min; (m+1)=1458, ((m+2)/2)=730

Example 35
2-[2-(Hexadecanoylamino)ethoxy]ethoxyacetyl-Gly-Ser-Gln-His-Ser-Nle-c[Glu-Hyp-D-Phe-Arg-Trp-Lys]-NH2
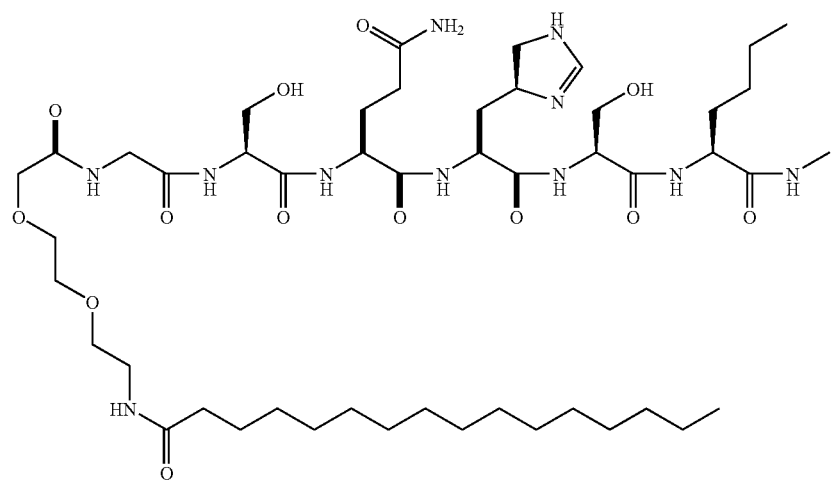
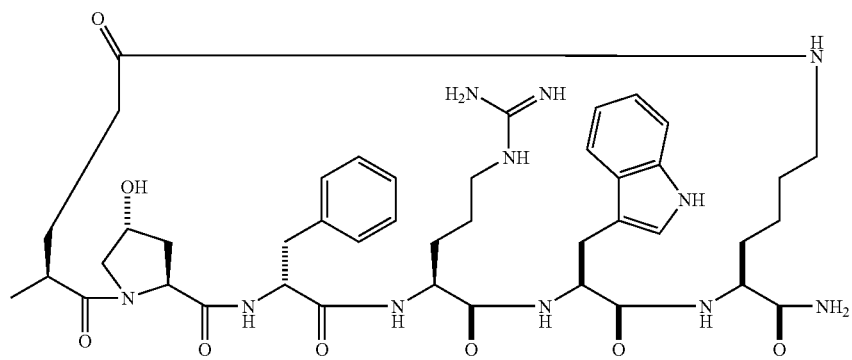
LC/MS (system 1): Rt=4.30 min; ((m+2)/2)=927

Example 36
2-[2-(Tetradecanoylamino)ethoxy]ethoxyacetyl-Gly-Ser-Gln-His-Ser-Nle-c[Glu-Hyp-D-Phe-Arg-Trp-Lys]-NH2
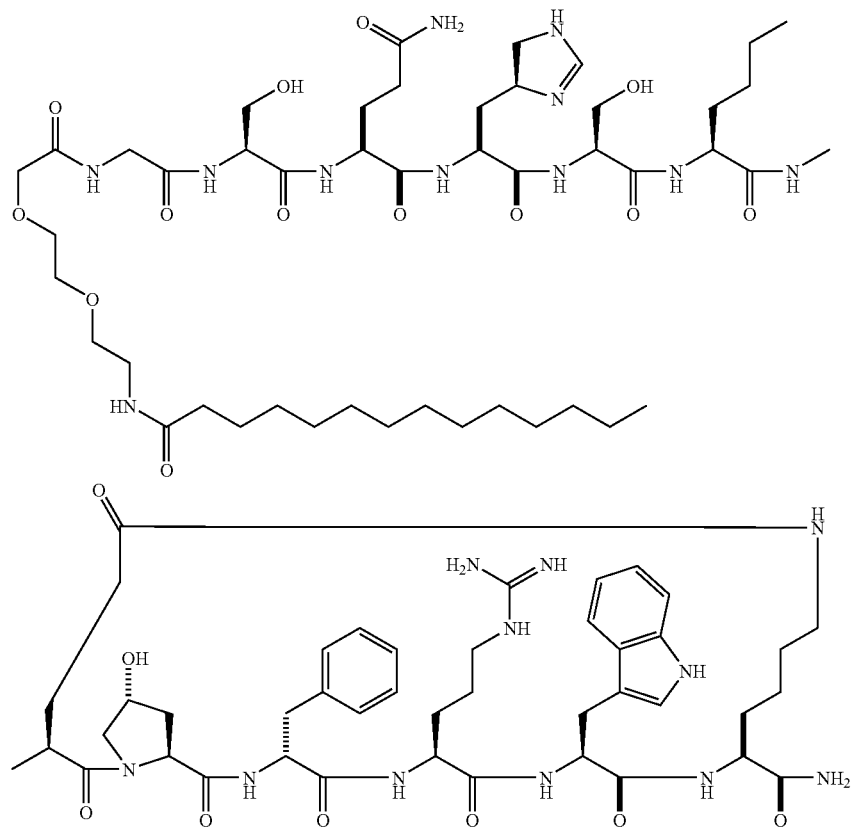
LC/MS (system 1): Rt=3.91 min; ((m+2)/2)=913
Example 37
Hexadecanoyl-Gly-Thr-Gln-His-Ser-Nle-c[Glu-Hyp-D-Phe-Arg-Trp-Lys]-NH2
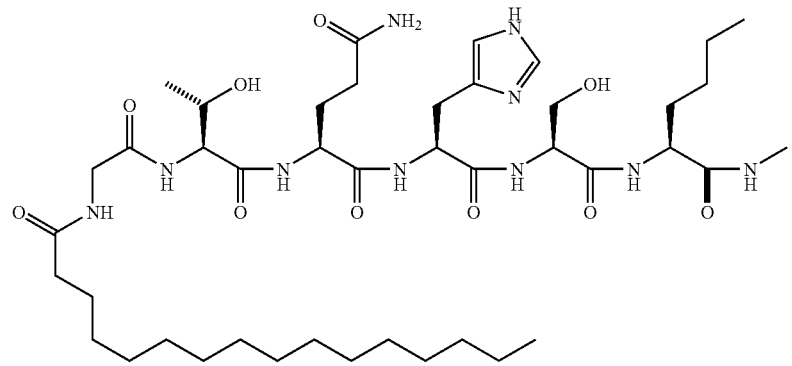

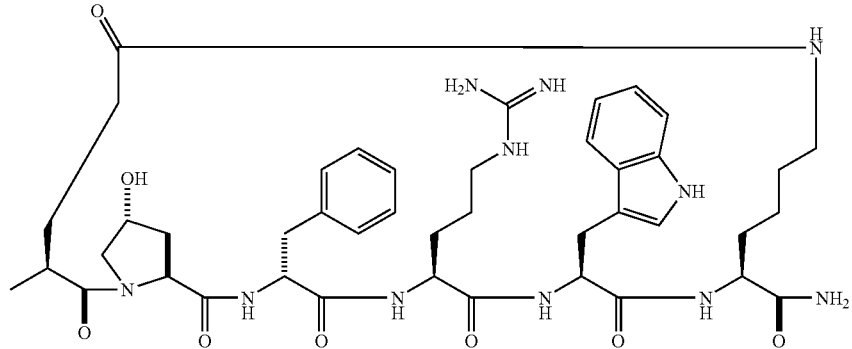
LC/MS (system 1): Rt=4.15 min; (m+1)=1722
Example 38
Hexadecanoyl-Gly-Gln-Gln-His-Ser-Nle-c[Glu-Hyp-D-Phe-Arg-Trp-Lys]-NH2
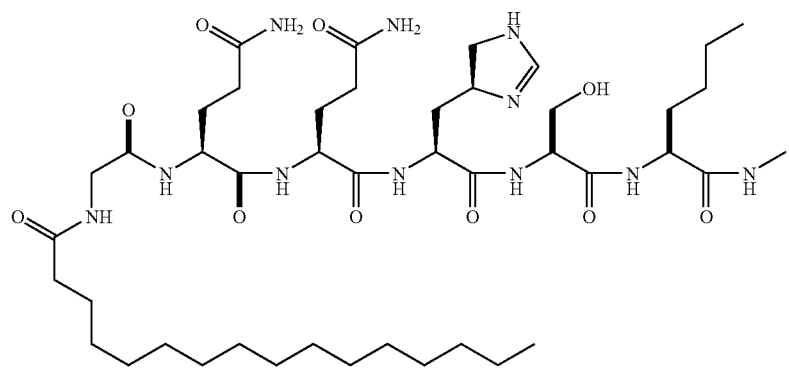
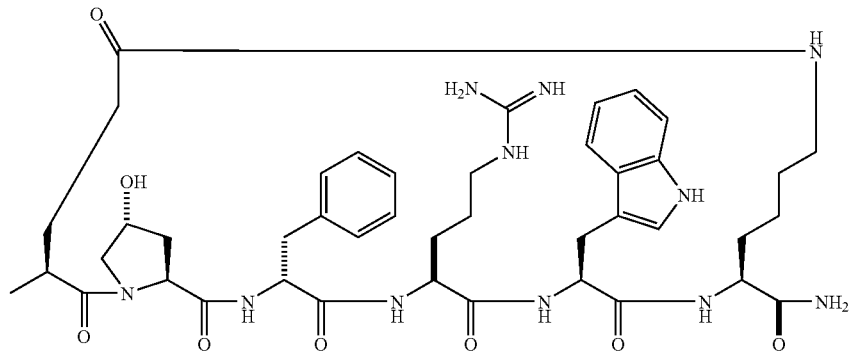
LC/MS (system 1): Rt=4.08 min; (m+1)=1748

Example 39
Hexadecanoyl-Gly-Thr-Gln-His-Ser-Nle-c[Glu-Asn-
D-Phe-Arg-Trp-Lys]-NH2
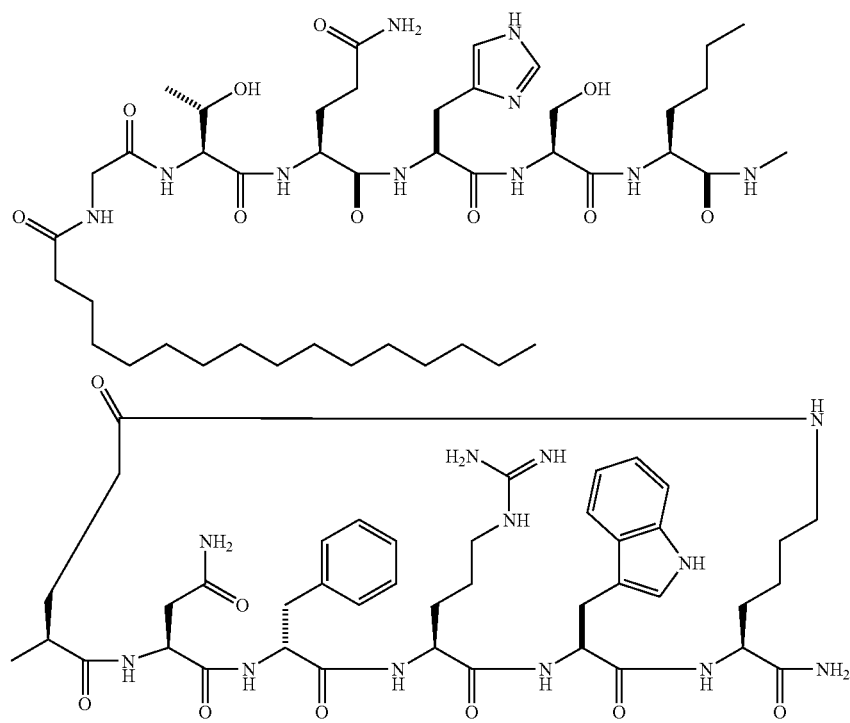
LC/MS (system 1): Rt=4.13 min; (m+1)=1723
Example 40
Hexadecanoyl-Gly-Glu-Thr-Gln-His-Ser-Nle-c[Glu-
Hyp-D-Phe-Arg-Trp-Lys]-NH2
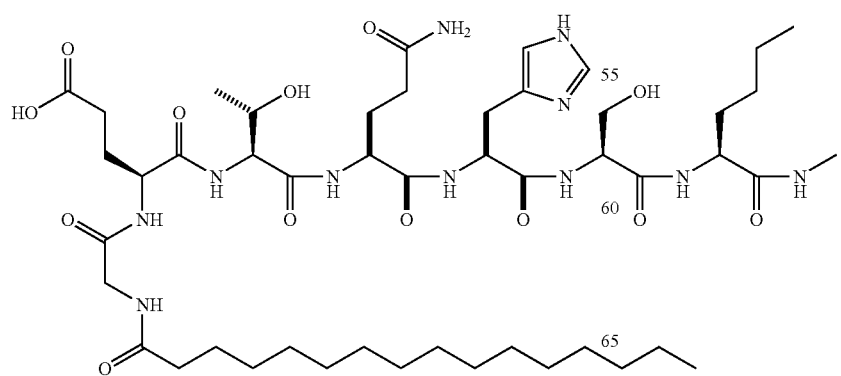

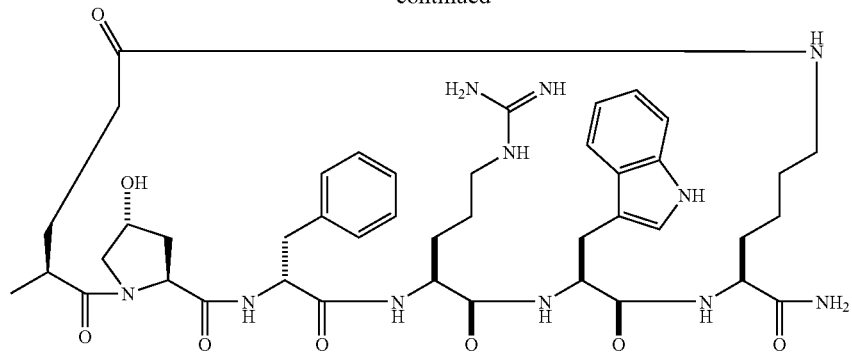
LC/MS (system 1): Rt=4.16 min; ((m+2)/2)=926
Example 41
Hexadecanoyl-Glu-Gly-Thr-Gln-His-Ser-Nle-c[Glu-Hyp-D-Phe-Arg-Trp-Lys]-NH2
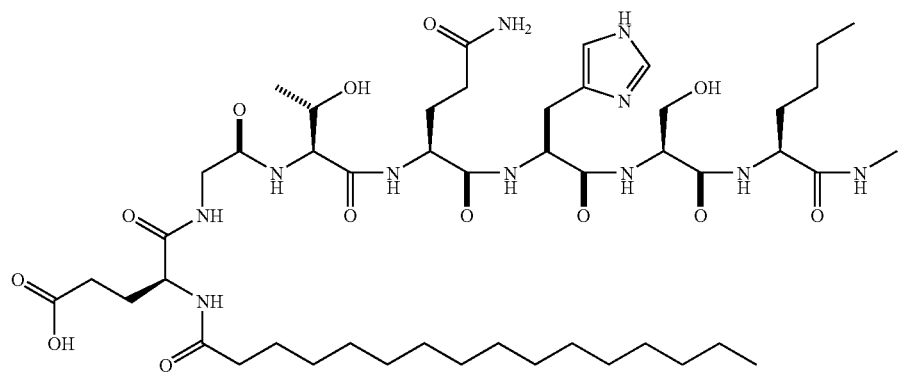
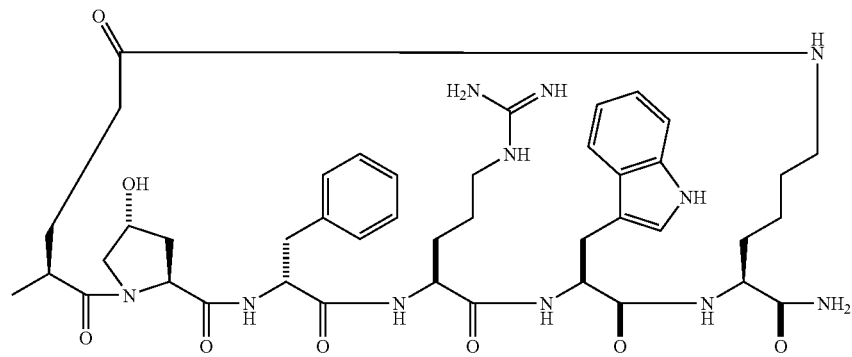
LC/MS (system 1): Rt=4.62 min; ((m+2)/2)=926

Example 42
Hexadecanoyl-Glu-4-Abu-Thr-Gln-His-Ser-Nle-c
[Glu-Hyp-D-Phe-Arg-Trp-Lys]-NH2
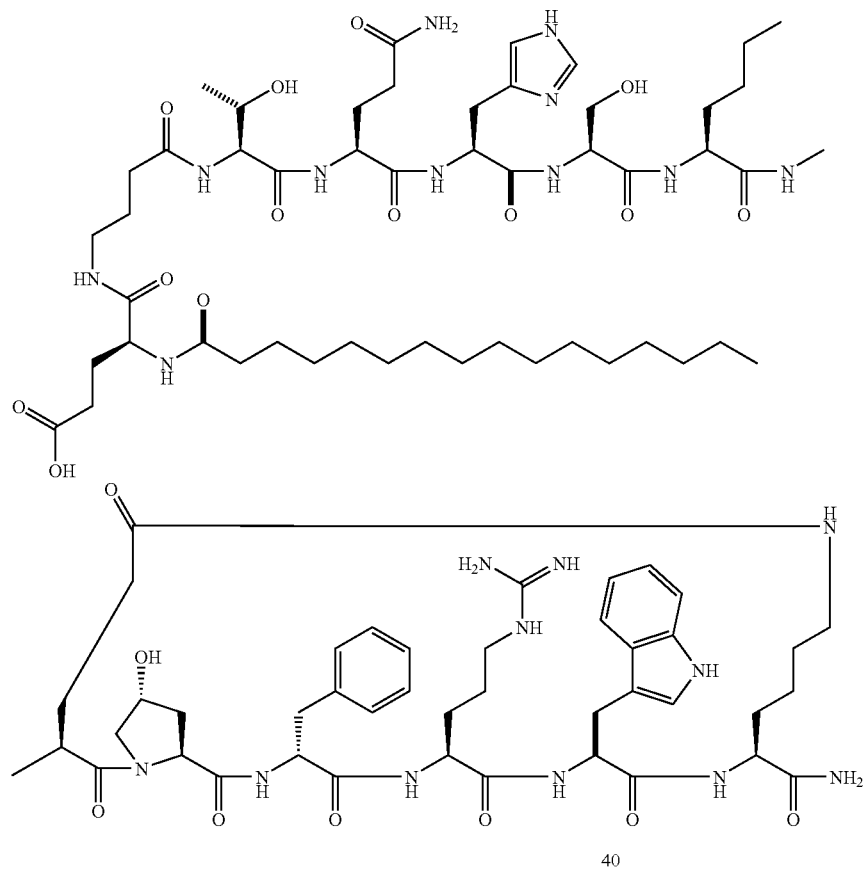
LC/MS (system 1): Rt=4.07 min; ((m+2)/2)=940
Example 43
2-[2-(Hexadecanoylamino)ethoxy]ethoxyacetyl-His-
Ser-Nle-c[Glu-Hyp-D-Phe-Arg-Trp-Lys]-NH2
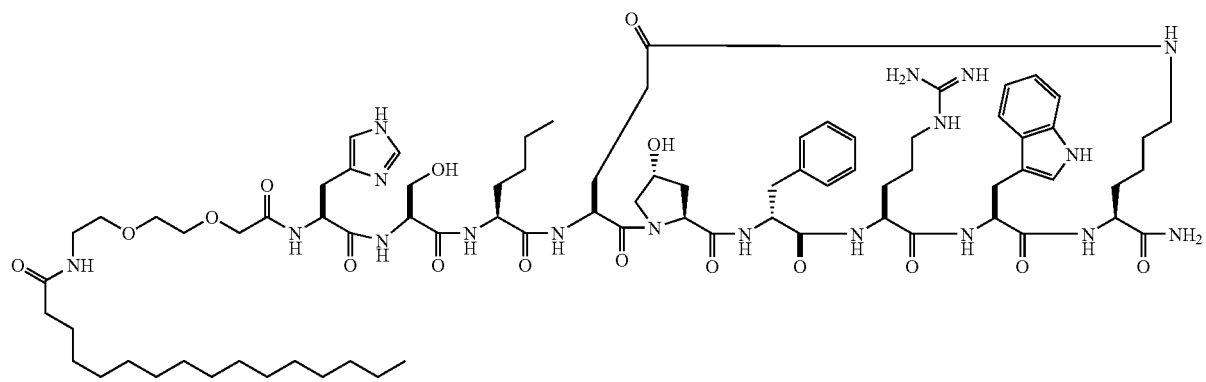
LC/MS (system 1): Rt=4.36 min; (m+1)=1580

Example 44
2-[2-(Hexadecanoylamino)ethoxy]ethoxyacetyl-Arg-Ser-Nle-c[Glu-Hyp-D-Phe-Arg-Trp-Lys]-NH2
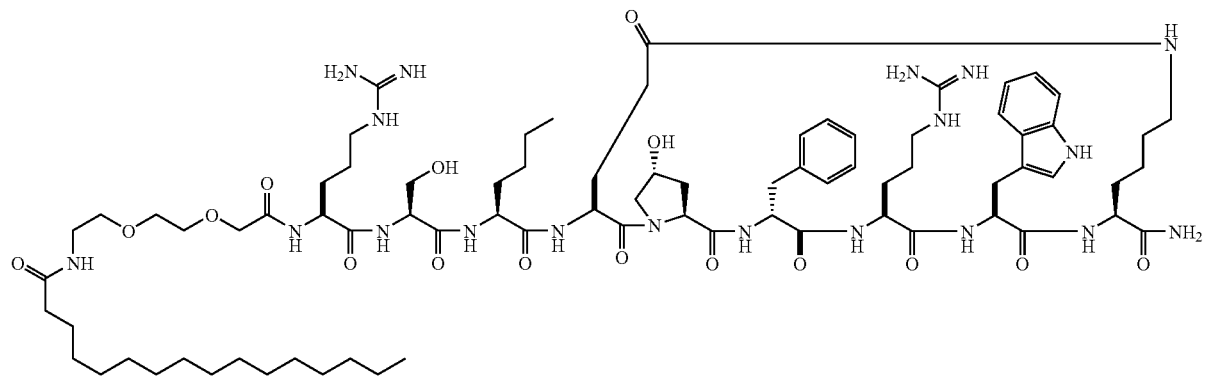
LC/MS (system 1): Rt=4.01 min; ((m+2)/2)=800
Example 45
2-[2-(Hexadecanoylamino)ethoxy]ethoxyacetyl-Gln-Ser-Nle-c[Glu-Hyp-D-Phe-Arg-Trp-Lys]-NH2
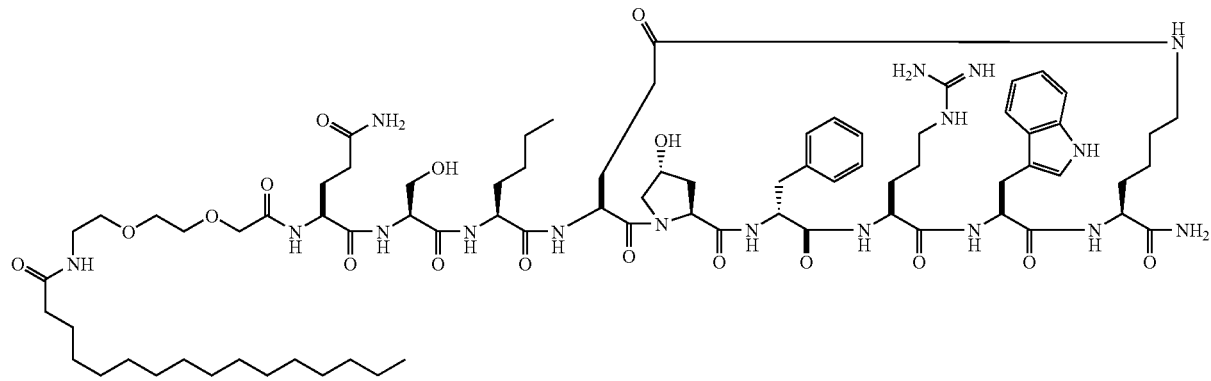
LC/MS (system 1): Rt=4.49 min; (m+1)=1571

Example 46
2-[2-(Hexadecanoylamino)ethoxy]ethoxyacetyl-Glu-Ser-Nle-c[Glu-Hyp-D-Phe-Arg-Trp-Lys]-NH2
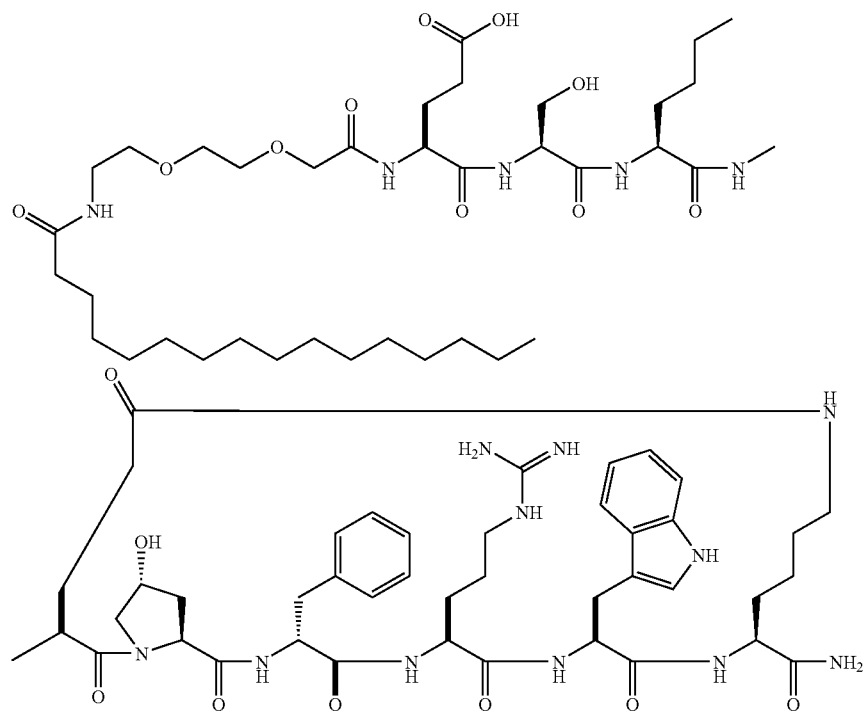
LC/MS (system 1): Rt=4.57 min; (m+1)=1572
Example 47
2-[2-(2-{2-[2-(Dodecanoylamino)ethoxy]ethoxy}acetylamino)ethoxy]ethoxyacetyl-Nle-c[Glu-Hyp-D-Phe-Arg-Trp-Lys]-NH2
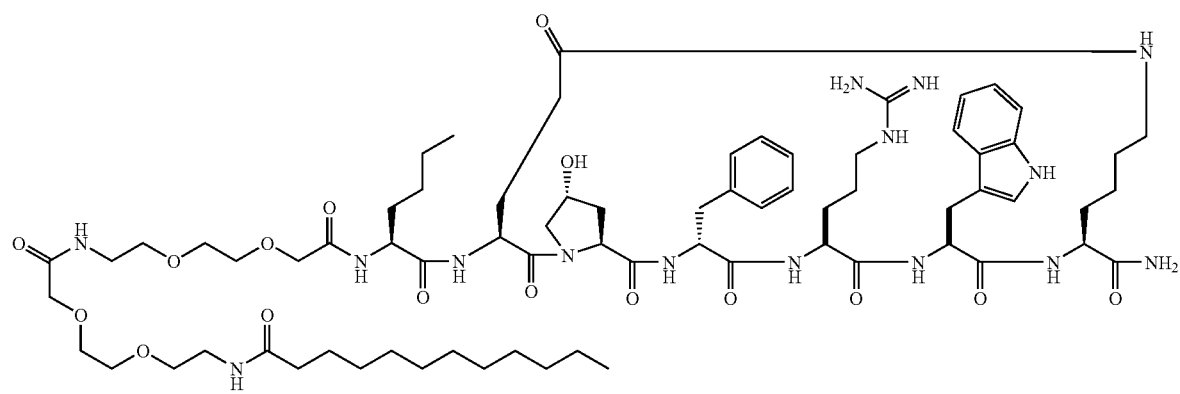
LC/MS (system 1): Rt=3.90 min; (m+1)=1445, ((m+2)/2) =723

Example 48
2-{2-[4-Carbamoyl-2-(2-(hexadecanoylamino)acetylamino)butyrylamino]ethoxy}ethoxyacetyl-Nle-c[Glu-Hyp-D-Phe-Arg-Trp-Lys]-NH2
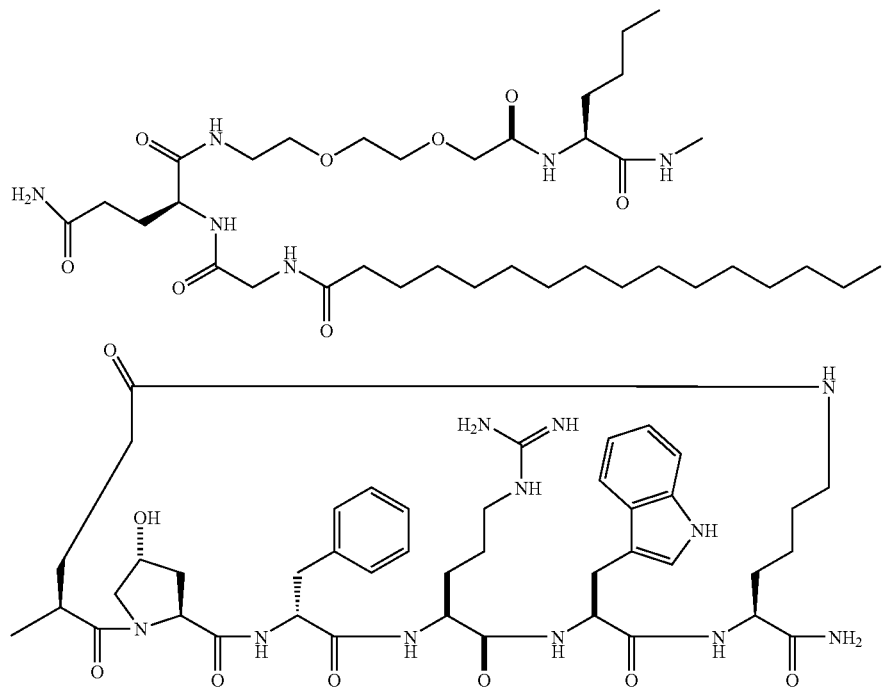
LC/MS (system 1): Rt=4.51 min; (m+1)=1541
Example 49
2-{2-[4-Carboxy-2-(2-hexadecanoylamino)acetylamino)butyrylamino]ethoxy}ethoxyacetyl-Nle-c[Glu-Hyp-D-Phe-Arg-Trp-Lys]-NH2
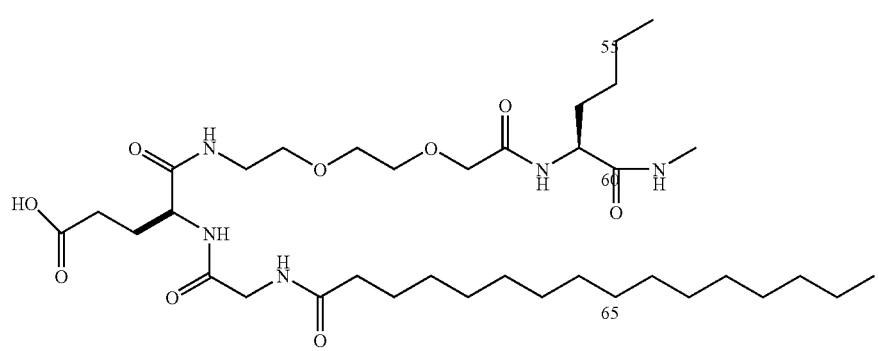

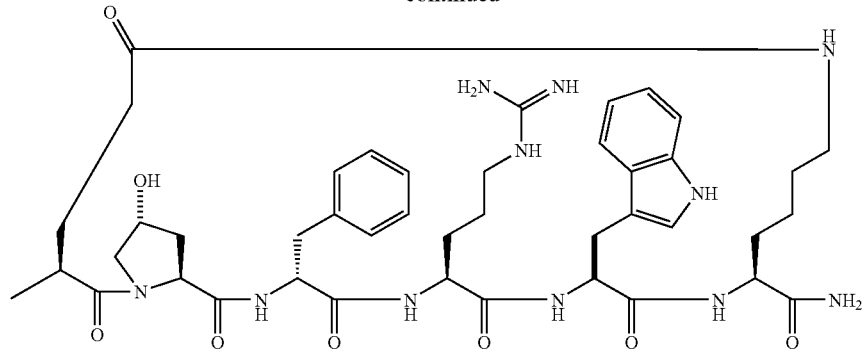
LC/MS (system 1): Rt=4.59 min; (m+1)=1542
Example 50
2-{2-[2-(2-(Hexadecanoylamino)acetylamino)-3-(imidazol-4-yl)propionylamino]ethoxy}ethoxyacteyl-Nle-c[Glu-Hyp-D-Phe-Arg-Trp-Lys]-NH2
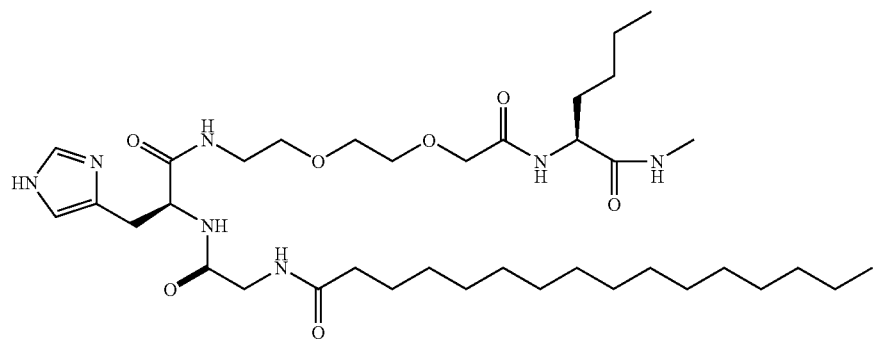
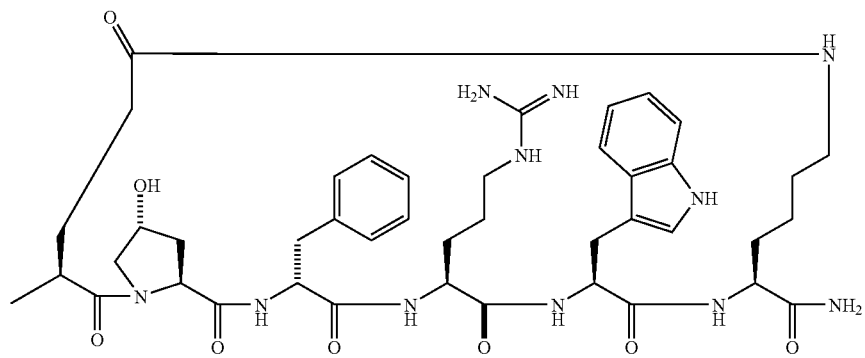
LC/MS (system 1): Rt=4.33 min; (m+1)=1550

Example 51
Dodecanoyl-Nle-c[Glu-Hyp-D-Phe-Arg-Trp-Lys]-NH2
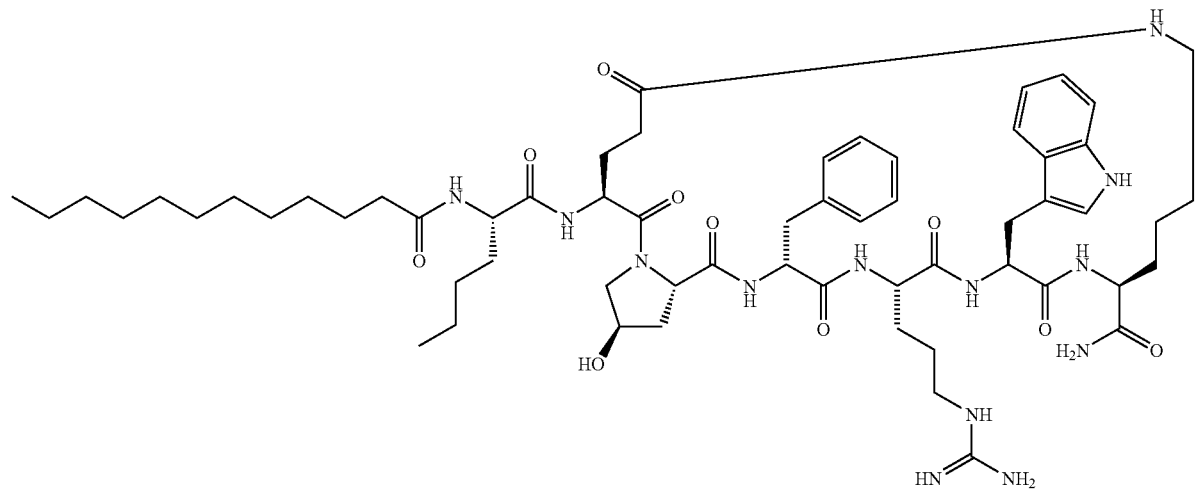
LC/MS (system 2): Rt=4.60 min; (m+1)=1155
Example 52
Hexadecanoyl-Gly-Thr-Asn-Asn-Thr-Nle-c[Glu-Hyp-D-Phe-Arg-Trp-Lys]-NH2
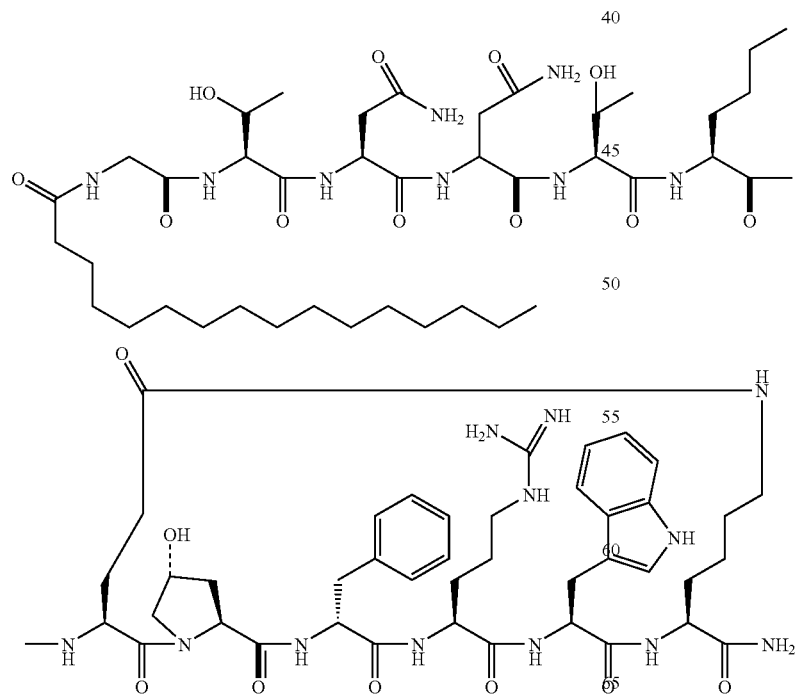

Example 53
Octanoyl-Gly-Ser-D-Gln-His-Thr-Nle-c[Glu-Hyp-D-
Phe-Arg-Trp-Lys]-NH2
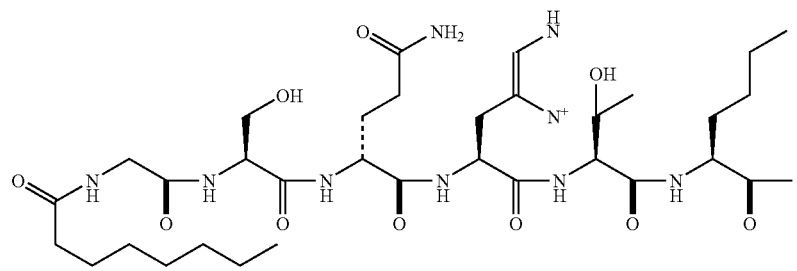
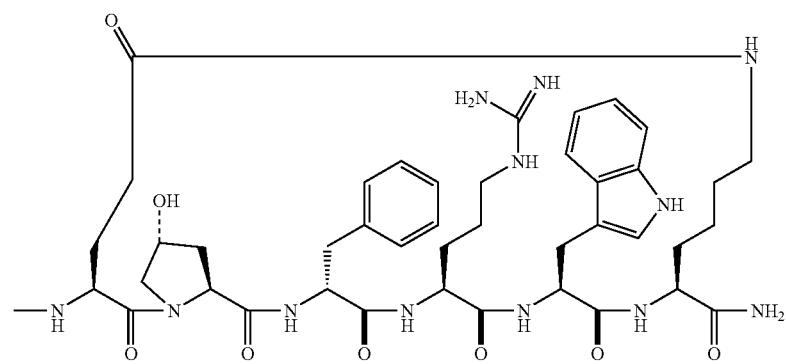
LC/MS (system 1): Rt=2.76 min; ((m+2)/2)=805
Example 54
Decanoyl-Gly-Ser-D-Gln-His-Thr-Nle-c[Glu-Hyp-
D-Phe-Arg-Trp-Lys]-NH2
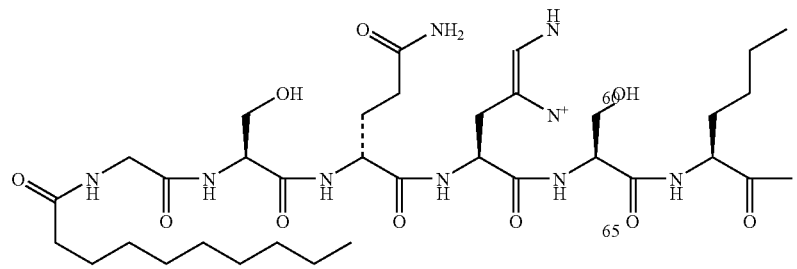

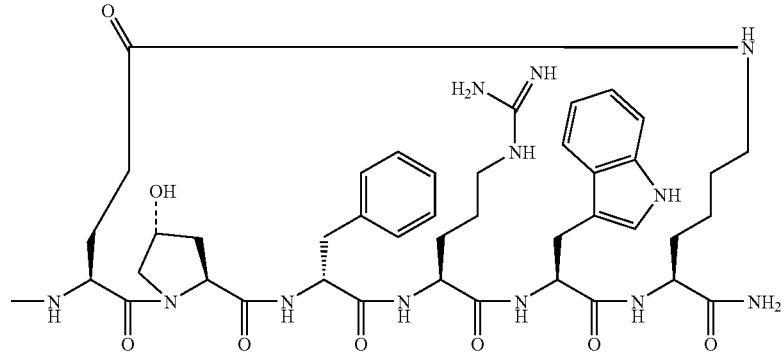
LC/MS (system 4): Rt=8.83 min; ((m+2)/2)=819
Example 55
Dodecanoyl-Gly-Ser-D-Gln-His-Thr-Nle-c[Glu-Hyp-D-Phe-Arg-Trp-Lys]-NH2
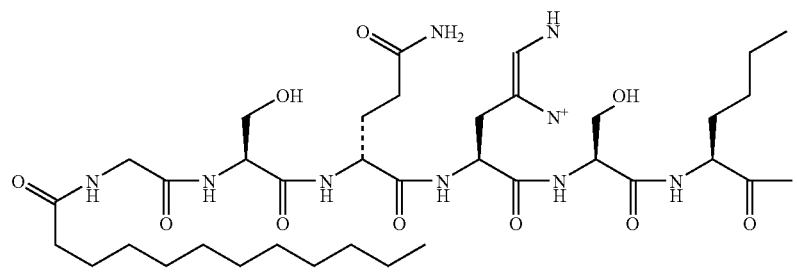
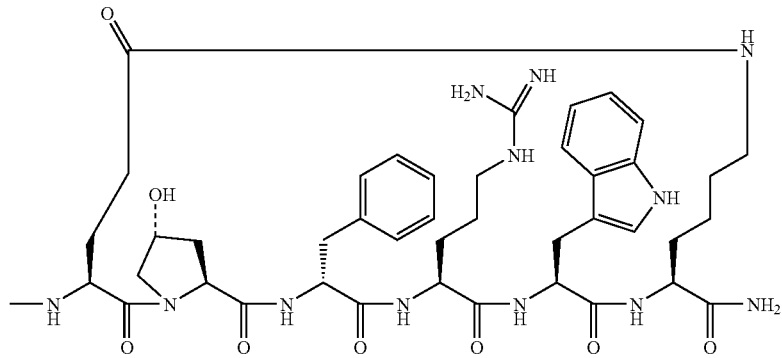
LC/MS (system 4): Rt=10.63 min; ((m+2)/2)=834

Example 56
Tetradecanoyl-Gly-Ser-D-Gln-His-Thr-Nle-c[Glu-Hyp-D-Phe-Arg-Trp-Lys]-NH2
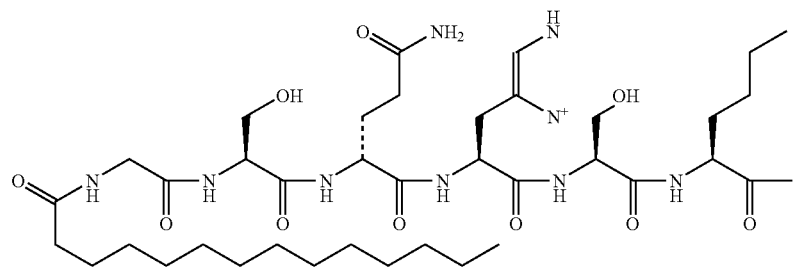
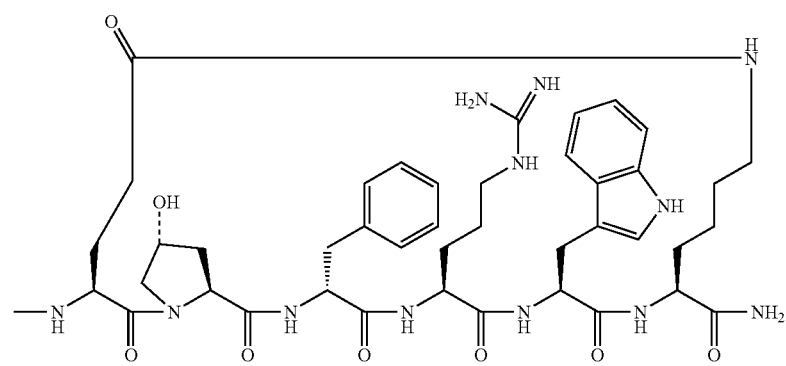
LC/MS (system 4): Rt=12.06 min; ((m+2)/2)=848
Example 57
Hexadecanoyl-Gly-Ser-D-Gln-His-Thr-Nle-c[Glu-Hyp-D-Phe-Arg-Trp-Lys]-NH2
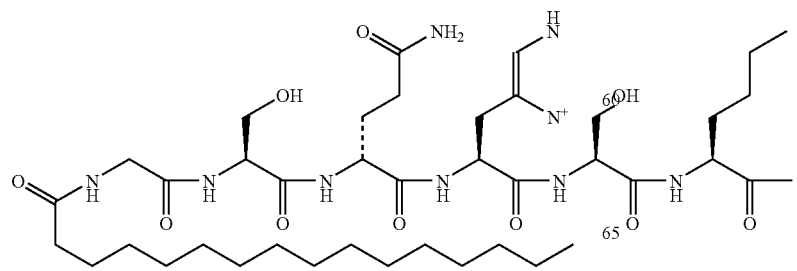

-continued
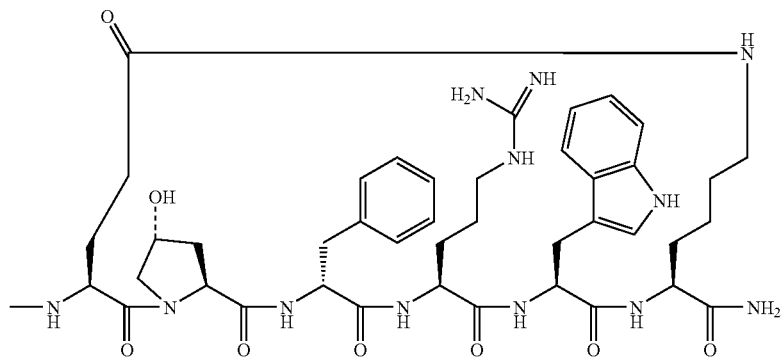
LC/MS (system 4): Rt=13.69 min; ((m+2)/2)=862
Example 58
Octadecanoyl-Gly-Ser-D-Gln-His-Thr-Nle-c[Glu-Hyp-D-Phe-Arg-Trp-Lys]-NH2
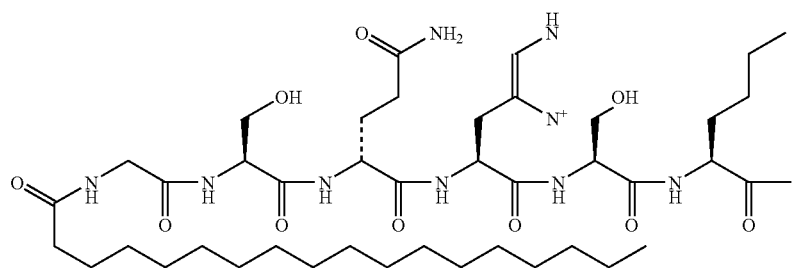
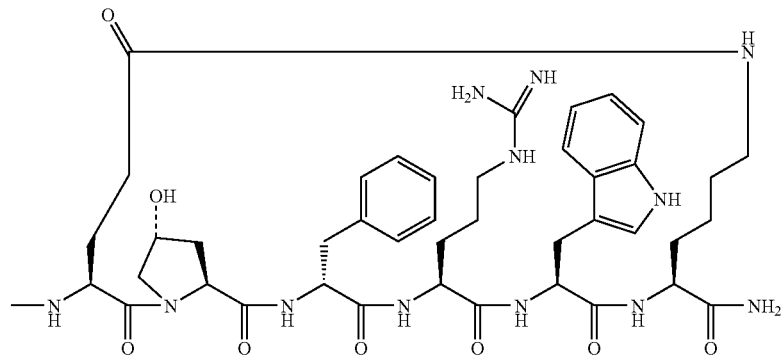
LC/MS (system 4): Rt=15.20 min; ((m+2)/2)=875

Example 59
Hexadecanoyl-Gly-Ser-Gln-His-Ser-Nle-c[Glu-F-
Pro-D-Phe-Arg-Trp-Lys]-NH2
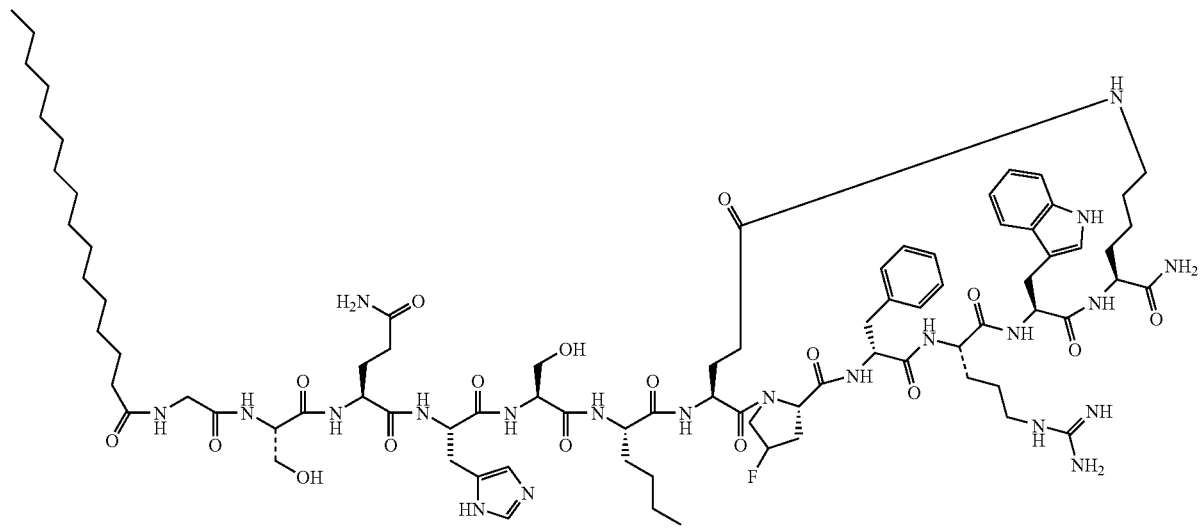
LC/MS (system 3): Rt=26.08 min; ((m+2)/2)=856
Example 60
Hexadecanoyl-Gly-Ser-Gln-homoArg-Ser-Nle-c
[Glu-F-Pro-D-Phe-Arg-Trp-Lys]-NH2
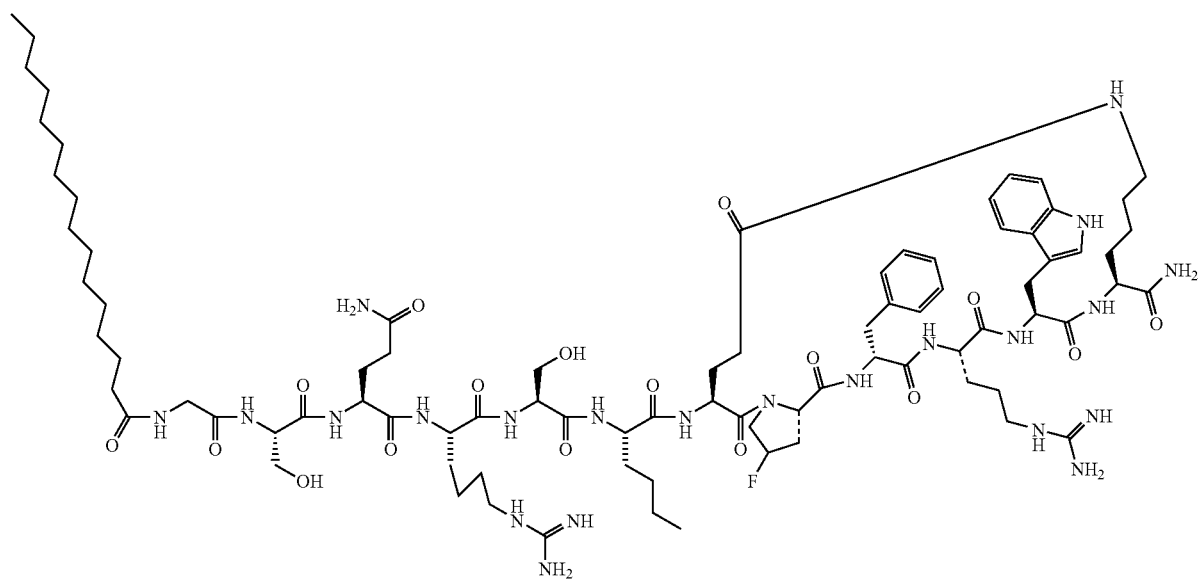
LC/MS (system 3): Rt=25.72 min; ((m+2)/2)=873

Example 61
Hexadecanoyl-Gly-Ser-Gln-homoArg-Thr-Nle-c
[Glu-F-Pro-D-Phe-Arg-Trp-Lys]-NH2
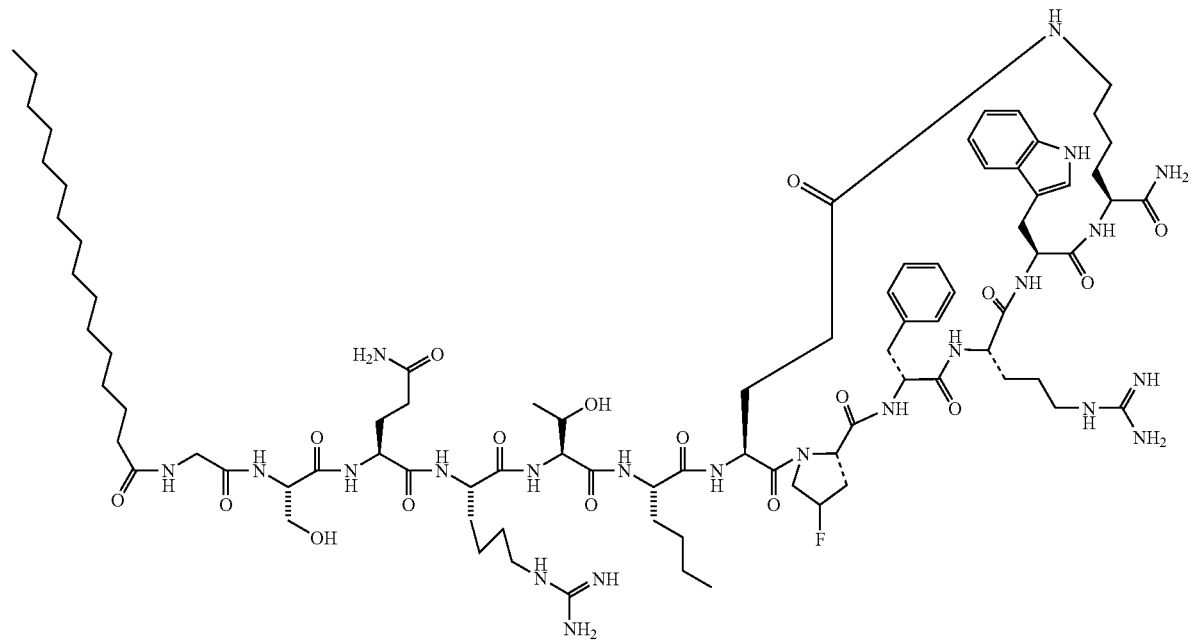
LC/MS (system 3): Rt=26.14 min; ((m+2)/2)=878
Example 62
Hexadecanoyl-Gly-Ser-Asn-homoArg-Thr-Ser-Nle-c
[Glu-F-Pro-D-Phe-Arg-Trp-Lys]-NH2
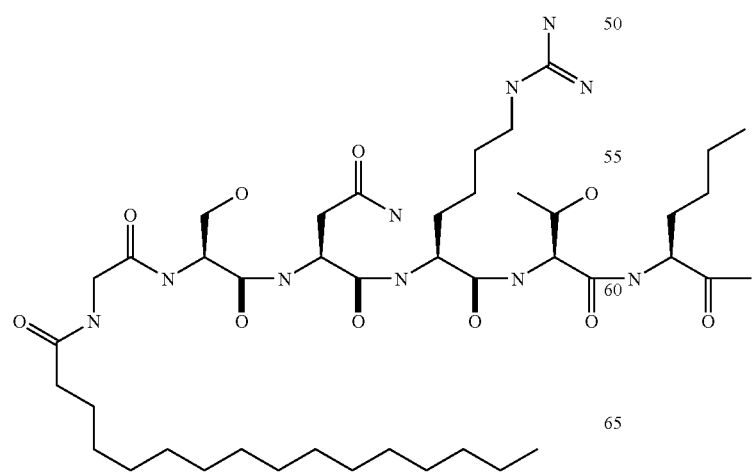

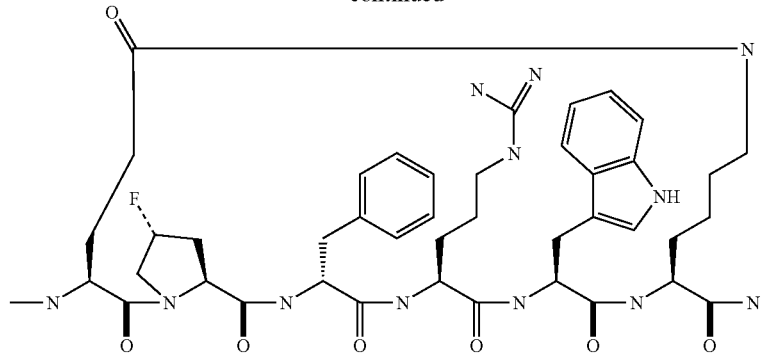
LC/MS (system 3): Rt=26.30 min; ((m+2)/2)=873
Example 63
3-{2-[2-(2-{2-[4-(4,4,5,5,6,6,7,7,8,8,9,9,9-Tridecafluorononanoylsulfamoyl)butyrylamino]ethoxy}ethoxy)ethoxy]ethoxy}propionyl-Gly-Ser-Gln-homoArg-Nle-c[Glu-Hyp-D-Phe-Arg-Trp-Lys]-NH2
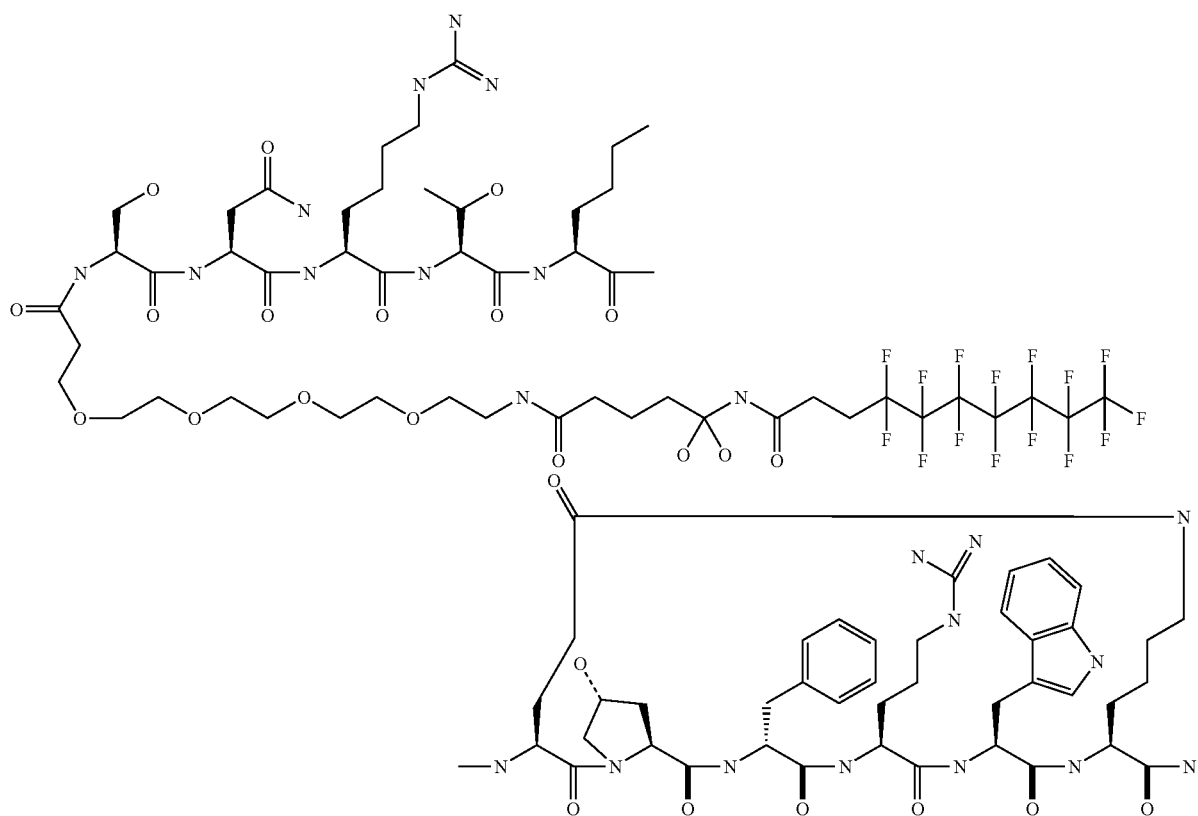
LC/MS (system 3): Rt=18.12 min; ((m+2)/2)=1137

Example 64
Hexadecanoyl-Gly-Ser-Ser-Tyr-Thr-Nle-c[Glu-Hyp-
D-Phe-Arg-Trp-Lys]-NH2
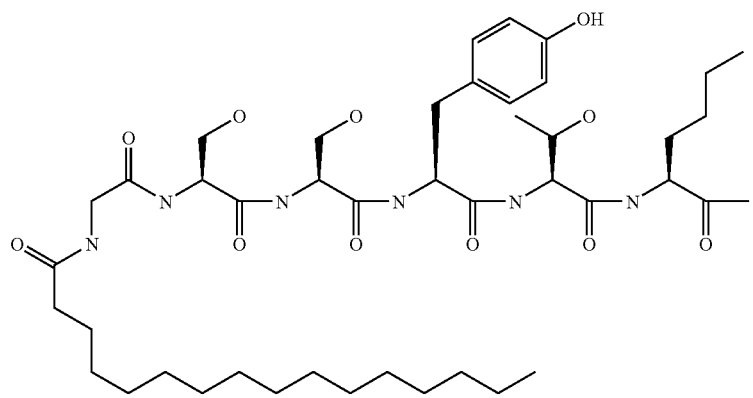
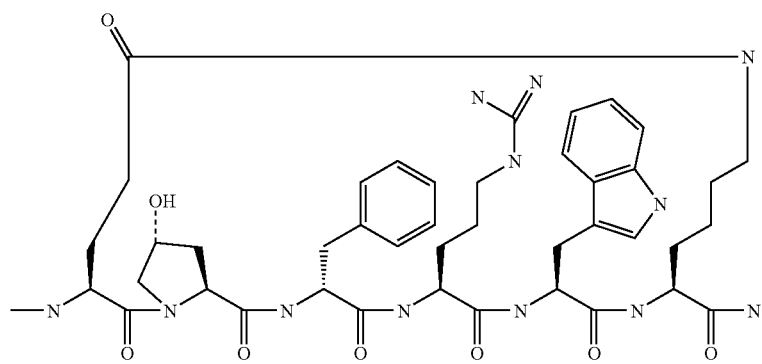
LC/MS (system 3): Rt=28.69 min; ((m+2)/2)=855
Example 65
Hexadecanoyl-Gly-Ser-Asn-Asn-Thr-Nle-c[Glu-
Hyp-D-Phe-Arg-Trp-Lys]-NH2
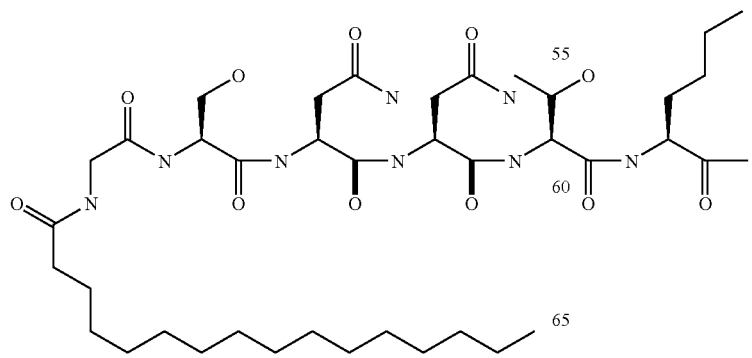

-continued
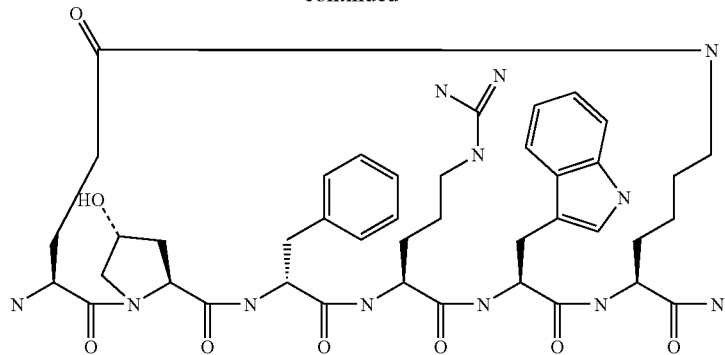
LC/MS (system 3): Rt=26.95 min; ((m+2)/2)=842
Example 66
Hexadecanoyl-Gly-Ser-Ser-homoArg-Thr-Nle-c
[Glu-Hyp-D-Phe-Arg-Trp-Lys]-NH2
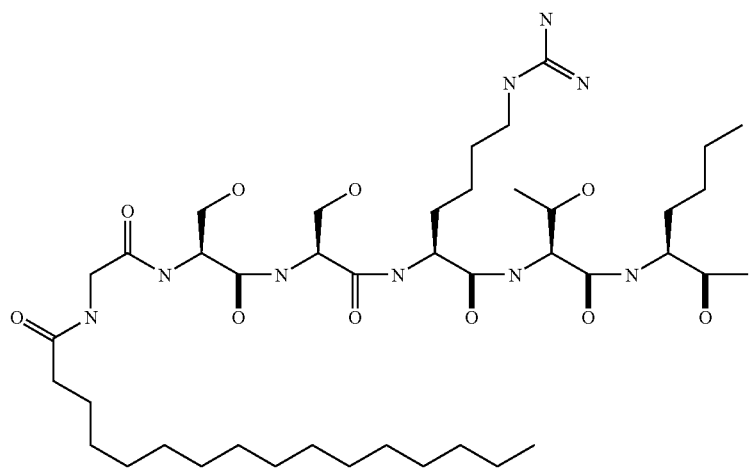
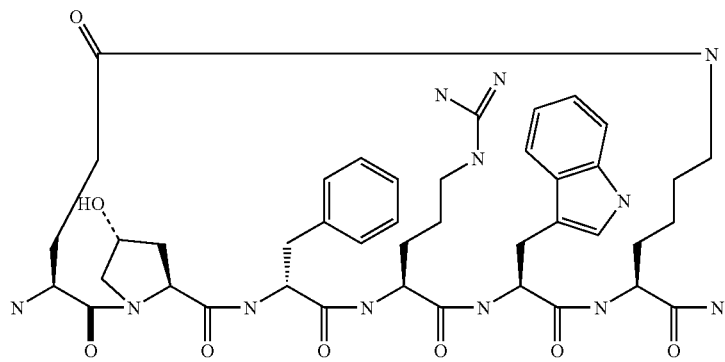
LC/MS (system 3): Rt=25.25 min; ((m+2)/2)=857

Example 67
Hexadecanoyl-Gly-Ser-Ser-His-Thr-Nle-c[Glu-Hyp-
D-Phe-Arg-Trp-Lys]-NH2
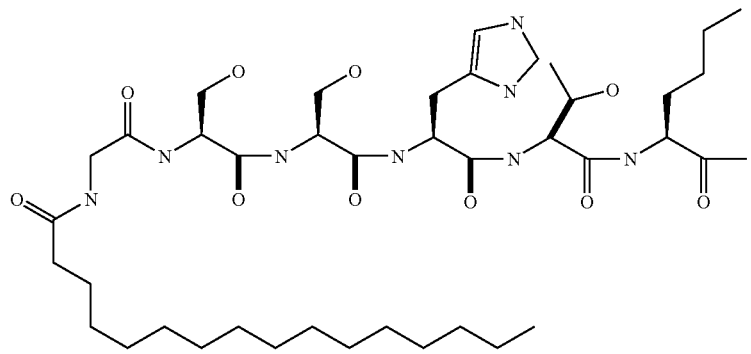
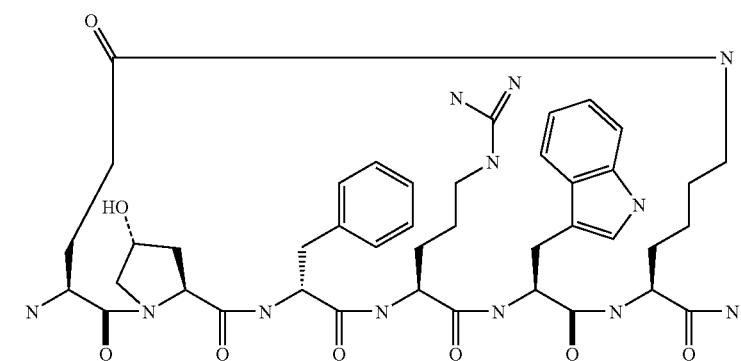
LC/MS (system 3): Rt=24.70 min; ((m+2)/2)=841
Example 68
Hexadecanoyl-Gly-Ser-D-Asn-His-Thr-Nle-c[Glu-
Hyp-D-Phe-Arg-Trp-Lys]-NH2
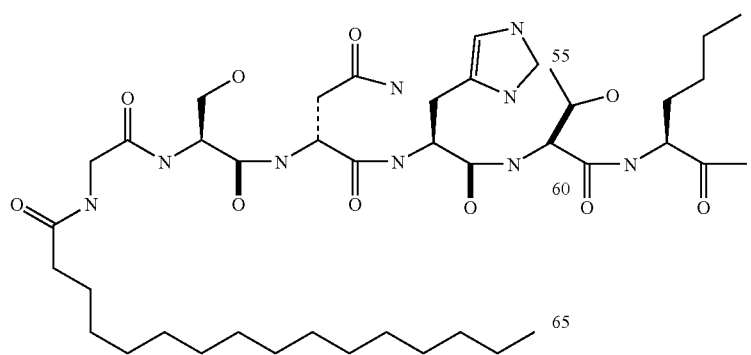

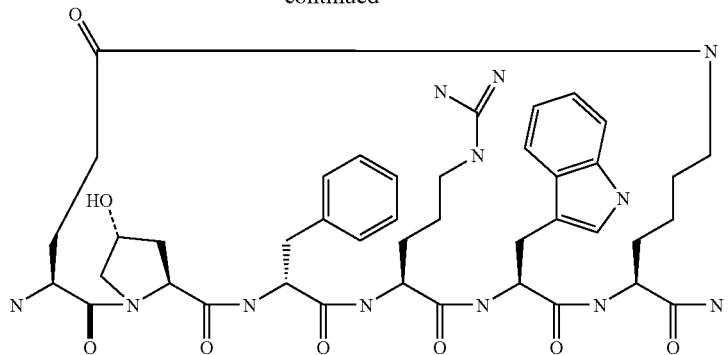
LC/MS (system 3): Rt=24.40 min; ((m+2)/2)=854
Example 69
Hexadecanoyl-Gly-Ser-Asn-homoArg-Thr-Nle-c[Glu-Hyp-D-Phe-Arg-Trp-Lys]-NH2
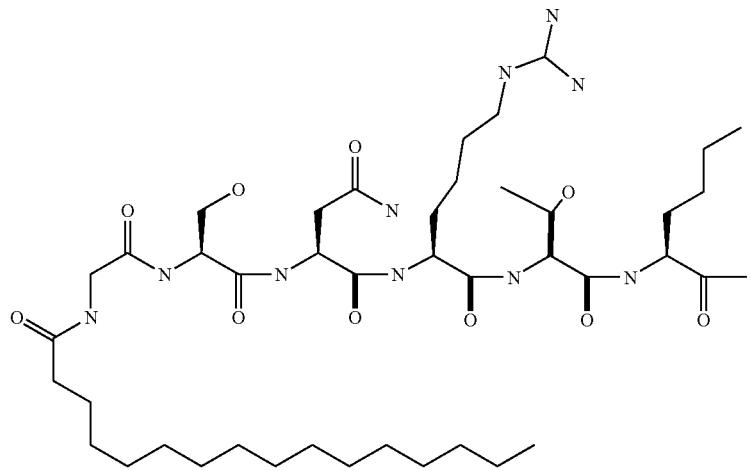
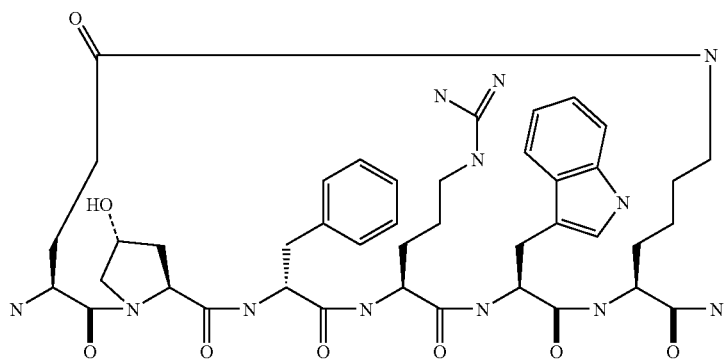
LC/MS (system 3): Rt=24.57 min; ((m+2)/2)=871

Example 70
Hexadecanoyl-Ser-homoArg-Ser-Nle-c[Glu-Met(O2)-D-Phe-Arg-Trp-Lys]-NH2
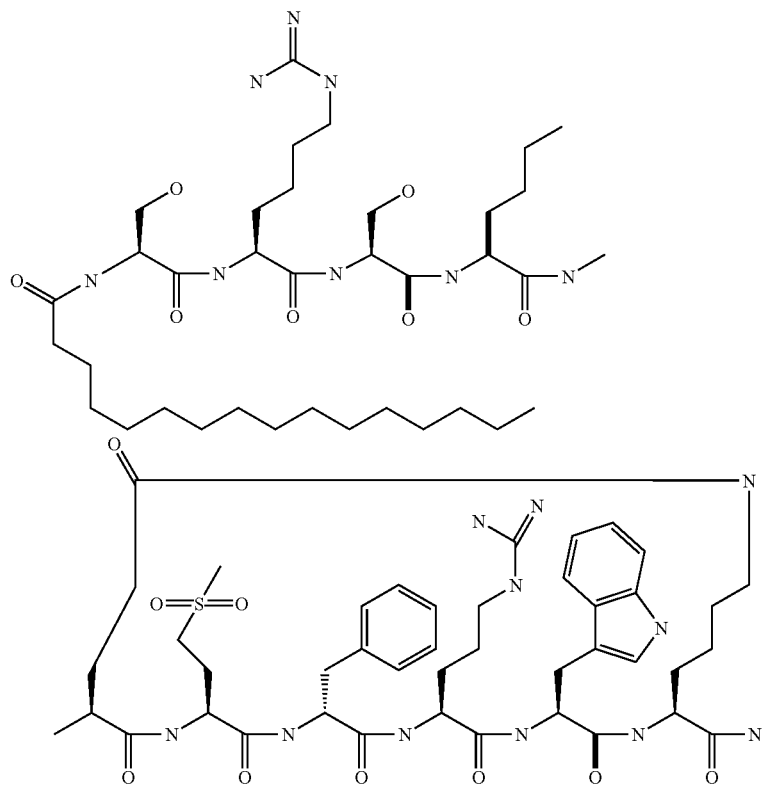
LC/MS (system 3): Rt=26.37 min; ((m+2)/2)=804
Example 71
Hexadecanoyl-Gln-homoArg-Thr-Nle-c[Glu-Met(O2)-D-Phe-Arg-Trp-Lys]-NH2
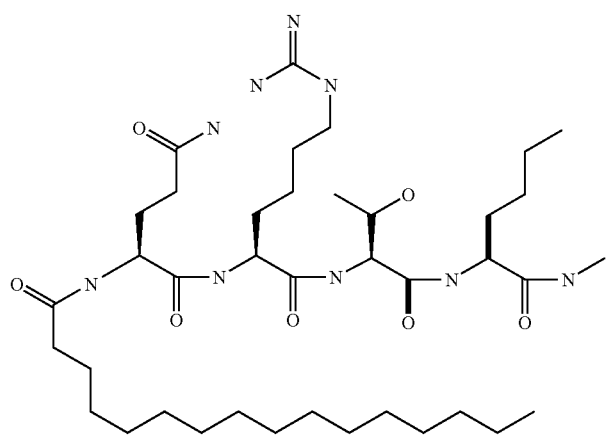

-continued
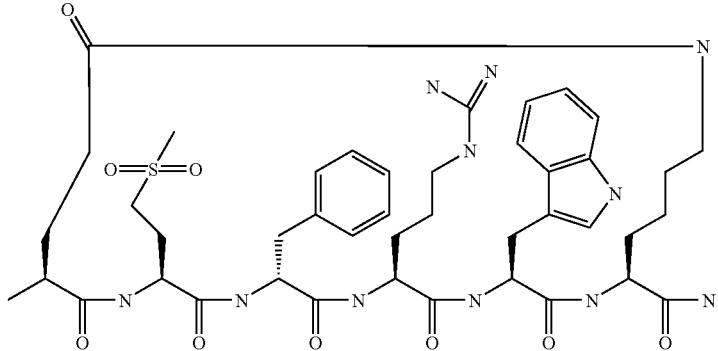
LC/MS (system 3): Rt=25.92 min; ((m+2)/2)=831
Example 72
Hexadecanoyl-Ser-homoArg-Thr-Nle-c[Glu-Met(O2)-D-Phe-Arg-Trp-Lys]-NH2
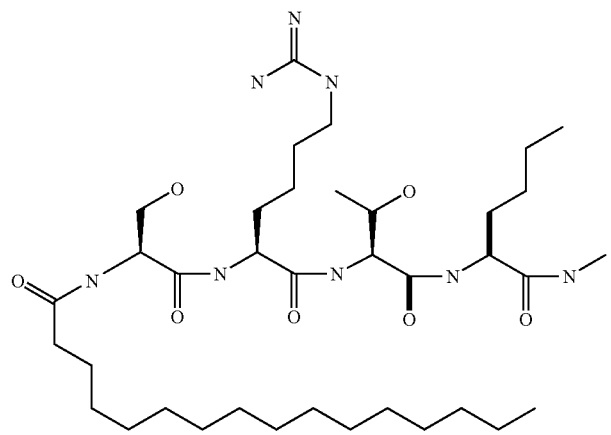
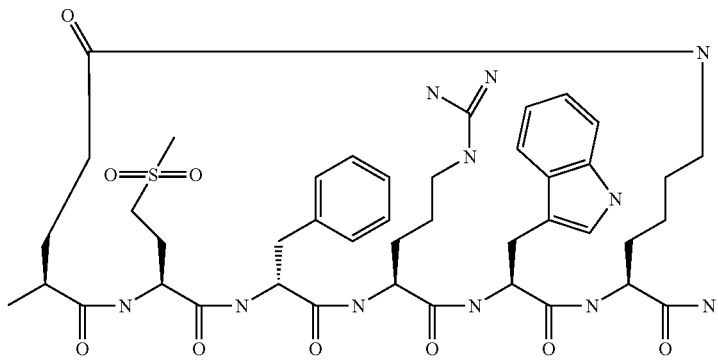
LC/MS (system 3): Rt=26.73 min; ((m+2)/2)=810

Example 73
Hexadecanoyl-Ser-His-Thr-Nle-c[Glu-Met(O2)-D-
Phe-Arg-Trp-Lys]-NH2
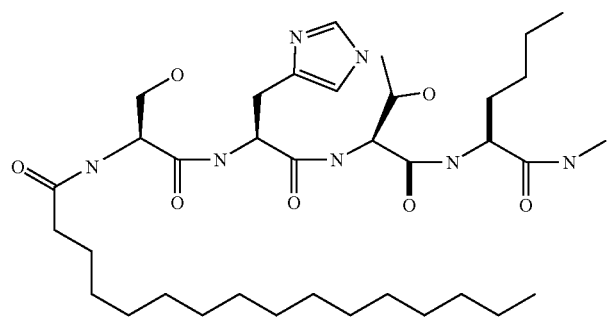
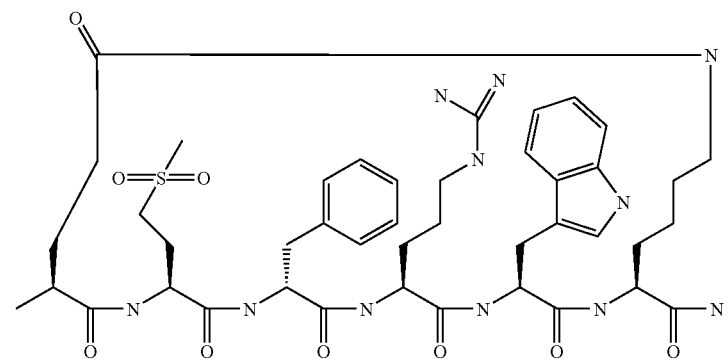
LC/MS (system 3): Rt=26.28 min; ((m+2)/2)=793
Example 74
Hexadecanoyl-Ser-homoArg-Thr-Nle-c[Glu-Met
(O2)-D-Phe-Arg-Trp-Lys]-NH2
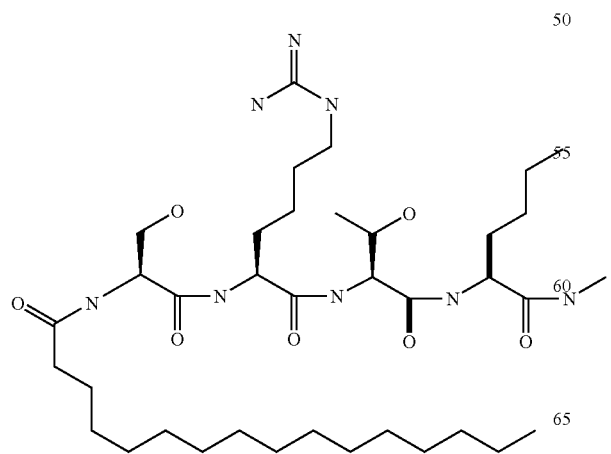

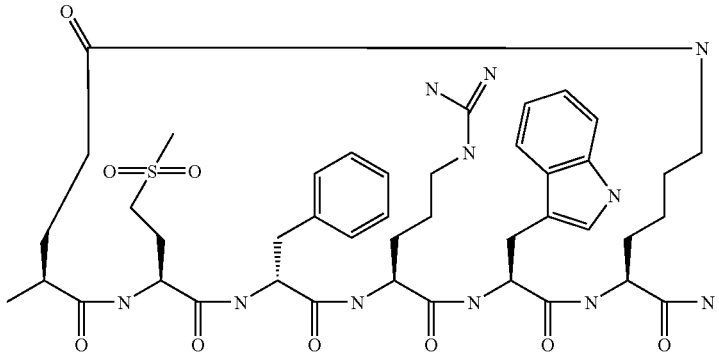

LC/MS (system 3): Rt=26.70 min; ((m+2)/2)=811

Preparation of 4-[2-(3-benzoylphenyl)propionylsulfamoyl]butyric Acid to be Used for the Synthesis of the Compound Above Named as Example 24

Step 1:

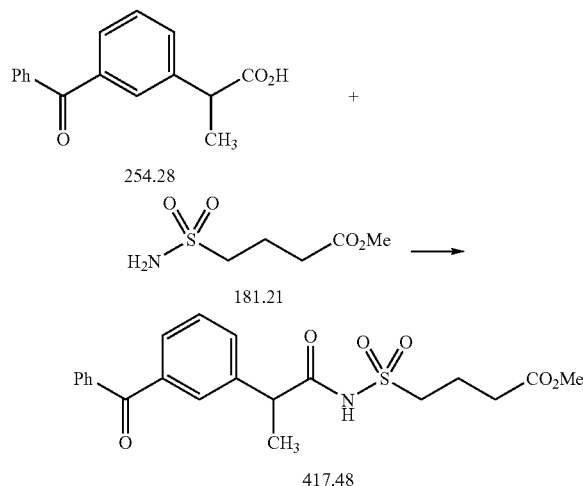

To a solution of ketoprofen (2.66 g, 10.5 mmol) in THF (30 ml) was added carbonyldiimidazole (1.94 g, 12.0 mmol). The solution was stirred at room temperature for 20 h and then heated to 60° C. for 0.5 h. Then a solution of 4-sulfamoylbutyric acid methyl ester (1.74 g, 9.60 mmol) in THF (10 ml) was added, followed by DBU (1.70 ml, 11.4 mmol). The mixture was stirred at 60° C. for 25 h, concentrated, and the residue was mixed with water (100 ml) and 1N aqueous hydrochloric acid (50 ml). Extraction (2×AcOEt), washing of the extracts with brine (1×) and satd aq. $NaHCO_3$ (1×), drying ($MgSO_4$), and concentration yielded 2.30 g of an oil, which was purified by column chromatography (45 g $SiO_2$, gradient elution with heptane to heptane/AcOEt 1:1) to yield 1.20 g (30%) of the title ester as an oil.

$^1$H NMR (DMSO-$d_6$): δ 1.49 (d, J=7 Hz, 3H), 1.76 (m, 2H), 2.39 (t, J=7 Hz, 2H), 3.38 (t, J=7 Hz, 2H), 3.55 (s, 3H), 3.86 (quart, J=7 Hz, 1H), 7.51-7.76 (m, 9H), 11.90 (s, 1H).

Step 2: Saponification

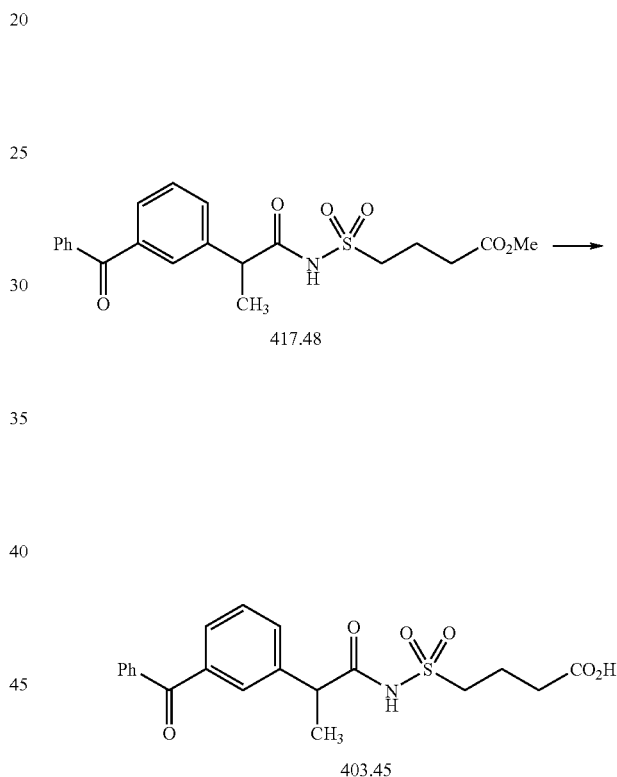

To a solution of this ester (0.73 g, 1.75 mmol) in methanol (5.0 ml) was added a solution of NaOH (0.40 g, 10 mmol) in water (1.0 ml). The mixture was stirred at room temperature for 3 h, and then diluted with 1N aqueous hydrochloric acid (10 ml) and water (50 ml). Extraction (3×AcOEt), washing (2×brine), drying (MgSO4), and concentration yielded 0.65 g (92%) of the title acid as a foam, which was crystallized from AcOEt/heptane. M.p.: 137-138° C.

$^1$H NMR (DMSO-$d_6$): δ 1.39 (d, J=7 Hz, 3H), 1.76 (m, 2H), 2.32 (t, J=7 Hz, 2H), 3.37 (t, J=7 Hz, 2H), 3.88 (quart, J=7 Hz, 1H), 7.51-7.76 (m, 9H), 11.88 (s, 1H), 12.21 (br s, 1H).

Preparation of 4-(hexadecanoylsulfamoyl)butyric Acid to be Used for the Syntheses of the Compounds Above Named as Examples 23, 30 and 33

$^1$H NMR (DMSO-d$_6$): δ 0.85 (m, 3H), 1.23 (br s, 24H), 1.49 (m, 2H), 1.85 (m, 2H), 2.25 (t, J=7 Hz, 2H), 2.39 (t, J=7Hz, 2H), 3.38 (m, 2H), 11.15 (s, 1H).

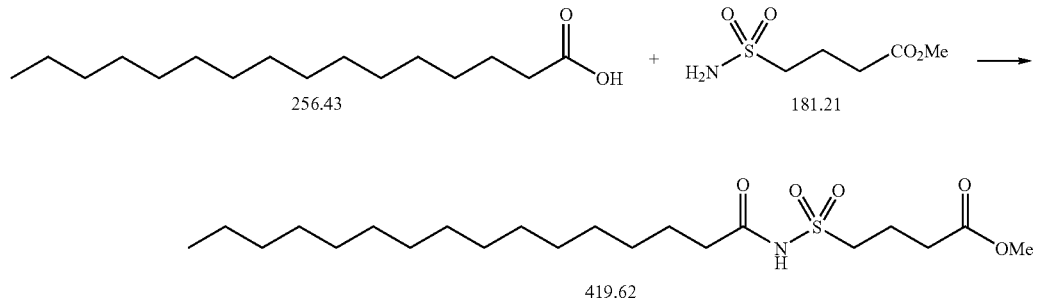

Step 1:

To a suspension of palmitic acid (1.67 g, 6.51 mmol) in toluene (6.0 ml) was added oxalyl chloride (0.56 ml, 6.53 mmol). After 45 min the resulting clear solution was added to a flask containing 4-sulfamoylbutyric acid methyl ester (0.91 g, 5.02 mmol), and the mixture was diluted with DCM (5.0 ml). To this mixture was added 4-dimethylaminopyridine (DMAP, 1.90 g, 15.5 mmol) in small portions. The mixture was stirred at room temperature for 19 h. A mixture of water (100 ml) and 1N HCl (20 ml) was added, followed by extraction with AcOEt/DCM, washing of the combined extracts with brine, drying (MgSO4), and concentration under reduced pressure. The resulting solid (2.26 g) was recrystallized from hot AcOEt (approx 10 ml), to yield 1.59 g (76%) of the methyl ester as almost colorless solid, mp: 100-103° C.

$^1$H NMR (DMSO-d$_6$): δ 0.84 (m, 3H), 1.23 (br s, 24H), 1.49 (m, 2H), 1.88 (m, 2H), 2.24 (t, J=7 Hz, 2H), 2.49 (t, J=7 Hz, 2H), 3.38 (m, 2H), 3.59 (s, 3H), 11.58 (s, 1H).

Step 2: Saponification

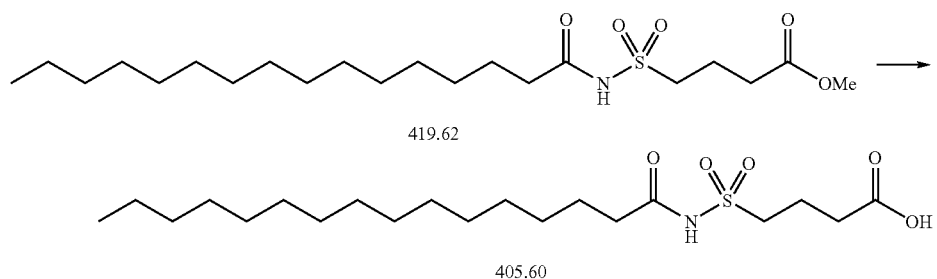

To a suspension of the methyl ester (0.84 g, 2.00 mmol) in methanol (10 ml) was added a solution of NaOH (0.54 g, 13.5 mmol) in water (1.0 ml). The mixture was stirred at room temperature for 4 h. A mixture of water (30 ml) and 1N HCl (20 ml) was added, and the product was isolated by filtration. Recrystallization from boiling MeCN (50 ml) yielded 0.64 g (79%) of the title compound as colorless plates. M.p.: 156-157° C.

4-(4,4,5,5,6,6,7,7,8,8,9,9,9-Tridecafluorononanoyl-sulfamoyl)butyric Acid to be Used for the Synthesis of the Compound Above Named as Example 63

Step 1:

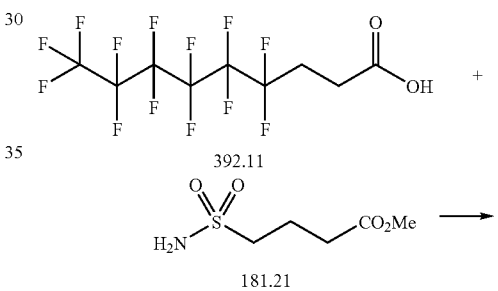

-continued 4,4,5,5,6,6,7,7,8,8,9,9,9-Tridecafluorononanoic acid (3.07 g, 7.83 mmol) was mixed with thionyl chloride (20 ml) and stirred at 80 oC for 1.5 h. The mixture was concentrated and the residue stripped once with toluene. The residual liquid was dissolved in DCM (5 ml) and this solution was added to a solution of 4-sulfamoylbutyric acid methyl ester (1.15 g, 6.35 mmol) in DCM (5 ml). To this mixture DMAP (2.34 g, 19.3 mmol) was added in small portions while stirring energically. During the addition the mixture became viscous, and more DCM (10 ml) was added. The resulting mixture was stirred at room temperature for 66 h, whereby it turned black. A mixture of water (100 ml) and 1N HCl (30 ml) was added, and the product was extracted (3×AcOEt; emulgates strongly at the beginning). The combined extracts were washed (2×brine), dried (MgSO4), and concentrated under reduced pressure to yield 3.14 g of a pink solid. Recrystallization from AcOEtheptane yielded 1.83 g (52%) of the methyl ester as slightyl pink solid, m.p. 143-145° C.

$^1$H NMR (DMSO-d$_6$): δ 1.91 (m, 2H), 2.47-2.62 (m, 4H), 2.67 (m, 2H), 3.41 (m, 2H), 3.59 (s, 3H), 11.87 (s, 1H).

Step 2: Saponification

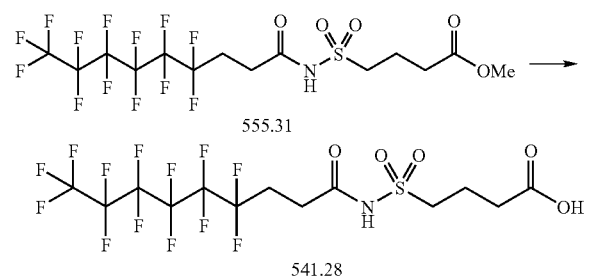

To a suspension of the methyl ester (1.11 g, 2.0 mmol) in MeOH (7.0 ml) was added a solution of NaOH (0.54 g, 13.5 mmol) in water (1.0 ml). The mixture was stirred at room temperature for 3 h 15 min. A mixture of water (30 ml) and 1N HCl (20 ml) was added, and the product was isolated by filtration. Recrystallization from MeCN (approx 5 ml) at –20° C. yielded 0.77 g (71%) of the title acid as colorless solid. M.p.: 175-180° C.

$^1$H NMR (DMSO-d$_6$): δ 1.88 (m, 2H), 2.38 (t, J=7 Hz, 2H), 2.45-2.62 (m, 2H), 2.66 (m, 2H), 3.39 (m, 2H), 11.85 (s, 1H), 12.24 (s, 1H).

Pharmocological Methods

Assay (I) Experimental Protocol for Efficacy Testing on Appetite with MC4 Analogues, Using a Ad Libitum Fed Rat Model.

TAC:SPRD @mol rats or Wistar rats from M&B Breeding and Research Centre A/S, Denmark are used for the experiments. The rats have a bodyweight 200-250 g at the start of experiment. The rats arrive at least 10-14 days before start of experiment with a bodyweight of 180-200 g. Each dose of compound is tested in a group of 8 rats. A vehicle group of 8 rats is included in each set of testing.

When the animals arrive they are housed individually in a reversed light/dark phase (lights off 7:30 am, lights on 7:30 pm), meaning that lights are off during daytime and on during nighttime. Since rats normally initiate food intake when light go off and eat the major part of their daily food intake during night, this set up means that we have reversed the initiation time of food intake till 7:30, when lights go off. During the habituating period of 10-14 days, the rats have free access to food and water, In this period the animals are handled at least 3 times. The experiment is conducted in the rats' home cages. Immediately before dosing the rats are randomised to the different treatment groups (n=8) by bodyweight. They are dosed according to bodyweight at between 7:00 am, with a 1-3 mg/kg solution either, ip, po or sc. The dosing time is recorded for each group. Following dosing the rats are returned to their home cages, where they now have access to food and water. The food consumption is recorded individually, each hour for 7 hours, and then after 24 h and sometimes 48 h. At the end of the experimental session, the animals are euthanised.

The individual data are recorded in Microsoft excel sheets. Outliers are excluded after using the Grubbs statistical evaluation test for outliers and the result presented graphically by using the GraphPad Prism program.

Assay (II) Melanocortin Receptor 3 and 5 (MC3 and MC5) cAMP Functional Assay Using the AlphaScreen™ cAMP Detection Kit The cAMP assays for MC3 and MC5 receptors are performed on cells stably expressing the MC3 and MC5 receptors respectively. The receptors were cloned from cDNA by PCR and inserted into the pcDNA 3 expression vector. Stable clones were selected using 1 mg/ml G418.

Cells at app. 80-90% confluence are washed 3× with PBS, lifted from the plates with Versene and diluted in PBS. Centrifuged 2 min at 1300 rpm, and the supernatant removed. The cells are washed twice with stimulation buffer, and resuspended in stimulation buffer to a final concentration of 1 or 2×10$^6$ cells/ml. 25 µl cell suspension is added to the microtiter plates containing 25 µl of test-compound or reference compound (all diluted in stimulation buffer). The plates are incubated for 30 minutes at room temperature (RT) on a plate-shaker that shakes at low rate. The reaction is stopped by adding and 25 µl acceptor beads with anti-cAMP and 2 min later 50 µl donor beads per well with biotinylated cAMP in a lysis buffer. The plates are then sealed with plastic, shaken for 30 minutes, and allowed to stand overnight, and counted in the Alpha™ microplate reader.

EC$_{50}$ values are calculated by non-linear regression analysis of dose response curves (6 points minimum) using the windows program GraphPad Prism, GraphPad software, USA. All results are expressed in nM.

For measuring antagonistic activity in the MC3 functional cAMP assay the MC3 receptors are stimulated with 3 nM α-MSH, and inhibited by increasing amount of potential antagonist. The IC$_{50}$ value of the antagonist is defined at the concentration that inhibits MC3 stimulation by 50%.

Assay (III) Melanocortin Receptor 4 (MC4) cAMP Assay

BHK cells expressing the MC4 receptor are stimulated with potential MC4 agonists, and the degree of stimulation of cAMP is measured using the Flash Plate® cAMP assay (NEN™ Life Science Products cat no SMP004).

The MC4 receptor expressing BHK cells were made by transfecting the cDNA encoding MC4 receptor into BHK570/KZ10-20-48, and selecting for stable clones expressing the MC4 receptor. The MC4 receptor cDNA was bought from Euroscreen in addition to a CHO cell line expressing the MC4 receptor. The cells are grown in DMEM, 10% FCS, 1 mg/ml G418, 250 nM MTX and 1% penicillin/streptomycin.

Cells at app. 80-90% confluence are washed 3× with PBS, lifted from the plates with Versene and diluted in PBS. Centrifuged 2 min at 1300 rpm, and the supernatant removed. The cells are washed twice with stimulation buffer, and resuspended in stimulation buffer to a final concentration of 0.75× 10$^6$ cells/ml. (Use 7 ml/96 well plate). 50 µl cell suspension is added to the Flashplate containing 50 µl of test-compound or reference compound (all diluted in H$_2$O). The mixture is shaken for 5 minutes, and allowed to stand for 25 minutes at RT. The reaction is stopped with 100 μl Detection Mix pro well (Detection Mix=11 ml Detection Buffer+100 μl (~2 μCi) cAMP [$^{125}$I] Tracer). The plates are then sealed with plastic, shaken for 30 minutes, and allowed to stand overnight (or for 2 hours), and counted in the Topcounter 2 min/well. In general the assay procedure described in the flash plate kit-protocol (Flash Plate® cAMP assay (NEN™ Life Science Products cat no SMP004)). However the cAMP standards are diluted in 0.1% HSA and 0.005% tween 20 and not in stimulation buffer.

$EC_{50}$ values is calculated by non-linear regression analysis of dose response curves (6 points minimum) using the windows program GraphPad Prism, GraphPad software, USA. All results are expressed in nM.

Assay (IV) Melanocortin Receptor 1 (MC1) Binding Assay

The MC1 receptor binding assay is performed on HEK293 cell membranes stably expressing the MC1 receptor. The assay is performed in a total volume of 250 μl; 25 μl; $^{125}$NDP-α-MSH (22 pM in final concentration) 25 μl test compound/control and 200 μl cell membrane (35 μg/ml). Test-compounds are dissolved in DMSO. Radioligand, membranes and test-compounds are diluted in buffer; 25 mM HEPES pH 7.4, 0.1 mM $CaCl_2$, 1 mM $MgSO_4$, 1 mM EDTA, 0.1% HSA and 0.005% Tween-20. The samples are incubated at 30° C. for 90 min in the Greiner microtiter plates and separated with GF/B filters that are pre-wetted for 60 min in 0.5% PEI, and washed 2-3 times with NaCl (0.9%) before separation of bound from unbound radio ligand by filtration. After filtration the filters are washed with ice-cold 0.9% NaCl 10 times. The filters are dried at 50° C. for 30 min, sealed and 30 μl Microscint 0 (Packard, cat no. 6013616) are added to each well and the plates are counted in a Topcounter 1 min/well.

The data are analysed by a non-linear regression analysis of binding curves, using a windows program GraphPad Prism, GraphPad software, USA.

Assay (V) Melanocortin Receptor 4 (MC4) Binding Assay

In vitro $^{125}$NDP-α-MSH Binding to Recombinant BHK Cells Expressing Human MC4 Receptor (Filtration Assay).

The assay is performed in 5 ml minisorb vials, (Sarstedt No. 55.526) or in 96 well filterplate, Millipore MADVN 6550 and using BHK cells expressing the human MC4 receptor (obtained from Professer Wikberg, Uppsala, Sweden). The BHK cells are kept at −80° C. until assay, and the assays is run directly on a dilution of this cell suspension, without further preparation. The suspension is diluted to give maximal 10% specific binding, app 50-100 fold dilution. The assay is performed in a total volume of 200 μl; 50 μl cell suspension, 50 μl $^{125}$NDP-α-MSH (≈79 pM in final concentration), 50 μl test-peptide and 50 μl binding buffer pH 7 is mixed and incubated for 2 h at 25° C. (Binding buffer; 25 mM HEPES pH 7.0, 1 mM $CaCl_2$, 1 mM $MgSO_4$, 1 mM EGTA, 0.02% Bacitracin and 0.2% BSA). Peptides are dissolved in $H_2O$ and diluted in binding buffer. Radioligand and membranes are diluted in binding buffer. The incubation is stopped by dilution with 5 ml ice-cold 0.9% NaCl, followed by rapid filtration through Whatman GF/C filters pre-treated for 1 hour with 0.5% polyethyleneimine. The filters are washed with 3×5 ml ice-cold NaCl. The radioactivity retained on the filters is counted using a Cobra II auto gamma counter.

The data are analysed by a non-linear regression analysis of binding curves, using a windows program GraphPad Prism, GraphPad software, USA.

Assay (VI) Evaluation of Energy Expenditure

TAC:SPRD rats or Wistar rats from M&B Breeding and Research Centre A/S, Denmark are used. After at least one week of acclimatization, rats are placed individually to the metabolic chambers (Oxymax system, Columbus Instruments, Columbus, Ohio; systems calibrated daily). During the measurement, animals have free access to water, but no food is provided to the chambers. Light:dark cycle is 12:12, lights on at 6.00. After the animals have spent in the chambers ca 2 hours (i.e. when the baseline energy expenditure is reached), compound or vehicle are administrated (po, ip or sc), and recording is continued in order to establish the action time of the compound. Data for each animal (oxygen consumption, carbon dioxide production and flow rate) are collected every 10-18 min for totally 22 hours: 2 hours of adaptation (baseline) and 20 hours of measurement. Correction for the changes in $O_2$ and $CO_2$ content in the flow-in air is done in each 10-18 min cycle.

Data are calculated per metabolic weight ((kg body weight)$^{0.75}$) for oxygen consumption and carbon dioxide production, and per animal for heat. Oxygen consumption ($VO_2$) is regarded as the major energy expenditure parameter of interest.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The invention claimed is:

1. A peptide according to formula I

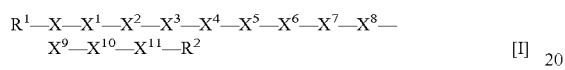

wherein $R^1$, which is bonded to an N-terminal $NH_2$-group, is either absent or represents $C_{1-4}$alkanoyl or $R^4$, which is a protracting group, optionally attached to X via a linker S, wherein $R^4$ represents a straight, branched and/ or cyclic $C_{8-22}$alkanoyl, $C_{8-22}$alkenoyl or $C_{8-22}$alkynoyl, all of which may optionally be substituted with one or more substituents selected from hydroxyl, halogen, carboxyl and aryl, wherein said aryl may optionally be further substituted by one or more substituents selected from hydroxyl, halogen, and carboxyl;

or wherein $R^4$ represents 4-(hexadecanoyl sulfamoyl)butanoyl, or wherein $R^4$ represents $R^5$—C(O)—NH—S(O)$_2$—(CH$_2$)$_3$—C(O)—, wherein $R^5$ represents 1-(4-benzoylphenyl)ethyl or wherein $R^4$ represents a steroid represented by formula II or II a

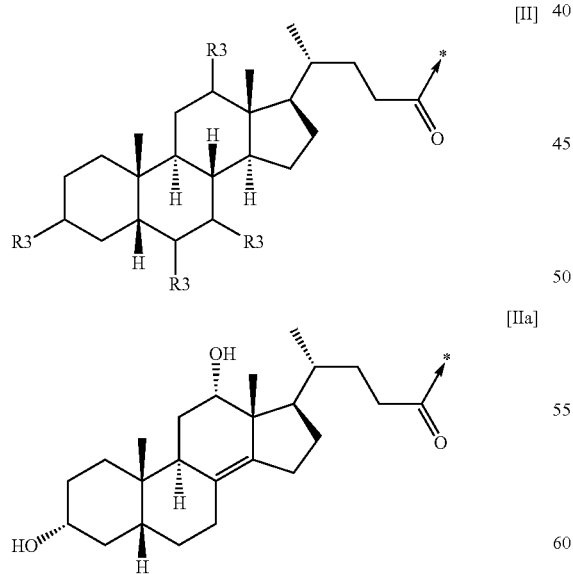

wherein each $R^3$ independently represents hydrogen, hydroxyl or $R^3$ together with the bond which binds it to the ring carbon constitute =O, or wherein $R^4$ represents a structure according to formula III, IIIa, IIIb, IV or IVa

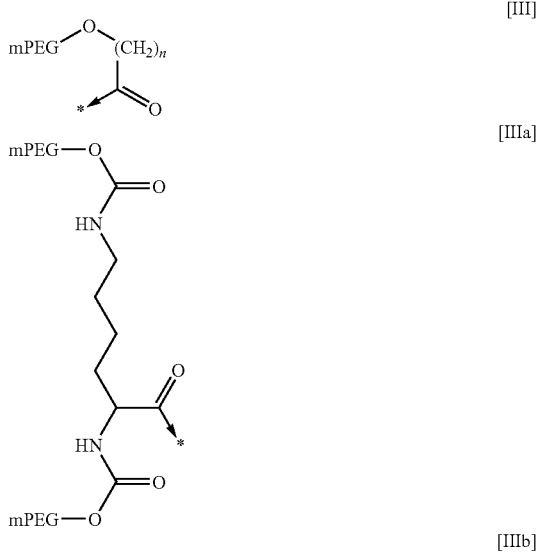

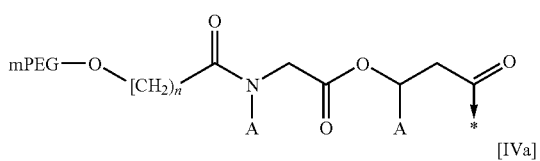

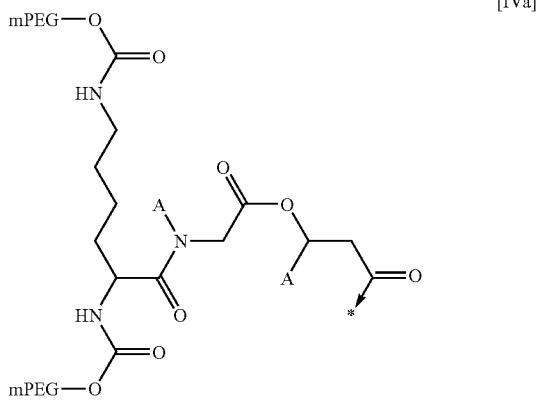

wherein n is 1, 2, or 3, each mPEG independently represents methoxy polyethylene glycol with a molecular weight between about 2 kDa and about 50 kDa, each A independently represents hydrogen or $C_{1-4}$alkyl;

X represents a bond or an amino acid, a di- or tri-peptide residue, wherein the amino acid(s) may be natural or synthetic;

$X^1$ represents a bond or an amino acid residue with a functional group in the side chain to which a protracting group, $R^4$, may be attached, optionally via a linker, S;

$X^2$ represents a bond or an amino acid, di-, tri- or tetra-peptide residue, wherein the amino acid(s) may be natural or synthetic;

$X^3$ represents a bond or an amino acid residue optionally capable of making a bridge to $X^{10}$;

$X^4$ represents a bond or an amino acid or di-peptide residue, wherein the amino acid(s) may be natural or synthetic;

$X^5$ represents an amino acid residue selected from His, Ala, Nle, Met, Met(O), Met(O$_2$), Gln, Gln(ϵ-alkyl), Gln(ϵ-aryl), Asn, Asn(ϵ-alkyl), Asn(ϵ-aryl), Ser, Thr, Cys, F-Pro, Pro, Hyp, (S)-1,2,3,4-tetrahydroisoquinoline-3-carboxylic acid, Trp, 1-naphthylalanine, 2-naphthylalanine, 2-pyridylalanine, 3-pyridylalanine, 4-pyridylalanine, 2-thienylalanine, 3-thienylalanine, 4-thiazolylalanine, 2-furylalanine, 3-furylalanine, Phe, wherein the phenyl moiety of said Phe is optionally substituted by halogen, hydroxyl, alkoxy, nitro, benzoyl, methyl, trifluoromethyl or cyano;

$X^6$ represents (D)-Phe, wherein the phenyl moiety of said (D)-Phe is optionally substituted with halogen, hydroxy, alkoxy, nitro, methyl, trifluoromethyl or cyano;

$X^7$ represents Arg;

$X^8$ represents Trp or 2-naphthylalanine;

$X^9$ represents a bond or an amino acid, or di-peptide residue, wherein the amino acid(s) may be natural or synthetic;

$X^{10}$ represents a bond or an amino acid residue optionally capable of making a bridge to $X^3$;

$X^{11}$ represents a bond, an amino acid or a di-peptide, wherein the amino acid(s) may be natural or synthetic;

$R^2$ represents —OH or —NRR', wherein R and R' independently represent hydrogen, $C_{1-8}$alkyl, $C_{2-8}$alkenyl or $C_{2-8}$alkynyl;

wherein the peptide of formula I is optionally cyclized from $X^3$ to $X^{10}$ via a lactame or a disulfide bridge;

with the provision that the compound according to formula I comprises one protracting group;

and with the further proviso that compounds of formula I comprises at least 7 amino acid residues;

and any pharmaceutically acceptable salt, solvate or hydrate thereof.

2. The peptide of claim 1, wherein $X^3$ represents Lys, Orn, 2,4-diamino butyric acid, 2,3-diamino propionic acid, Cys, homoCys, Glu, Asp, Gln or Asn;

and wherein $X^{10}$ represents Lys, Orn, 2,4-diamino butyric acid, 2,3-diamino propionic acid, Cys, homoCys, Glu, Asp, Gln or Asp; and wherein the linker S if present represents β-alanine, Glu, Gly-Gln, Gly-Glu, Gly-His, or

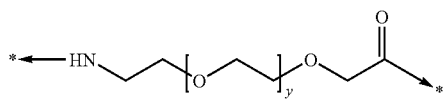

y being 1,2,3,4 or 5.

3. The peptide of claim 2, wherein there is a bond between $X^3$ and $X^{10}$ to make the compound of formula I cyclic by a disulfide bridge ($X^3$, $X^{10}$ are independently Cys or homoCys) or by an lactam bond between an acid in the side chain of $X^3$ or $X^{10}$ and an amine in the side chain of $X^{10}$ or $X^3$.

4. The peptide of claim 3, wherein X is a bond.

5. The peptide of claim 3, wherein $X^1$ represents a bond; $X^2$ represents Nle; or $X^1$ represents a bond and $X^2$ represents Nle.

6. The peptide of claim 4, wherein $X^1$ represents a bond; $X^2$ represents Nle; or $X^1$ represents a bond and $X^2$ represents Nle.

7. The peptide of claim 6, wherein $X^3$ represents Glu or Asp and $X^{10}$ represents Lys, Orn, 2,4-diamino butyric acid or 2,3-diamino propionic acid.

8. The peptide of claim 3, wherein $X^3$ represents Glu or Asp and $X^{10}$ represents Lys, Orn, 2,4-diamino butyric acid or 2,3-diamino propionic acid.

9. The peptide of claim 7, wherein $X^3$ represents Glu or Asp, and $X^{10}$ represents Lys.

10. The peptide of claim 3, wherein $X^4$ represents a bond.

11. The peptide of claim 9, wherein $X^4$ represents a bond.

12. The peptide of claim 3, wherein $X^5$ represents Ala, Nle, Met, Met(O), Met(O$_2$), Gln, Gln(ϵ-alkyl), Gln(ϵ-aryl), Asn, Asn (ϵ-alkyl), Asn(ϵ-aryl), Ser, Thr, Cys, F-Pro, Pro, Hyp, (S)-1,2,3,4-tetrahydroisoquinoline-3-carboxylic acid, Trp, 1-naphthylalanine, 2-naphthylalanine, 2-PyAla, 3-PyAla, 4-PyAla, 2-thienylalanine, 3-thienylalanine, 4-thiazolylalanine, 2-furylalanine, 3-furylalanine, Phe, wherein the phenyl moiety of said Phe is optionally substituted by halogen, hydroxyl, alkoxy, nitro, benzoyl, methyl, trifluoromethyl or cyano.

13. The peptide of claim 11, wherein $X^5$ represents Ala, Nle, Met, Met(O), Met(O$_2$), Gln, Gln(ϵ-alkyl), Gln(ϵ-aryl), Asn, Asn(ϵ-alkyl), Asn(ϵ-aryl), Ser, Thr, Cys, F-Pro, Pro, Hyp, (S)-1,2,3,4-tetrahydroisoquinoline-3-carboxylic acid, Trp, 1-naphthylalanine, 2-naphthylalanine, 2-PyAla, 3-PyAla, 4-PyAla, 2-thienylalanine, 3-thienylalanine, 4-thiazolylalanine, 2-furylalanine, 3-furylalanine, Phe, wherein the phenyl moiety of said Phe is optionally substituted by halogen, hydroxyl, alkoxy, nitro, benzoyl, methyl, trifluoromethyl or cyano.

14. The peptide of claim 3, wherein $X^5$ represents His.

15. The peptide of claim 9, wherein $X^5$ represents His.

16. The peptide of claim 3, wherein $X^5$ represents 3-PyAla, Hyp, Gln or Asn.

17. The peptide of claim 9, wherein $X^5$ represents 3-PyAla, Hyp, Gln or Asn.

18. The peptide of claim 3, wherein $X^9$ represents a bond, $X^{11}$ represents a bond, or $X^9$ and $X^{11}$ represent bonds.

19. The peptide of claim 9, wherein $X^9$ represents a bond, $X^{11}$ represents a bond, or $X^9$ and $X^{11}$ represent bonds.

20. The peptide of claim 3, wherein $R^2$ represents —NH$_2$.

21. The peptide of claim 19, wherein $R^2$ represents —NH$_2$.

22. The peptide of claim 3, wherein $X^6$—$X^7$—$X^8$—$X^9$—$X^{10}$ represents D-Phe-Arg-Trp-Lys.

23. The peptide of claim 3, wherein the peptide is selected from:

$R^4$-Nle-c[Asp-3-PyAla-D-Phe-Arg-Trp-Lys]-$R^2$;

$R^4$-Nle-c[Glu-Hyp-D-Phe-Arg-Trp-Lys]-$R^2$;

$R^4$-Nle-c[Asp-Hyp-D-Phe-Arg-Trp-Lys]-$R^2$;

$R^4$-Nle-c[Glu-Gln-D-Phe-Arg-Trp-Lys]-$R^2$;

$R^4$-Nle-c[Asp-Gln-D-Phe-Arg-Trp-Lys]-$R^2$;

-continued

```
R⁴-Nle-c[Glu-Asn-D-Phe-Arg-Trp-Lys]-R²;

R⁴-Nle-c[Asp-Asn-D-Phe-Arg-Trp-Lys]-R²;

R⁴-Nle-c[Glu-3-PyAla-D-Phe-Arg-2Nal-Lys]-R²;

R⁴-Nle-c[Asp-3-PyAla-D-Phe-Arg-2Nal-Lys]-R²;

R⁴-Nle-c[Glu-Hyp-D-Phe-Arg-2Nal-Lys]-R²;

R⁴-Nle-c[Asp-Hyp-D-Phe-Arg-2Nal-Lys]-R²;

R⁴-Nle-c[Glu-Gln-D-Phe-Arg-2Nal-Lys]-R²;

R⁴-Nle-c[Asp-Gln-D-Phe-Arg-2Nal-Lys]-R²;

R⁴-Nle-c[Glu-Asn-D-Phe-Arg-2Nal-Lys]-R²;
and

R⁴-Nle-c[Asp-Asn-D-Phe-Arg-2Nal-Lys]-R².
```

24. The peptide of claim 3, wherein X—$X^1$—$X^2$—$X^3$—$X^4$—$X^5$—$X^6$—$X^7$—$X^8$—$X^9$—$X^{10}$—$R^2$ represents Nle-c[Glu-3-PyAla-D-Phe-Arg-Trp-Lys]-NH$_2$ or Nle-c[Glu-Hyp-D-Phe-Arg-Trp-Lys]-NH$_2$.

25. The peptide of claim 3, wherein X—$X^1$—$X^2$—$X^3$—$X^4$—$X^5$—$X^6$—$X^7$—$X^8$—$X^9$—$X^{10}$—$R^2$ represents Nle-c[Glu-His-D-Phe-Arg-Trp-Lys]-NH$_2$.

26. The peptide of claim 3, wherein X—$X^1$—$X^2$ is represented by a moiety of the formula $Z^1$-$Z^2$-$Z^3$-$Z^4$-$Z^5$-$Z^6$, wherein $Z^1$ represents Gly;

$Z^2$ represents Ser, (D)-Ser or Thr;

$Z^3$ represents Gln, Asn, (D)-Gln or (D)-Asn;

$Z^4$ represents His, homoArg, Arg, Lys or Orn;

$Z^5$ represents Ser, (D)-Ser or Thr; and $Z^6$ represents Nle.

27. The peptide of claim 26, wherein $X^3$ represents Glu, and $X^{10}$ represents Lys.

28. The peptide of claim 26, wherein $X^4$, $X^9$ and $X^{11}$ represent a bond.

29. The peptide of claim 27, wherein $X^4$, $X^9$ and $X^{11}$ represent a bond.

30. The peptide of claim 26, wherein $X^5$ represents Ala, Nle, Met, Met(O), Met(O2), Gln, Gln(ε-alkyl), Gln(ε-aryl), Asn, Asn(ε-alkyl), Asn(ε-aryl), Ser, Thr, Cys, Pro, F-Pro, Hyp, (S)-1,2,3,4-tetrahydroisoquinoline-3-carboxylic acid, Trp, 1-naphthylalanine, 2-naphthylalanine, 2-PyAla, 3-PyAla, 4-PyAla, 2-thienylalanine, 3-thienylalanine, 4-thiazolylalanine, 2-furylalanine, 3-furylalanine, Phe, wherein the phenyl moiety of said Phe is optionally substituted by halogen, hydroxyl, alkoxy, nitro, benzoyl, methyl, trifluoromethyl or cyano.

31. The peptide of claim 29, wherein $X^5$ represents Ala, Nle, Met, Met(O), Met(O2), Gln, Gln(ε-alkyl), Gln(ε-aryl), Asn, Asn(ε-alkyl), Asn(ε-aryl), Ser, Thr, Cys, Pro, F-Pro, Hyp, (S)-1,2,3,4-tetrahydroisoquinoline-3-carboxylic acid, Trp, 1-naphthylalanine, 2-naphthylalanine, 2-PyAla, 3-PyAla, 4-PyAla, 2-thienylalanine, 3-thienylalanine, 4-thiazolylalanine, 2-furylalanine, 3-furylalanine, Phe, wherein the phenyl moiety of said Phe is optionally substituted by halogen, hydroxyl, alkoxy, nitro, benzoyl, methyl, trifluoromethyl or cyano.

32. The peptide of claim 26, wherein $X^5$ represents F-Pro, Hyp or Gln.

33. The peptide of claim 29, wherein $X^5$ represents F-Pro, Hyp or Gln.

34. The peptide of claim 26, wherein $R^2$ represents —NH$_2$.

35. The peptide of claim 26, wherein $X^6$—$X^7$—$X^8$—$X^9$—$X^{10}$ represents (D)-Phe-Arg-Trp-Lys.

36. The peptide of claim 26, wherein the moiety of the formula $Z^1$-$Z^2$-$Z^3$-$Z^4$-$Z^5$-$Z^6$ is selected from amongst

```
Gly-Ser-Asn-Asn-Thr-Nle;          (SEQ ID NO: 18)
Gly-Ser-Asn-homoArg-Thr-Nle;      (SEQ ID NO: 19)
Gly-Ser-DAsn-His-Thr-Nle;         (SEQ ID NO: 20)
Gly-Ser-DAsn-homoArg-Thr-Nle;     (SEQ ID NO: 21)
Gly-Ser-Gln-Arg-Ser-Nle;          (SEQ ID NO: 22)
Gly-Ser-Gln-His-Ser-Nle;          (SEQ ID NO: 23)
Gly-Ser-Gln-homoArg-Ser-Nle;      (SEQ ID NO: 24)
Gly-Ser-Gln-homoArg-Thr-Nle;      (SEQ ID NO: 25)
Gly-Ser-Gln-Lys-Ser-Nle;          (SEQ ID NO: 26)
Gly-Ser-Gln-Orn-Ser-Nle;          (SEQ ID NO: 27)
Gly-Ser-Ser-His-Thr-Nle           (SEQ ID NO: 28)
and
Gly-Ser-Ser-Tyr-Thr-Nle.          (SEQ ID NO: 29)
```

37. The peptide of claim 26, wherein $X^3$—$X^4$—$X^5$—$X^6$—$X^7$—$X^8$—$X^9$—$X^{10}$—$X^{11}$—$R^2$ is selected from

```
cyclo[Glu-3-PyAla-(D)-Phe-Arg-Trp-Lys]-NH₂;

cyclo[Glu-F-Pro-(D)-Phe-Arg-Trp-Lys]-NH₂;

cyclo[Glu-Gln-(D)-Phe-Arg-Trp-Lys]-NH₂;

cyclo[Glu-Hyp-(D)-Phe-Arg-Trp-Lys]-NH₂;
and cyclo[Glu-Met(O2)-(D)-Phe-Arg-Trp-Lys]-NH₂.
```

38. The peptide of claim 2, wherein the compound of formula I is non-cyclic.

39. The peptide of claim 38, wherein X represents a bond.

40. The peptide of claim 38, wherein X represents an amino acid residue.

41. The peptide of claim 40, wherein X represents Ser.

42. The peptide of claim 39, wherein $X^1$ represents Lys (N$^ε$β-Ala-R$^4$).

43. The peptide of claim 40, wherein $X^1$ represents Lys (N$^ε$β-Ala-R$^4$).

44. The peptide of claim 39, wherein $X^1$ represents a bond.

45. The peptide of claim 42, wherein $X^2$ represents Tyr-Ser-Nle.

46. The peptide of claim 44, wherein $X^2$ represents Ser-Nle.

47. The peptide of claim 45, wherein $X^2$ represents Ser-Tyr-Ser-Nle.

48. The peptide of claim 39, wherein $X^3$ represents Glu.

49. The peptide of claim 47, wherein $X^3$ represents Glu.

50. The peptide of claim 39, wherein $X^4$ represents a bond.

51. The peptide of claim 49, wherein $X^4$ represents a bond.

52. The peptide of claim 39, wherein the peptide is characterized by two or more of the following: X represents a bond or an amino acid residue; $X^1$ represents Lys(N$^ε$β-Ala-R$^4$) or a bond; $X^2$ represents Tyr-Ser-Nle, Ser-Nle, or Ser-Tyr-Ser-Nle; $X^3$ represents Glu; and $X^4$ represents a bond.

53. The peptide of claim 39, wherein $X^5$ represents Ala, Nle, Met, Met(O), Met(O$_2$), Gln, Gln($\epsilon$-alkyl), Gln($\epsilon$-aryl), Asn, Asn($\epsilon$-alkyl), Asn($\epsilon$-aryl), Ser, Thr, Cys, F-Pro, Pro, Hyp, (S)-1,2,3,4-tetrahydroisoquinoline-3-carboxylic acid, Trp, 1-naphthylalanine, 2-naphthylalanine, 2-PyAla, 3-PyAla, 4-PyAla, 2-thienylalanine, 3-thienylalanine, 4-thiazolylalanine, 2-furylalanine, 3-furylalanine, Phe, wherein the phenyl moiety of said Phe is optionally substituted by halogen, hydroxyl, alkoxy, nitro, benzoyl, methyl, trifluoromethyl or cyano.

54. The peptide of claim 39, wherein $X^5$ represents His.

55. The peptide of claim 39, wherein $X^5$ represents Gln, Hyp, 3-PyAla, Ala or Ser.

56. The peptide of claim 39, wherein $X^9$ represents Gly.

57. The peptide of claim 39, wherein $X^{10}$ represents Lys or Arg.

58. The peptide of claim 39, wherein $X^{11}$ represents Pro-Val.

59. The peptide of claim 39, wherein the peptide is characterized by two or more of the following: $X^5$ represents His, Gln, Hyp, 3-PyAla, Ala or Ser; $X^9$ represents Gly; $X^{10}$ represents Lys or Arg; and $X^{11}$ represents Pro-Val.

60. The peptide of claim 52, wherein the peptide is characterized by two or more of the following: $X^5$ represents His, Gln, Hyp, 3-PyAla, Ala or Ser; $X^9$ represents Gly; $X^{10}$ represents Lys or Arg; and $X^{11}$ represents Pro-Val.

61. The peptide of claim 39, wherein $R^2$ represents —NH$_2$.

62. The peptide of claim 59, wherein $R^2$ represents —NH$_2$.

63. The peptide of claim 60, wherein $R^2$ represents —NH$_2$.

64. The peptide of claim 1, wherein $R^1$—X—$X^1$—$X^2$—$X^3$—$X^4$—$X^5$—$X^6$—$X^7$—$X^8$—$X^9$—$X^{10}$—$R^2$ represents a compound selected from amongst CH$_3$C(O)-Lys(N$^\epsilon$β-Ala-R$^4$)-Tyr-Ser-Nle-Glu-Hyp-D-Phe-Arg-Trp-Gly-Lys-Pro-Val-NH$_2$, CH$_3$C(O)-Lys(N$^\epsilon$β-Ala-R$^4$)-Tyr-Ser-Nle-Glu-3-PyAla-D-Phe-Arg-Trp-Gly-Lys-Pro-Val-NH$_2$, CH$_3$C(O)-Lys(N$^\epsilon$β-Ala-R$^4$)-Tyr-Ser-Nle-Glu-Ser-D-Phe-Arg-Trp-Gly-Arg-Pro-Val-NH$_2$, CH$_3$C(O)-Lys(N$^\epsilon$β-Ala-R$^4$)-Tyr-Ser-Nle-Glu-Ala-D-Phe-Arg-Trp-Gly-Arg-Pro-Val-NH$_2$, CH$_3$C(O)-Lys(N$^\epsilon$β-Ala-R$^4$)-Tyr-Ser-Nle-Glu-Gln-D-Phe-Arg-Trp-Gly-Arg-Pro-Val-NH$_2$, CH$_3$C(O)-Lys(N$^\epsilon$β-Ala-R$^4$)-Tyr-Ser-Nle-Glu-Hyp-D-Phe-Arg-Trp-Gly-Arg-Pro-Val-NH$_2$ 65. The peptide of claim 1, wherein $R^1$—X—$X^1$—$X^2$—$X^3$—$X^4$—$X^5$—$X^6$—$X^7$—$X^8$—$X^9$—$X^{10}$—$X^{11}$—$R^2$ represents a compound selected from amongst CH$_3$C(O)-Ser-Lys(N$^\epsilon$β-Ala-R$^4$)-Ser-Nle-Glu-Hyp-D-Phe-Arg-Trp-Gly-Lys-Pro-Val-NH$_2$, CH$_3$C(O)-Ser-Lys(N$^\epsilon$β-Ala-R$^4$)-Ser-Nle-Glu-3-PyAla-D-Phe-Arg-Trp-Gly-Lys-Pro-Val-NH$_2$, CH$_3$C(O)-Ser-Lys(N$^\epsilon$β-Ala-R$^4$)-Ser-Nle-Glu-Ser-D-Phe-Arg-Trp-Gly-Arg-Pro-Val-NH$_2$, CH$_3$C(O)-Ser-Lys(N$^\epsilon$β-Ala-R$^4$)-Ser-Nle-Glu-Ala-D-Phe-Arg-Trp-Gly-Arg-Pro-Val-NH$_2$, CH$_3$C(O)-Ser-Lys(N$^\epsilon$β-Ala-R$^4$)-Ser-Nle-Glu-Gln-D-Phe-Arg-Trp-Gly-Arg-Pro-Val-NH$_2$, CH$_3$C(O)-Ser-Lys(N$^\epsilon$β-Ala-R$^4$)-Ser-Nle-Glu-Hyp-D-Phe-Arg-Trp-Gly-Arg-Pro-Val-NH$_2$, CH$_3$C(O)-Ser-Lys(N$^\epsilon$β-Ala-R$^4$)-Ser-Nle-Glu-3-PyAla-D-Phe-Arg-Trp-Gly-Arg-Pro-Val-NH$_2$.

66. The peptide of claim 2, wherein $R^1$—X—$X^1$—$X^2$—$X^3$—$X^4$—$X^5$—$X^6$—$X^7$—$X^8$—$X^9$—$X^{10}$—$X^{11}$—$R^2$ represents a compound selected from amongst R$^4$-Ser-Tyr-Ser-Nle-Glu-Gln-D-Phe-Arg-Trp-Gly-Lys-Pro-Val-NH$_2$, R$^4$-Ser-Tyr-Ser-Nle-Glu-Hyp-D-Phe-Arg-Trp-Gly-Lys-Pro-Val-NH$_2$, R$^4$-Ser-Tyr-Ser-Nle-Glu-3-PyAla-D-Phe-Arg-Trp-Gly-Lys-Pro-Val-NH$_2$, R$^4$-Ser-Tyr-Ser-Nle-Glu-Ser-D-Phe-Arg-Trp-Gly-Arg-Pro-Val-NH$_2$, R$^4$-Ser-Tyr-Ser-Nle-Glu-Ala-D-Phe-Arg-Trp-Gly-Arg-Pro-Val-NH$_2$, R$^4$-Ser-Tyr-Ser-Nle-Glu-Gln-D-Phe-Arg-Trp-Gly-Arg-Pro-Val-NH$_2$, R$^4$-Ser-Tyr-Ser-Nle-Glu-Hyp-D-Phe-Arg-Trp-Gly-Arg-Pro-Val-NH$_2$, R$^4$-Ser-Tyr-Ser-Nle-Glu-3-PyAla-D-Phe-Arg-Trp-Gly-Arg-Pro-Val-NH$_2$.

67. The peptide of claim 1, wherein $R^4$ represents a straight, branched and/or cyclic $C_{8-20}$alkanoyl, $C_{8-20}$alkenoyl or $C_{8-20}$alkynoyl, all of which may optionally be substituted with one or more substituents selected from hydroxyl, halogen, carboxyl and aryl, wherein said aryl may optionally be further substituted by one or more substituents selected from hydroxyl, halogen, and carboxyl.

68. The peptide of claim 67, wherein $R^4$ represents a straight, branched and/or cyclic $C_{14-16}$alkanoyl, $C_{14-16}$alkenoyl or $C_{14-16}$alkynoyl, all of which may optionally be substituted with one or more substituents selected from hydroxyl, halogen, carboxyl and aryl, wherein said aryl may optionally be further substituted by one or more substituents selected from hydroxyl, halogen, and carboxyl.

69. The peptide of claim 68, wherein $R^4$ represents a straight $C_{10-20}$alkanoyl, $C_{14-16}$alkanoyl or $C_{8-17}$alkanoyl.

70. The peptide of claim 1, wherein $R^4$ represents octanoyl, decanoyl, dodecnoyl, tetradecanoyl, hexadecanoyl, octadecanoyl, 9-carboxy-nonanoyl, 11-carboxy-undecanoyl, 13-carboxy-tridecanoyl, 15-carboxy-pentadecanoyl, 17-carboxy-heptadecanoyl, adamantan-1-yl-acetyl, choloyl, lithocholyl or mPEG2000.

71. The peptide of claim 1, wherein the peptide is selected from amongst

Octanoyl-Nle-c[Glu-His-D-Phe-Arg-Trp-Lys]-NH2 (SEQ ID NO: 56),
Decanoyl-Nle-c[Glu-His-D-Phe-Arg-Trp-Lys]-NH2 (SEQ ID NO: 57),
Tetradecanoyl-Nle-c[Glu-His-D-Phe-Arg-Trp-Lys]-NH2 (SEQ ID NO: 58),
(Adamantan-1-yl)acetyl-Nle-c[Glu-His-D-Phe-Arg-Trp-Lys]-NH2 (SEQ ID NO: 59),
Tetradecanoyl-Nle-c[Glu-3-PyAla-D-Phe-Arg-Trp-Lys]-NH2 (SEQ ID NO: 60),
Decanoyl-Nle-c[Glu-3-PyAla-D-Phe-Arg-Trp-Lys]-NH2 (SEQ ID NO: 61),
(Adamantan-1yl)acetyl-Nle-c[Glu-3-PyAla-D-Phe-Arg-Trp-Lys]-NH2 (SEQ ID NO: 62),
Acetyl-Ser-Lys(3-(dodecanoylamino)propionyl)-Ser-Nle-Glu-Ser-D-Phe-Arg-Trp-Gly-Lys-Pro-Val-NH2 (SEQ ID NO: 63),
Acetyl-Lys(3-(dodecanoylamino)propionyl)-Tyr-Ser-Nle-Glu-Ser-D-Phe-Arg-Trp-Gly-Lys-Pro-Val-NH2 (SEQ ID NO: 64),
Hexadecanoyl-Ser-Tyr-Ser-Nle-Glu-Ser-D-Phe-Arg-Trp-Gly-Lys-Pro-Val-NH2 (SEQ ID NO: 65),
Hexadecanoyl-Ser-Tyr-Ser-Nle-Glu-3-PyAla-D-Phe-Arg-Trp-Gly-Lys-Pro-Val-NH2 (SEQ ID NO: 66),
2-[2-(Hexadecanoylamino)ethoxy]ethoxyacetyl-Ser-Tyr-Ser-Nle-Glu-3-PyAla-D-Phe-Arg-Trp- Gly-Lys-Pro-Val-NH2 (SEQ ID NO: 67),
Hexadecanoyl-βAla-Tyr-Ser-Nle-c[Glu-Hyp-D-Phe-Arg-Trp-Lys]-NH2 (SEQ ID NO: 68),
Hexadecanoyl-βAla-Ala-Tyr-Ser-Nle-c[Glu-Hyp-D-Phe-Arg-Trp-Lys]-NH2 (SEQ ID NO: 69),
Acetyl-Ser-Lys(3-(dodecanoylamino)propionyl)-Ser-Nle-Glu-Hyp-D-Phe-Arg-Trp-Gly-Lys-Pro-Val-NH2 (SEQ ID NO: 70),
mPEG(2000)acetyl-Nle-c[Glu-Hyp-D-Phe-Arg-Trp-Lys]-NH2 (SEQ ID NO: 71),
2-[2-(Lithocholoylamino)ethoxy]ethoxyacetyl-βAla-Tyr-Ser-Nle-c[Glu-Hyp-D-Phe-Arg-Trp-Lys]-NH2 (SEQ ID NO: 72),
2-[2-( 15-Carboxypentadecanoylamino)ethoxy]ethoxy-acetyl-βAla-Ala-Tyr-Ser-Nle-c[Glu-Hyp-D-Phe-Arg-Trp-Lys]-NH2 (SEQ ID NO: 73),
Acetyl-Ser-Lys(3-(dodecanoylamino)propionyl)-Ser-Phe-Glu-Hyp-D-Phe-Arg-Trp-Gly-Lys-Pro-Val-NH2 (SEQ ID NO: 74),
2-[2-(15-Carboxypentadecanoylamino)ethoxy]ethoxy-acetyl-Ser-Gln-Ser-Nle-c[Glu-Hyp-D-Phe-Arg-Trp-Lys]-NH2 (SEQ ID NO: 75),
Hexadecanoyl-Gly-Ser-Gln-His-Ser-Nle-c[Glu-Hyp-D-Phe-Arg-Trp-Lys]-NH2 (SEQ ID NO: 76),
15-Carboxypentadecanoyl-Gly-Ser-Gln-His-Ser-Nle-c[Glu-Hyp-D-Phe-Arg-Trp-Lys]-NH2 (SEQ ID NO: 77),
4-(Hexadecanoylsulfamoyl)butanoyl-Gly-Ser-Gln-His-Ser-Nle-c[Glu-Hyp-D-Phe-Arg-Trp-Lys]-NH2 (SEQ ID NO: 78),
4-[2-(4-Benzoylphenyl)propionylsulfamoyl]butanoyl-Gly-Ser-Gln-His-Ser-Nle-c[Glu-Hyp-D-Phe-Arg-Trp-Lys]-NH2 (SEQ ID NO: 79),
2-[2-(Octadecanoylamino)ethoxy]ethoxyacetyl-Gly-Ser-Gln-His-Ser-Nle-c[Glu-Hyp-D-Phe-Arg-Trp-Lys]-NH2 (SEQ ID NO: 80),
2-[2-(Octadecanoylamino)ethoxy]ethoxyacetyl-Nle-c[Glu-Hyp-D-Phe-Arg-Trp-Lys]-NH2 (SEQ ID NO: 81),
Hexadecanoyl-Gly-Ser-Gln-homoArg-Ser-Nle-c[Glu-Hyp-D-Phe-Arg-Trp-Lys]-NH2 (SEQ ID NO: 82),
2-[2-(15-Carboxypentadecanoylamino)ethoxy]ethoxy-acetyl-Nle-c[Glu-Hyp-D-Phe-Arg-Trp-Lys]-NH2 (SEQ ID NO: 83),
Hexadecanoyl-Gly-Ser-Gln-His-Ser-Nle-c[Glu-Met(O2)-D-Phe-Arg-Trp-Lys]-NH2 (SEQ ID NO: 84),
4-(Hexadecanoylsulfamoyl)butanoyl-Gly-Ser-Gln-Arg-Ser-Nle-c[Glu-Met(O2)-D-Phe-Arg-Trp-Lys]-NH2 (SEQ ID NO: 85),
Hexadecanoyl-Gly-Ser-Gln-homoArg-Ser-Nle-c[Glu-3-PyAla-D-Phe-Arg-Trp-Lys]-NH2 (SEQ ID NO: 86),
Hexadecanoyl-Gly-Ser-Gln-Arg-Ser-Nle-c[Glu-Met(O2)-D-Phe-Arg-Trp-Lys]-NH2 (SEQ ID NO: 87),
4-(Hexadecanoylsulfamoyl)butanoyl-Gly-Ser-Gln-Arg-Ser-Nle-c[Glu-Gln-D-Phe-Arg-Trp-Lys]-NH2 (SEQ ID NO: 88),
3-(2-{2-[2-(2-(Hexadecanoylamino)ethoxy)ethoxy]ethoxy}ethoxy)propionyl-Nle-c[Glu-Hyp-D-Phe-Arg-Trp-Lys]-NH2 (SEQ ID NO: 89),
2-[2-(Hexadecanoylamino)ethoxy]ethoxyacetyl-Gly-Ser-Gln-His-Ser-Nle-c[Glu-Hyp-D-Phe-Arg-Trp-Lys]-NH2 (SEQ ID NO: 90),
2-[2-(Tetradecanoylamino)ethoxy]ethoxyacetyl-Gly-Ser-Gln-His-Ser-Nle-c[Glu-Hyp-D-Phe-Arg-Trp-Lys]-NH2 (SEQ ID NO: 91),
Hexadecanoyl-Gly-Thr-Gln-His-Ser-Nle-c[Glu-Hyp-D-Phe-Arg-Trp-Lys]-NH2 (SEQ ID NO: 92),
Hexadecanoyl-Gly-Gln-Gln-His-Ser-Nle-c[Glu-Hyp-D-Phe-Arg-Trp-Lys]-NH2 (SEQ ID NO: 93),
Hexadecanoyl-Gly-Thr-Gln-His-Ser-Nle-c[Glu-Asn-D-Phe-Arg-Trp-Lys]-NH2 (SEQ ID NO: 94),
Hexadecanoyl-Glu-Thr-Gln-His-Ser-Nle-c[Glu-Hyp-D-Phe-Arg-Trp-Lys]-NH2 (SEQ ID NO: 95),
Hexadecanoyl-Glu-Gly-Thr-Gln-His-Ser-Nle-c[Glu-Hyp-D-Phe-Arg-Trp-Lys]-NH2 (SEQ ID NO: 96),
Hexadecanoyl-Glu-4-Abu-Thr-Gln-His-Ser-Nle-c[Glu-Hyp-D-Phe-Arg-Trp-Lys]-NH2 (SEQ ID NO: 97),
2-[2-(Hexadecanoylamino)ethoxy]ethoxyacetyl-His-Ser-Nle-c[Glu-Hyp-D-Phe-Arg-Trp-Lys]-NH2 (SEQ ID NO: 98),
2-[2-(Hexadecanoylamino)ethoxy]ethoxyacetyl-Arg-Ser-Nle-c[Glu-Hyp-D-Phe-Arg-Trp-Lys]-NH2 (SEQ ID NO: 99), 2-[2-(Hexadecanoylamino)ethoxy]ethoxyacetyl-Gln-Ser-Nle-c[Glu-Hyp-D-Phe-Arg-Trp-Lys]-NH2 (SEQ ID NO: 100), 2-[2-(Hexadecanoylamino)ethoxy]ethoxyacetyl-Glu-Ser-Nle-c[Glu-Hyp-D-Phe-Arg-Trp-Lys]-NH2 (SEQ ID NO: 101), 2-[2-(2-{2-[2-(Dodecanoylamino)ethoxy]ethoxy}acetylamino)ethoxy]ethoxyacetyl-Nle-c[Glu-Hyp-D-Phe-Arg-Trp-Lys]-NH2 (SEQ ID NO: 102), 2-{2-[4-Carbamoyl-2-(2-(hexadecanoylamino)acetylamino)butyrylamino]ethoxy}ethoxyacetyl-Nle-c[Glu-Hyp-D-Phe-Arg-Trp-Lys]-NH2 (SEQ ID NO: 103), 2-{2-[4-Carboxy-2-(2-hexadecanoylamino)acetylamino)butyrylamino]ethoxy}ethoxyacetyl-Nle-c[Glu-Hyp-D-Phe-Arg-Trp-Lys]-NH2 (SEQ ID NO: 104), 2-{2-[2-(2-(Hexadecanoylamino)acetylamino)-3-(imidazol-4-yl)propionylamino]ethoxy}ethoxyacteyl-Nle-c[Glu-Hyp-D-Phe-Arg-Trp-Lys]-NH2 (SEQ ID NO: 105), Dodecanoyl-Nle-c[Glu-Hyp-D-Phe-Arg-Trp-Lys]-NH2 (SEQ ID NO: 106), Hexadecanoyl-Gly-Thr-Asn-Asn-Thr-Nle-c[Glu-Hyp-D-Phe-Arg-Trp-Lys]-NH2 (SEQ ID NO: 107), Octanoyl-Gly-Ser-D-Gln-His-Thr-Nle-c[Glu-Hyp-D-Phe-Arg-Trp-Lys]-NH2 (SEQ ID NO: 108), Decanoyl-Gly-Ser-D-Gln-His-Thr-Nle-c[Glu-Hyp-D-Phe-Arg-Trp-Lys]-NH2 (SEQ ID NO: 109), Dodecanoyl-Gly-Ser-D-Gln-His-Thr-Nle-c[Glu-Hyp-D-Phe-Arg-Trp-Lys]-NH2 (SEQ ID NO: 110), Tetradecanoyl-Gly-Ser-D-Gln-His-Thr-Nle-c[Glu-Hyp-D-Phe-Arg-Trp-Lys]-NH2 (SEQ ID NO: 111), Hexadecanoyl-Gly-Ser-D-Gln-His-Thr-Nle-c[Glu-Hyp-D-Phe-Arg-Trp-Lys]-NH2 (SEQ ID NO: 112), Octadecanoyl-Gly-Ser-D-Gln-His-Thr-Nle-c[Glu-Hyp-D-Phe-Arg-Trp-Lys]-NH2 (SEQ ID NO: 113), Hexadecanoyl-Gly-Ser-Gln-His-Ser-Nle-c[Glu-F-Pro-D-Phe-Arg-Trp-Lys]-NH2 (SEQ ID NO: 114), Hexadecanoyl-Gly-Ser-Gln-homoArg-Ser-Nle-c[Glu-F-Pro-D-Phe-Arg-Trp-Lys]-NH2 (SEQ ID NO: 115), Hexadecanoyl-Gly-Ser-Gln-homoArg-Thr-Nle-c[Glu-F-Pro-D-Phe-Arg-Trp-Lys]-NH2 (SEQ ID NO: 116), Hexadecanoyl-Gly-Ser-Asn-homoArg-Thr-Ser-Nle-c[Glu-F-Pro-D-Phe-Arg-Trp-Lys]-NH2 (SEQ ID NO: 117), 3-{2-[2-(2-{2-[4-(4,4,5,5,6,6,7,7,8,8,9,9,9-Tridecafluorononanoylsulfamoyl)butyrylamino]-ethoxy}ethoxy)ethoxy]ethoxy}propionyl-Gly-Ser-Gln-homoArg-Nle-c[Glu-Hyp-D-Phe-Arg-Trp-Lys]-NH2 (SEQ ID NO: 118), Hexadecanoyl-Gly-Ser-Ser-Tyr-Thr-Nle-c[Glu-Hyp-D-Phe-Arg-Trp-Lys]-NH2 (SEQ ID NO: 119), Hexadecanoyl-Gly-Ser-Asn-Asn-Thr-Nle-c[Glu-Hyp-D-Phe-Arg-Trp-Lys]-NH2 (SEQ ID NO: 120), Hexadecanoyl-Gly-Ser-Ser-homoArg-Thr-Nle-c[Glu-Hyp-D-Phe-Arg-Trp-Lys]-NH2 (SEQ ID NO: 121), Hexadecanoyl-Gly-Ser-Ser-His-Thr-Nle-c[Glu-Hyp-D-Phe-Arg-Trp-Lys]-NH2 (SEQ ID NO: 122), Hexadecanoyl-Gly-Ser-D-Asn-His-Thr-Nle-c[Glu-Hyp-D-Phe-Arg-Trp-Lys]-NH2 (SEQ ID NO: 123), Hexadecanoyl-Gly-Ser-Asn-homoArg-Thr-Nle-c[Glu-Hyp-D-Phe-Arg-Trp-Lys]-NH2 (SEQ ID NO: 124), Hexadecanoyl-Ser-homoArg-Ser-Nle-c[Glu-Met(O2)-D-Phe-Arg-Trp-Lys]-NH2 (SEQ ID NO: 125), Hexadecanoyl-Gln-homoArg-Thr-Nle-c[Glu-Met(O2)-D-Phe-Arg-Trp-Lys]-NH2 (SEQ ID NO: 126), Hexadecanoyl-Ser-homoArg-Thr-Nle-c[Glu-Met(O2)-D-Phe-Arg-Trp-Lys]-NH2 (SEQ ID NO: 127), Hexadecanoyl-Ser-His-Thr-Nle-c[Glu-Met(O2)-D-Phe-Arg-Trp-Lys]-NH2 (SEQ ID NO: 128), and Hexadecanoyl-Ser-homoArg-Thr-Nle-c[Glu-Met(O2)-D-Phe-Arg-Trp-Lys]-NH2 (SEQ ID NO: 129).

72. The peptide of claim 3, wherein there is a bond between $X^3$ and $X^{10}$, and wherein $X^3$ is 2,4-diaminobutyric acid.

* * * * *

SEQUENCE LISTING

```
<160> NUMBER OF SEQ ID NOS: 129

<210> SEQ ID NO 1
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
```

```
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 3PyAla
<220> FEATURE:
<221> NAME/KEY: MOD_RES
<222> LOCATION: (4)..(4)
<223> OTHER INFORMATION: D form

<400> SEQUENCE: 1

Xaa Asp Ala Phe Arg Trp Lys
1               5

<210> SEQ ID NO 2
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form

<400> SEQUENCE: 2

Xaa Glu Pro Phe Arg Trp Lys
1               5

<210> SEQ ID NO 3
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form

<400> SEQUENCE: 3

Xaa Asp Pro Phe Arg Trp Lys
1               5

<210> SEQ ID NO 4
<211> LENGTH: 7
<212> TYPE: PRT
<213> ORGANISM: Artificial
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form

<400> SEQUENCE: 4

Xaa Glu Gln Phe Arg Trp Lys
1               5

<210> SEQ ID NO 5
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form

<400> SEQUENCE: 5

Xaa Asp Gln Phe Arg Trp Lys
1               5

<210> SEQ ID NO 6
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form

<400> SEQUENCE: 6

Xaa Glu Asn Phe Arg Trp Lys
1               5

<210> SEQ ID NO 7
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: lactam bridge
<220> FEATURE:
<221> NAME/KEY: MOD_RES
<222> LOCATION: (4)..(4)
<223> OTHER INFORMATION: D form

<400> SEQUENCE: 7

Xaa Asp Asn Phe Arg Trp Lys
1               5

<210> SEQ ID NO 8
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 3PyAla
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (6)..(6)
<223> OTHER INFORMATION: 2Nal

<400> SEQUENCE: 8

Xaa Glu Ala Phe Arg Ala Lys
1               5

<210> SEQ ID NO 9
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 3PyAla
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (6)..(6)
<223> OTHER INFORMATION: 2Nal

<400> SEQUENCE: 9
```

```
Xaa Asp Ala Phe Arg Ala Lys
1               5

<210> SEQ ID NO 10
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (6)..(6)
<223> OTHER INFORMATION: 2Nal

<400> SEQUENCE: 10

Xaa Glu Pro Phe Arg Ala Lys
1               5

<210> SEQ ID NO 11
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (6)..(6)
<223> OTHER INFORMATION: 2Nal

<400> SEQUENCE: 11

Xaa Asp Pro Phe Arg Ala Lys
1               5

<210> SEQ ID NO 12
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (6)..(6)
<223> OTHER INFORMATION: 2Nal

<400> SEQUENCE: 12

Xaa Glu Gln Phe Arg Ala Lys
1               5

<210> SEQ ID NO 13
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (6)..(6)
<223> OTHER INFORMATION: 2Nal

<400> SEQUENCE: 13

Xaa Asp Gln Phe Arg Ala Lys
1               5

<210> SEQ ID NO 14
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (6)..(6)
<223> OTHER INFORMATION: 2Nal

<400> SEQUENCE: 14

Xaa Glu Asn Phe Arg Ala Lys
1               5

<210> SEQ ID NO 15
```

```
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (6)..(6)
<223> OTHER INFORMATION: 2Nal

<400> SEQUENCE: 15

Xaa Asp Asn Phe Arg Ala Lys
1               5

<210> SEQ ID NO 16
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 3-PyAla
<220> FEATURE:
<221> NAME/KEY: MOD_RES
<222> LOCATION: (4)..(4)
<223> OTHER INFORMATION: D form

<400> SEQUENCE: 16

Xaa Glu Ala Phe Arg Trp Lys
1               5

<210> SEQ ID NO 17
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form

<400> SEQUENCE: 17

Xaa Glu His Phe Arg Trp Lys
```

```
<210> SEQ ID NO 18
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Nle

<400> SEQUENCE: 18

Gly Ser Asn Asn Thr Xaa
    1               5

<210> SEQ ID NO 19
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Homo Arg
<220> FEATURE:
<221> NAME/KEY: MISC_FEATURE
<222> LOCATION: (6)..(6)
<223> OTHER INFORMATION: Nle

<400> SEQUENCE: 19

Gly Ser Asn Arg Thr Xaa
1               5

<210> SEQ ID NO 20
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: D form
<220> FEATURE:
<221> NAME/KEY: MISC_FEATURE
<222> LOCATION: (6)..(6)
<223> OTHER INFORMATION: Nle

<400> SEQUENCE: 20

Gly Ser Asn His Thr Xaa
1               5

<210> SEQ ID NO 21
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: D form
<220> FEATURE:
<221> NAME/KEY: MOD_RES
<222> LOCATION: (4)..(4)
<223> OTHER INFORMATION: Homo Arg
<220> FEATURE:
<221> NAME/KEY: MISC_FEATURE
<222> LOCATION: (6)..(6)
```

```
<223> OTHER INFORMATION: Nle

<400> SEQUENCE: 21

Gly Ser Asn Arg Thr Xaa
1               5

<210> SEQ ID NO 22
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Nle

<400> SEQUENCE: 22

Gly Ser Gln Arg Ser Xaa
1               5

<210> SEQ ID NO 23
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Nle

<400> SEQUENCE: 23

Gly Ser Gln His Ser Xaa
1               5

<210> SEQ ID NO 24
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Homo Arg
<220> FEATURE:
<221> NAME/KEY: MISC_FEATURE
<222> LOCATION: (6)..(6)
<223> OTHER INFORMATION: Nle

<400> SEQUENCE: 24

Gly Ser Gln Arg Ser Xaa
1               5

<210> SEQ ID NO 25
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Homo Arg
<220> FEATURE:
<221> NAME/KEY: MISC_FEATURE
<222> LOCATION: (6)..(6)
<223> OTHER INFORMATION: Nle

<400> SEQUENCE: 25
```

```
Gly Ser Gln Arg Thr Xaa
1               5

<210> SEQ ID NO 26
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Nle

<400> SEQUENCE: 26

Gly Ser Gln Lys Ser Xaa
1               5

<210> SEQ ID NO 27
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Orn
<220> FEATURE:
<221> NAME/KEY: MISC_FEATURE
<222> LOCATION: (6)..(6)
<223> OTHER INFORMATION: Nle

<400> SEQUENCE: 27

Gly Ser Gln Xaa Ser Xaa
1               5

<210> SEQ ID NO 28
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Nle

<400> SEQUENCE: 28

Gly Ser Ser His Thr Xaa
1               5

<210> SEQ ID NO 29
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Nle

<400> SEQUENCE: 29

Gly Ser Ser Tyr Thr Xaa
1               5

<210> SEQ ID NO 30
<211> LENGTH: 6
```

```
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (2)..(2)
<223> OTHER INFORMATION: 3-PyAla
<220> FEATURE:
<221> NAME/KEY: MOD_RES
<222> LOCATION: (3)..(3)
<223> OTHER INFORMATION: D form
<220> FEATURE:
<221> NAME/KEY: MOD_RES
<222> LOCATION: (6)..(6)
<223> OTHER INFORMATION: AMIDATION

<400> SEQUENCE: 30

Glu Ala Phe Arg Trp Lys
1               5

<210> SEQ ID NO 31
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (2)..(2)
<223> OTHER INFORMATION: 4-fluoro proline
<220> FEATURE:
<221> NAME/KEY: MOD_RES
<222> LOCATION: (3)..(3)
<223> OTHER INFORMATION: D form
<220> FEATURE:
<221> NAME/KEY: MOD_RES
<222> LOCATION: (6)..(6)
<223> OTHER INFORMATION: AMIDATION

<400> SEQUENCE: 31

Glu Pro Phe Arg Trp Lys
1               5

<210> SEQ ID NO 32
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: D form
<220> FEATURE:
<221> NAME/KEY: MOD_RES
<222> LOCATION: (6)..(6)
<223> OTHER INFORMATION: AMIDATION

<400> SEQUENCE: 32

Glu Gln Phe Arg Trp Lys
1               5
```

```
<210> SEQ ID NO 33
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (3)..(3)
<223> OTHER INFORMATION: D form
<220> FEATURE:
<221> NAME/KEY: MOD_RES
<222> LOCATION: (6)..(6)
<223> OTHER INFORMATION: AMIDATION

<400> SEQUENCE: 33

Glu Pro Phe Arg Trp Lys
1               5

<210> SEQ ID NO 34
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (2)..(2)
<223> OTHER INFORMATION: Met(O2)
<220> FEATURE:
<221> NAME/KEY: MOD_RES
<222> LOCATION: (3)..(3)
<223> OTHER INFORMATION: D form
<220> FEATURE:
<221> NAME/KEY: MOD_RES
<222> LOCATION: (6)..(6)
<223> OTHER INFORMATION: AMIDATION

<400> SEQUENCE: 34

Glu Met Phe Arg Trp Lys
1               5

<210> SEQ ID NO 35
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: N(epsilon) beta-alanine R4
<220> FEATURE:
<221> NAME/KEY: MISC_FEATURE
<222> LOCATION: (4)..(4)
<223> OTHER INFORMATION: Nle
<220> FEATURE:
```

```
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 35

Lys Tyr Ser Xaa Glu Pro Phe Arg Trp Gly Lys Pro Val
1               5                   10

<210> SEQ ID NO 36
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: N(epsilon) beta-Ala R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 3-PyAla
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 36

Lys Tyr Ser Xaa Glu Ala Phe Arg Trp Gly Lys Pro Val
1               5                   10

<210> SEQ ID NO 37
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: N(epsilon) beta-alanine R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
```

```
<222> LOCATION: (13)..(13)
<223> OTHER INFORMATION: AMIDATION

<400> SEQUENCE: 37

Lys Tyr Ser Xaa Glu Ser Phe Arg Trp Gly Arg Pro Val
1               5                   10

<210> SEQ ID NO 38
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: N(epsilon) beta-Ala R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 38

Lys Tyr Ser Xaa Glu Ala Phe Arg Trp Gly Arg Pro Val
1               5                   10

<210> SEQ ID NO 39
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: N(epsilon) beta-Ala R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 39

Lys Tyr Ser Xaa Glu Gln Phe Arg Trp Gly Arg Pro Val
1               5                   10

<210> SEQ ID NO 40
<211> LENGTH: 13
<212> TYPE: PRT
<213> ORGANISM: Artificial
```

```
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: N(epsion) beta-Ala R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 40

Lys Tyr Ser Xaa Glu Pro Phe Arg Trp Gly Arg Pro Val
1               5                   10

<210> SEQ ID NO 41
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N(epsilon) beta-Ala R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 41

Ser Lys Ser Xaa Glu Pro Phe Arg Trp Gly Lys Pro Val
1               5                   10

<210> SEQ ID NO 42
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (2)..(2)
<223> OTHER INFORMATION: N(epsilon) beta-Ala R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 3-PyAla
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 42

Ser Lys Ser Xaa Glu Ala Phe Arg Trp Gly Lys Pro Val
1               5                   10

<210> SEQ ID NO 43
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N(epsilon) beta-Ala R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 43

Ser Lys Ser Xaa Glu Ser Phe Arg Trp Gly Arg Pro Val
1               5                   10

<210> SEQ ID NO 44
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N(epsilon) beta-Ala R4
<220> FEATURE:
<221> NAME/KEY: MISC_FEATURE
<222> LOCATION: (4)..(4)
<223> OTHER INFORMATION: Nle
```

```
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 44

Ser Lys Ser Xaa Glu Ala Phe Arg Trp Gly Arg Pro Val
1               5                   10

<210> SEQ ID NO 45
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N(epsilon) beta-Ala R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 45

Ser Lys Ser Xaa Glu Gln Phe Arg Trp Gly Arg Pro Val
1               5                   10

<210> SEQ ID NO 46
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N(epsilon) beta-Ala R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION
```

```
<400> SEQUENCE: 46

Ser Lys Ser Xaa Glu Pro Phe Arg Trp Gly Arg Pro Val
1               5                   10

<210> SEQ ID NO 47
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N(epsilon) beta-Ala R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 3-PyAla
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 47

Ser Lys Ser Xaa Glu Ala Phe Arg Trp Gly Arg Pro Val
1               5                   10

<210> SEQ ID NO 48
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Bonded to R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 48

Ser Tyr Ser Xaa Glu Gln Phe Arg Trp Gly Lys Pro Val
1               5                   10

<210> SEQ ID NO 49
<211> LENGTH: 13
<212> TYPE: PRT
<213> ORGANISM: Artificial
<220> FEATURE:
<223> OTHER INFORMATION: Synthetic
<220> FEATURE:
```

```
<221> NAME/KEY: MOD_RES
<222> LOCATION: (1)..(1)
<223> OTHER INFORMATION: Bonded to R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 49

Ser Tyr Ser Xaa Glu Pro Phe Arg Trp Gly Lys Pro Val
1               5                   10

<210> SEQ ID NO 50
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Bonded to R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 3-PyAla
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 50

Ser Tyr Ser Xaa Glu Ala Phe Arg Trp Gly Lys Pro Val
1               5                   10

<210> SEQ ID NO 51
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Bonded to R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
```

```
<222> LOCATION: (13)..(13)
<223> OTHER INFORMATION: AMIDATION

<400> SEQUENCE: 51

Ser Tyr Ser Xaa Glu Ser Phe Arg Trp Gly Arg Pro Val
1               5                   10

<210> SEQ ID NO 52
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Bonded to R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 52

Ser Tyr Ser Xaa Glu Ala Phe Arg Trp Gly Arg Pro Val
1               5                   10

<210> SEQ ID NO 53
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Bonded to R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 53

Ser Tyr Ser Xaa Glu Gln Phe Arg Trp Gly Arg Pro Val
1               5                   10

<210> SEQ ID NO 54
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Bonded to R4
<220> FEATURE:
<221> NAME/KEY: MISC_FEATURE
```

```
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 54

Ser Tyr Ser Xaa Glu Pro Phe Arg Trp Gly Arg Pro Val
1               5                   10

<210> SEQ ID NO 55
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Bonded to R4
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 3-PyAla
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 55

Ser Tyr Ser Xaa Glu Ala Phe Arg Trp Gly Arg Pro Val
1               5                   10

<210> SEQ ID NO 56
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Octanoyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 56
```

```
Xaa Glu His Phe Arg Trp Lys
1               5

<210> SEQ ID NO 57
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Decanoyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 57

Xaa Glu His Phe Arg Trp Lys
1               5

<210> SEQ ID NO 58
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Tetradecanoyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 58

Xaa Glu His Phe Arg Trp Lys
1               5

<210> SEQ ID NO 59
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Adamantan-1-yl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (4)..(4)
```

```
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 59

Xaa Glu His Phe Arg Trp Lys
1               5

<210> SEQ ID NO 60
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Tetradecanoyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 3PyAla
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 60

Xaa Glu Ala Phe Arg Trp Lys
1               5

<210> SEQ ID NO 61
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: decanoyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 3-PyAla
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 61

Xaa Glu Ala Phe Arg Trp Lys
1               5

<210> SEQ ID NO 62
```

```
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Adamantan-1-yl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 3-PyAla
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 62

Xaa Glu Ala Phe Arg Trp Lys
1               5

<210> SEQ ID NO 63
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Lys(3-(dodecanoylamino)propionyl)
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 63

Ser Lys Ser Xaa Glu Ser Phe Arg Trp Gly Lys Pro Val
1               5                   10

<210> SEQ ID NO 64
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Lys(3-(dodecanoylamino)propionyl)
```

```
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 64

Lys Tyr Ser Xaa Glu Ser Phe Arg Trp Gly Lys Pro Val
1               5                   10

<210> SEQ ID NO 65
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Ser
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 65

Ser Tyr Ser Xaa Glu Ser Phe Arg Trp Gly Lys Pro Val
1               5                   10

<210> SEQ ID NO 66
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Ser
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 3-PyAla
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 66

Ser Tyr Ser Xaa Glu Ala Phe Arg Trp Gly Lys Pro Val
1               5                   10
```

```
<210> SEQ ID NO 67
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 2-[2-(Hexadecanoylamino)ethoxy]ethoxyacetyl-Ser
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 3-PyAla
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 67

Ser Tyr Ser Xaa Glu Ala Phe Arg Trp Gly Lys Pro Val
1               5                   10

<210> SEQ ID NO 68
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Hexadecanoyl-bAla
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Lactam bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 68

Xaa Tyr Ser Xaa Glu Pro Phe Arg Trp Lys
1               5                   10

<210> SEQ ID NO 69
<211> LENGTH: 11
<212> TYPE: PRT
<213> ORGANISM: Artificial
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Hexadecanoyl-bAla
<220> FEATURE:
<221> NAME/KEY: MISC_FEATURE
<222> LOCATION: (5)..(5)
<223> OTHER INFORMATION: Nle
<220> FEATURE:
<221> NAME/KEY: MOD_RES
<222> LOCATION: (6)..(11)
<223> OTHER INFORMATION: Lactam bridge
<220> FEATURE:
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (8)..(8)
<223> OTHER INFORMATION: D form
<220> FEATURE:
<221> NAME/KEY: MOD_RES
<222> LOCATION: (11)..(11)
<223> OTHER INFORMATION: AMIDATION

<400> SEQUENCE: 69

Xaa Ala Tyr Ser Xaa Glu Pro Phe Arg Trp Lys
1               5                   10

<210> SEQ ID NO 70
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Lys(3-(dodecanoylamino)propionyl)
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 70

Ser Lys Ser Xaa Glu Pro Phe Arg Trp Gly Lys Pro Val
1               5                   10

<210> SEQ ID NO 71
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: mPEG(2000)acetyl-Nle
<220> FEATURE:
<221> NAME/KEY: MOD_RES
```

```
<222> LOCATION: (2)..(7)
<223> OTHER INFORMATION: Lactam bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 71

Xaa Glu Pro Phe Arg Trp Lys
1               5

<210> SEQ ID NO 72
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 2-[2-(Lithocholoylamino)ethoxy]ethoxyacetyl-?Ala
<220> FEATURE:
<221> NAME/KEY: MISC_FEATURE
<222> LOCATION: (1)..(1)
<223> OTHER INFORMATION: 2-[2-(Lithocholoylamino)ethoxy]ethoxyacetyl-
      bAla
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: lactam bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 72

Xaa Tyr Ser Xaa Glu Pro Phe Arg Trp Lys
1               5                   10

<210> SEQ ID NO 73
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION:
      2-[2-(15-Carboxypentadecanoylamino)ethoxy]ethoxyacetyl-bAla
<220> FEATURE:
<221> NAME/KEY: MISC_FEATURE
<222> LOCATION: (5)..(5)
<223> OTHER INFORMATION: Nle
<220> FEATURE:
<221> NAME/KEY: MOD_RES
<222> LOCATION: (6)..(11)
<223> OTHER INFORMATION: Lactam bridge
<220> FEATURE:
```

```
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (8)..(8)
<223> OTHER INFORMATION: D form
<220> FEATURE:
<221> NAME/KEY: MOD_RES
<222> LOCATION: (11)..(11)
<223> OTHER INFORMATION: AMIDATION

<400> SEQUENCE: 73

Xaa Ala Tyr Ser Xaa Glu Pro Phe Arg Trp Lys
1               5                   10

<210> SEQ ID NO 74
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Lys(3-(dodecanoylamino)propionyl)
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 74

Ser Lys Ser Phe Glu Pro Phe Arg Trp Gly Lys Pro Val
1               5                   10

<210> SEQ ID NO 75
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION:
      2-[2-(15-Carboxypentadecanoylamino)ethoxy]ethoxyacetyl-Ser
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Lactam bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
```

```
<221> NAME/KEY: MOD_RES
<222> LOCATION: (10)..(10)
<223> OTHER INFORMATION: AMIDATION

<400> SEQUENCE: 75

Ser Gln Ser Xaa Glu Pro Phe Arg Trp Lys
1               5                   10

<210> SEQ ID NO 76
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 76

Gly Ser Gln His Ser Xaa Glu Pro Phe Arg Trp Lys
1               5                   10

<210> SEQ ID NO 77
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 15-carboxypentadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 77
```

```
Gly Ser Gln His Ser Xaa Glu Pro Phe Arg Trp Lys
1               5                   10
```

<210> SEQ ID NO 78
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 4-(Hexadecanoylsulfamoyl)butanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 78

```
Gly Ser Gln His Ser Xaa Glu Pro Phe Arg Trp Lys
1               5                   10
```

<210> SEQ ID NO 79
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: -[2-(4-Benzoylphenyl)
      propionylsulfamoyl]butanoyl-Gly
<220> FEATURE:
<221> NAME/KEY: MOD_RES
<222> LOCATION: (1)..(1)
<223> OTHER INFORMATION: 4-[2-(4-Benzoylphenyl)
      propionylsulfamoyl]butanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

```
<400> SEQUENCE: 79

Gly Ser Gln His Ser Xaa Glu Pro Phe Arg Trp Lys
1               5                   10

<210> SEQ ID NO 80
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 2-[2-(Octadecanoylamino)ethoxy]ethoxyacetyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 80

Gly Ser Gln His Ser Xaa Glu Pro Phe Arg Trp Lys
1               5                   10

<210> SEQ ID NO 81
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 2-[2-(Octadecanoylamino)ethoxy]ethoxyacetyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 81

Xaa Glu Pro Phe Arg Trp Lys
1               5

<210> SEQ ID NO 82
<211> LENGTH: 12
<212> TYPE: PRT
```

```
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MOD_RES
<222> LOCATION: (4)..(4)
<223> OTHER INFORMATION: HomoArg
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 82

Gly Ser Gln Arg Ser Xaa Glu Pro Phe Arg Trp Lys
1               5                   10

<210> SEQ ID NO 83
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION:
     2-[2-(15-Carboxypentadecanoylamino)ethoxy]ethoxyacetyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 83

Xaa Glu Pro Phe Arg Trp Lys
1               5

<210> SEQ ID NO 84
<211> LENGTH: 12
<212> TYPE: PRT
<213> ORGANISM: Artificial
<220> FEATURE:
<223> OTHER INFORMATION: Synthetic
<220> FEATURE:
```

```
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: Met(O2)
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 84

Gly Ser Gln His Ser Xaa Glu Met Phe Arg Trp Lys
1               5                   10

<210> SEQ ID NO 85
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 4-(Hexadecanoylsulfamoyl)butanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: Met(O2)
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 85

Gly Ser Gln Arg Ser Xaa Glu Met Phe Arg Trp Lys
1               5                   10

<210> SEQ ID NO 86
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MOD_RES
```

```
<222> LOCATION: (4)..(4)
<223> OTHER INFORMATION: HomoArg
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 3-PyAla
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 86

Gly Ser Gln Arg Ser Xaa Glu Ala Phe Arg Trp Lys
1               5                   10

<210> SEQ ID NO 87
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: Met(O2)
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 87

Gly Ser Gln Arg Ser Xaa Glu Met Phe Arg Trp Lys
1               5                   10

<210> SEQ ID NO 88
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 4-(Hexadecanoylsulfamoyl)butanoyl-Gly
<220> FEATURE:
<221> NAME/KEY: MISC_FEATURE
<222> LOCATION: (6)..(6)
```

```
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 88

Gly Ser Gln Arg Ser Xaa Glu Gln Phe Arg Trp Lys
1               5                   10

<210> SEQ ID NO 89
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 3-(2-(2-[2-(2-(Hexadecanoylamino)ethoxy)
      ethoxy]ethoxy)ethoxy)propionyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 89

Xaa Glu Pro Phe Arg Trp Lys
1               5

<210> SEQ ID NO 90
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 2-[2-(Hexadecanoylamino)ethoxy]ethoxyacetyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
```

```
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 90

Gly Ser Gln His Ser Xaa Glu Pro Phe Arg Trp Lys
1               5                   10

<210> SEQ ID NO 91
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 2-[2-(Tetradecanoylamino)ethoxy]ethoxyacetyl-
      Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 91

Gly Ser Gln His Ser Xaa Glu Pro Phe Arg Trp Lys
1               5                   10

<210> SEQ ID NO 92
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
```

<223> OTHER INFORMATION: AMIDATION

<400> SEQUENCE: 92

Gly Thr Gln His Ser Xaa Glu Pro Phe Arg Trp Lys
1               5                   10

<210> SEQ ID NO 93
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 93

Gly Gln Gln His Ser Xaa Glu Pro Phe Arg Trp Lys
1               5                   10

<210> SEQ ID NO 94
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 94

Gly Thr Gln His Ser Xaa Glu Asn Phe Arg Trp Lys
1               5                   10

<210> SEQ ID NO 95

```
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (7)..(7)
<223> OTHER INFORMATION: Nle
<220> FEATURE:
<221> NAME/KEY: MOD_RES
<222> LOCATION: (8)..(13)
<223> OTHER INFORMATION: Lactam bridge
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (10)..(10)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 95

Gly Glu Thr Gln His Ser Xaa Glu Pro Phe Arg Trp Lys
1               5                   10

<210> SEQ ID NO 96
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Glu
<220> FEATURE:
<221> NAME/KEY: MISC_FEATURE
<222> LOCATION: (7)..(7)
<223> OTHER INFORMATION: Nle
<220> FEATURE:
<221> NAME/KEY: MOD_RES
<222> LOCATION: (8)..(13)
<223> OTHER INFORMATION: Lactam bridge
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (10)..(10)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 96

Glu Gly Thr Gln His Ser Xaa Glu Pro Phe Arg Trp Lys
1               5                   10

<210> SEQ ID NO 97
<211> LENGTH: 13
<212> TYPE: PRT
<213> ORGANISM: Artificial
<220> FEATURE:
<223> OTHER INFORMATION: Synthetic
```

```
<220> FEATURE:
<221> NAME/KEY: MOD_RES
<222> LOCATION: (1)..(1)
<223> OTHER INFORMATION: Hexadecanoyl-Glu
<220> FEATURE:
<221> NAME/KEY: MISC_FEATURE
<222> LOCATION: (2)..(2)
<223> OTHER INFORMATION: 4Abu
<220> FEATURE:
<221> NAME/KEY: MISC_FEATURE
<222> LOCATION: (7)..(7)
<223> OTHER INFORMATION: Nle
<220> FEATURE:
<221> NAME/KEY: MOD_RES
<222> LOCATION: (8)..(13)
<223> OTHER INFORMATION: Lactam bridge
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (10)..(10)
<223> OTHER INFORMATION: D form
<220> FEATURE:
<221> NAME/KEY: MOD_RES
<222> LOCATION: (13)..(13)
<223> OTHER INFORMATION: AMIDATION

<400> SEQUENCE: 97

Glu Xaa Thr Gln His Ser Xaa Glu Pro Phe Arg Trp Lys
1               5                   10

<210> SEQ ID NO 98
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 2-[2-(Hexadecanoylamino)ethoxy]ethoxyacetyl-His
<220> FEATURE:
<221> NAME/KEY: MISC_FEATURE
<222> LOCATION: (3)..(3)
<223> OTHER INFORMATION: Nle
<220> FEATURE:
<221> NAME/KEY: MOD_RES
<222> LOCATION: (4)..(9)
<223> OTHER INFORMATION: Lactam bridge
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (6)..(6)
<223> OTHER INFORMATION: D form
<220> FEATURE:
<221> NAME/KEY: MOD_RES
<222> LOCATION: (9)..(9)
<223> OTHER INFORMATION: AMIDATION

<400> SEQUENCE: 98

His Ser Xaa Glu Pro Phe Arg Trp Lys
1               5

<210> SEQ ID NO 99
<211> LENGTH: 9
<212> TYPE: PRT
<213> ORGANISM: Artificial
<220> FEATURE:
<223> OTHER INFORMATION: Synthetic
<220> FEATURE:
```

```
<221> NAME/KEY: MOD_RES
<222> LOCATION: (1)..(1)
<223> OTHER INFORMATION: 2-[2-(Hexadecanoylamino)ethoxy]ethoxyacetyl-Arg
<220> FEATURE:
<221> NAME/KEY: MISC_FEATURE
<222> LOCATION: (3)..(3)
<223> OTHER INFORMATION: Nle
<220> FEATURE:
<221> NAME/KEY: MOD_RES
<222> LOCATION: (4)..(9)
<223> OTHER INFORMATION: Lactam bridge
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (6)..(6)
<223> OTHER INFORMATION: D form
<220> FEATURE:
<221> NAME/KEY: MOD_RES
<222> LOCATION: (9)..(9)
<223> OTHER INFORMATION: AMIDATION

<400> SEQUENCE: 99

Arg Ser Xaa Glu Pro Phe Arg Trp Lys
1               5

<210> SEQ ID NO 100
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 2-[2-(Hexadecanoylamino)ethoxy]ethoxyacetyl-Gln
<220> FEATURE:
<221> NAME/KEY: MISC_FEATURE
<222> LOCATION: (3)..(3)
<223> OTHER INFORMATION: Nle
<220> FEATURE:
<221> NAME/KEY: MOD_RES
<222> LOCATION: (4)..(9)
<223> OTHER INFORMATION: Lactam bridge
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (6)..(6)
<223> OTHER INFORMATION: D form
<220> FEATURE:
<221> NAME/KEY: MOD_RES
<222> LOCATION: (9)..(9)
<223> OTHER INFORMATION: AMIDATION

<400> SEQUENCE: 100

Gln Ser Xaa Glu Pro Phe Arg Trp Lys
1               5

<210> SEQ ID NO 101
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 2-[2-(Hexadecanoylamino)ethoxy]ethoxyacetyl-Glu
<220> FEATURE:
<221> NAME/KEY: MISC_FEATURE
```

```
<222> LOCATION: (3)..(3)
<223> OTHER INFORMATION: Nle
<220> FEATURE:
<221> NAME/KEY: MOD_RES
<222> LOCATION: (4)..(9)
<223> OTHER INFORMATION: Lactam bridge
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (6)..(6)
<223> OTHER INFORMATION: D form
<220> FEATURE:
<221> NAME/KEY: MOD_RES
<222> LOCATION: (9)..(9)
<223> OTHER INFORMATION: AMIDATION

<400> SEQUENCE: 101

Glu Ser Xaa Glu Pro Phe Arg Trp Lys
1               5

<210> SEQ ID NO 102
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 2-[2-(2-{2-[2-(Dodecanoylamino)
      ethoxy]ethoxy}acetylamino)ethoxy]ethoxyacetyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 102

Xaa Glu Pro Phe Arg Trp Lys
1               5

<210> SEQ ID NO 103
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 2-{2-[4-Carbamoyl-2-(2-(hexadecanoylamino)
      acetylamino)butyrylamino]ethoxy}ethoxyacetyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
```

```
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 103

Xaa Glu Pro Phe Arg Trp Lys
1               5

<210> SEQ ID NO 104
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: -{2-[4-Carboxy-2-(2-(hexadecanoylamino)
      acetylamino)butyrylamino]ethoxy}ethoxyacetyl-Nle
<220> FEATURE:
<221> NAME/KEY: MISC_FEATURE
<222> LOCATION: (1)..(1)
<223> OTHER INFORMATION: 2-{2-[4-Carboxy-2-(2-(hexadecanoylamino)
      acetylamino)butyrylamino]ethoxy}ethoxyacetyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 104

Xaa Glu Pro Phe Arg Trp Lys
1               5

<210> SEQ ID NO 105
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 2-{2-[2-(2-(Hexadecanoylamino)acetylamino)-3-
      (imidazol-4-yl)propionylamino]ethoxy}ethoxyacteyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
```

```
<223> OTHER INFORMATION: AMIDATION

<400> SEQUENCE: 105

Xaa Glu Pro Phe Arg Trp Lys
1               5

<210> SEQ ID NO 106
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Dodecanoyl-Nle
<220> FEATURE:
<221> NAME/KEY: MOD_RES
<222> LOCATION: (2)..(7)
<223> OTHER INFORMATION: Lactam bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 106

Xaa Glu Pro Phe Arg Trp Lys
1               5

<210> SEQ ID NO 107
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 107

Gly Thr Asn Asn Thr Xaa Glu Pro Phe Arg Trp Lys
1               5                   10

<210> SEQ ID NO 108
```

```
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Octanoyl-Gly
<220> FEATURE:
<221> NAME/KEY: MOD_RES
<222> LOCATION: (3)..(3)
<223> OTHER INFORMATION: D form
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 108

Gly Ser Gln His Thr Xaa Glu Pro Phe Arg Trp Lys
1               5                   10

<210> SEQ ID NO 109
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: decanoyl-Gly
<220> FEATURE:
<221> NAME/KEY: MOD_RES
<222> LOCATION: (3)..(3)
<223> OTHER INFORMATION: D form
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 109

Gly Ser Gln His Thr Xaa Glu Pro Phe Arg Trp Lys
1               5                   10
```

<210> SEQ ID NO 110
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Dodecanoyl-Gly
<220> FEATURE:
<221> NAME/KEY: MOD_RES
<222> LOCATION: (3)..(3)
<223> OTHER INFORMATION: D form
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 110

Gly Ser Gln His Thr Xaa Glu Pro Phe Arg Trp Lys
1               5                   10

<210> SEQ ID NO 111
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Tetradecanoyl-Gly
<220> FEATURE:
<221> NAME/KEY: MOD_RES
<222> LOCATION: (3)..(3)
<223> OTHER INFORMATION: D form
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 111

```
Gly Ser Gln His Thr Xaa Glu Pro Phe Arg Trp Lys
1               5                   10
```

<210> SEQ ID NO 112
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MOD_RES
<222> LOCATION: (3)..(3)
<223> OTHER INFORMATION: D form
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 112

```
Gly Ser Gln His Thr Xaa Glu Pro Phe Arg Trp Lys
1               5                   10
```

<210> SEQ ID NO 113
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Octadecanoyl-Gly
<220> FEATURE:
<221> NAME/KEY: MOD_RES
<222> LOCATION: (3)..(3)
<223> OTHER INFORMATION: D form
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)

```
<223> OTHER INFORMATION: AMIDATION

<400> SEQUENCE: 113

Gly Ser Gln His Thr Xaa Glu Pro Phe Arg Trp Lys
1               5                   10

<210> SEQ ID NO 114
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4-Fluoro-Pro
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 114

Gly Ser Gln His Ser Xaa Glu Pro Phe Arg Trp Lys
1               5                   10

<210> SEQ ID NO 115
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MOD_RES
<222> LOCATION: (4)..(4)
<223> OTHER INFORMATION: HomoArg
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4-Fluoro-Pro
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION
```

```
<400> SEQUENCE: 115

Gly Ser Gln Arg Ser Xaa Glu Pro Phe Arg Trp Lys
1               5                   10

<210> SEQ ID NO 116
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MOD_RES
<222> LOCATION: (4)..(4)
<223> OTHER INFORMATION: Homo-Arg
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4-Fluoro-Pro
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 116

Gly Ser Gln Arg Thr Xaa Glu Pro Phe Arg Trp Lys
1               5                   10

<210> SEQ ID NO 117
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MOD_RES
<222> LOCATION: (4)..(4)
<223> OTHER INFORMATION: HomoArg
<220> FEATURE:
<221> NAME/KEY: MISC_FEATURE
<222> LOCATION: (7)..(7)
<223> OTHER INFORMATION: Nle
<220> FEATURE:
<221> NAME/KEY: MOD_RES
<222> LOCATION: (8)..(13)
<223> OTHER INFORMATION: Lactam bridge
<220> FEATURE:
<221> NAME/KEY: MOD_RES
<222> LOCATION: (9)..(9)
<223> OTHER INFORMATION: 4-Fluoro-Pro
<220> FEATURE:
<221> NAME/KEY: MOD_RES
<222> LOCATION: (10)..(10)
<223> OTHER INFORMATION: D form
<220> FEATURE:
```

```
<221> NAME/KEY: MOD_RES
<222> LOCATION: (13)..(13)
<223> OTHER INFORMATION: AMIDATION

<400> SEQUENCE: 117

Gly Ser Asn Arg Thr Ser Xaa Glu Pro Phe Arg Trp Lys
1               5                   10

<210> SEQ ID NO 118
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 3-{2-[2-(2-{2-[4-(4,4,5,5,6,6,7,7,8,8,9,9,10,
      10,10-Pentadecafluorodecanoylsulfamoyl)butyrylamino]ethoxy}ethoxy)
      ethoxy]ethoxy}propionyl-Gly
<220> FEATURE:
<221> NAME/KEY: MOD_RES
<222> LOCATION: (4)..(4)
<223> OTHER INFORMATION: HomoArg
<220> FEATURE:
<221> NAME/KEY: MISC_FEATURE
<222> LOCATION: (5)..(5)
<223> OTHER INFORMATION: Nle
<220> FEATURE:
<221> NAME/KEY: MOD_RES
<222> LOCATION: (6)..(11)
<223> OTHER INFORMATION: Lactam bridge
<220> FEATURE:
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (8)..(8)
<223> OTHER INFORMATION: D form
<220> FEATURE:
<221> NAME/KEY: MOD_RES
<222> LOCATION: (11)..(11)
<223> OTHER INFORMATION: AMIDATION

<400> SEQUENCE: 118

Gly Ser Gln Ala Xaa Glu Pro Phe Arg Trp Leu
1               5                   10

<210> SEQ ID NO 119
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
```

```
<220> FEATURE:
<221> NAME/KEY: MOD_RES
<222> LOCATION: (12)..(12)
<223> OTHER INFORMATION: AMIDATION

<400> SEQUENCE: 119

Gly Ser Ser Tyr Thr Xaa Glu Pro Phe Arg Trp Lys
1               5                   10

<210> SEQ ID NO 120
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 120

Gly Ser Asn Asn Thr Xaa Glu Pro Phe Arg Trp Lys
1               5                   10

<210> SEQ ID NO 121
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MOD_RES
<222> LOCATION: (4)..(4)
<223> OTHER INFORMATION: HomoArg
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
```

```
<221> NAME/KEY: MOD_RES
<222> LOCATION: (12)..(12)
<223> OTHER INFORMATION: AMIDATION

<400> SEQUENCE: 121

Gly Ser Ser Arg Thr Xaa Glu Pro Phe Arg Trp Lys
1               5                   10

<210> SEQ ID NO 122
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 122

Gly Ser Ser His Thr Xaa Glu Pro Phe Arg Trp Lys
1               5                   10

<210> SEQ ID NO 123
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MOD_RES
<222> LOCATION: (3)..(3)
<223> OTHER INFORMATION: D form
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
```

```
<222> LOCATION: (12)..(12)
<223> OTHER INFORMATION: AMIDATION

<400> SEQUENCE: 123

Gly Ser Asn His Thr Xaa Glu Pro Phe Arg Trp Lys
1               5                   10

<210> SEQ ID NO 124
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gly
<220> FEATURE:
<221> NAME/KEY: MOD_RES
<222> LOCATION: (4)..(4)
<223> OTHER INFORMATION: HomoArg
<220> FEATURE:
<221> NAME/KEY: MISC_FEATURE
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Lactam bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 124

Gly Ser Asn Arg Thr Xaa Glu Pro Phe Arg Trp Lys
1               5                   10

<210> SEQ ID NO 125
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Ser
<220> FEATURE:
<221> NAME/KEY: MOD_RES
<222> LOCATION: (2)..(2)
<223> OTHER INFORMATION: HomoArg
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Lactam bridge
<220> FEATURE:
<221> NAME/KEY: MOD_RES
<222> LOCATION: (6)..(6)
<223> OTHER INFORMATION: Met(O2)
<220> FEATURE:
<221> NAME/KEY: MOD_RES
<222> LOCATION: (7)..(7)
```

```
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 125

Ser Arg Ser Xaa Glu Met Phe Arg Trp Lys
1               5                   10

<210> SEQ ID NO 126
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Gln
<220> FEATURE:
<221> NAME/KEY: MOD_RES
<222> LOCATION: (2)..(2)
<223> OTHER INFORMATION: HomoArg
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Lactam bridge
<220> FEATURE:
<221> NAME/KEY: MOD_RES
<222> LOCATION: (6)..(6)
<223> OTHER INFORMATION: Met(O2)
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 126

Gln Arg Thr Xaa Glu Met Phe Arg Trp Lys
1               5                   10

<210> SEQ ID NO 127
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-ser
<220> FEATURE:
<221> NAME/KEY: MOD_RES
<222> LOCATION: (2)..(2)
<223> OTHER INFORMATION: HomoArg
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Lactam bridge
<220> FEATURE:
<221> NAME/KEY: MOD_RES
<222> LOCATION: (6)..(6)
<223> OTHER INFORMATION: Met(O2)
```

```
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 127

Ser Arg Thr Xaa Glu Met Phe Arg Trp Lys
1               5                   10

<210> SEQ ID NO 128
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Ser
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Lactam bridge
<220> FEATURE:
<221> NAME/KEY: MOD_RES
<222> LOCATION: (6)..(6)
<223> OTHER INFORMATION: Met(O2)
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 128

Ser His Thr Xaa Glu Met Phe Arg Trp Lys
1               5                   10

<210> SEQ ID NO 129
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Hexadecanoyl-Ser
<220> FEATURE:
<221> NAME/KEY: MOD_RES
<222> LOCATION: (2)..(2)
<223> OTHER INFORMATION: HomoArg
<220> FEATURE:
<221> NAME/KEY: MISC_FEATURE
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Lactam bridge
<220> FEATURE:
<221> NAME/KEY: MOD_RES
<222> LOCATION: (6)..(6)
<223> OTHER INFORMATION: Met(O2)
<220> FEATURE:
```

```
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 129

Ser Arg Thr Xaa Glu Met Phe Arg Trp Lys
1               5                   10
```